(12) United States Patent
Bell et al.

(10) Patent No.: US 6,235,742 B1
(45) Date of Patent: May 22, 2001

(54) 5-SUBSTITUTED PYRAZOLO[4,3-D] PYRIMIDIN-7-ONES

(75) Inventors: Andrew Simon Bell; Nicholas Kenneth Terrett, both of Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/176,166

(22) Filed: Oct. 21, 1998

(30) Foreign Application Priority Data

Oct. 24, 1997 (GB) .................................................. 9722520

(51) Int. Cl.[7] .......................... A61K 31/519; A61P 9/10; A61P 9/12; C07D 487/04
(52) U.S. Cl. ............................................. 514/258; 544/262
(58) Field of Search ............................... 544/262; 514/258

(56) References Cited

U.S. PATENT DOCUMENTS

| | | | |
|---|---|---|---|
| 4,663,326 | 5/1987 | Hamilton | 514/258 |
| 4,666,908 | 5/1987 | Hamilton | 514/229 |
| 5,250,534 | 10/1993 | Bell et al. | 514/258 |
| 5,272,147 | 12/1993 | Bell et al. | 514/234.2 |
| 5,346,901 | 9/1994 | Bell et al. | 514/258 |
| 5,426,107 | 6/1995 | Bell et al. | 514/234.2 |
| 5,719,283 | 2/1998 | Bell et al. | 544/262 |
| 5,734,053 | 3/1998 | Terrett | 544/277 |
| 5,955,611 | 9/1999 | Dunn et al. | 544/262 |

FOREIGN PATENT DOCUMENTS

| | | | |
|---|---|---|---|
| 0463756 | 1/1992 | (EP) . | |
| 0526004 | 2/1993 | (EP) . | |
| 0349239 | 3/1994 | (EP) | C07D/487/04 |
| 0636626 | 2/1995 | (EP) | C07D/487/04 |
| 0526004 | 8/1997 | (EP) | C07D/487/04 |
| WO9306104 | 4/1993 | (WO) | C07D/487/04 |
| WO9307149 | 4/1993 | (WO) | C07D/487/04 |
| WO9312095 | 6/1993 | (WO) | C07D/239/91 |
| WO9400453 | 1/1994 | (WO) | C07D/473/30 |
| WO9405661 | 3/1994 | (WO) | C07D/471/04 |
| WO9428902 | 12/1994 | (WO) . | |
| WO9616644 | 6/1996 | (WO) | A61K/31/00 |
| WO9616657 | 6/1996 | (WO) | A61K/31/505 |
| WO9628429 | 9/1996 | (WO) | C07D/239/70 |
| WO9628448 | 9/1996 | (WO) | C07D/487/04 |
| WO9849166 | 11/1998 | (WO) | C07D/487/04 |
| WO9954333 | 10/1999 | (WO) | C07D/487/04 |

OTHER PUBLICATIONS

Hamilton, et al., J. Med. Chem. 1987, 30, 91–96.
Dumaltre et al. J. Med. Chem., 1996, 39, 1635–1644.
JP Abstract 08253484.

*Primary Examiner*—Richard L. Raymond
*Assistant Examiner*—Venkataraman Balasubramanian
(74) *Attorney, Agent, or Firm*—Peter C. Richardson; Gregg C. Benson; James T. Jones

(57) ABSTRACT

Compounds are disclosed which are useful as PDE1 inhibitors. The compounds have the formula:

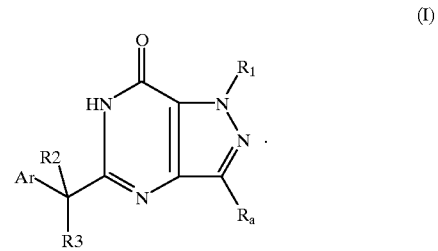

(I)

22 Claims, No Drawings

5-SUBSTITUTED PYRAZOLO[4,3-D] PYRIMIDIN-7-ONES

The present invention relates to compounds, including inter alia pharmaceutical compositions comprising the same and methods for making the same.

In particular, the present invention relates to compounds that are capable of exhibiting inhibition of a phosphodiesterase (PDE) enzyme.

More in particular, the present invention relates to compounds that are capable of exhibiting at least inhibition of a phosphodiesterase type 1 (PDE1) enzyme—i.e. the compounds are capable of acting as inhibitors of PDE1. Some of these compounds are also capable of exhibiting inhibition of other types of PDE enzymes—such as a phosphodiesterase type 5 (PDE5) enzyme.

By way of background information, EP-A-0201188 discloses certain 5-substituted pyrazolo[4,3-d]pyrimidin-7-ones and suggests their use for the treatment of cardiovascular disorders, such as heart failure or cardiac insufficiency. EP-A-0201188 also suggests the use of those 5-substituted pyrazolo[4,3-d]pyrimidin-7-ones to inhibit PDE.

In particular, Example 1 of EP-A-0201188 discloses the following 5-substituted pyrazolo[4,3-d]pyrimidin-7-one:

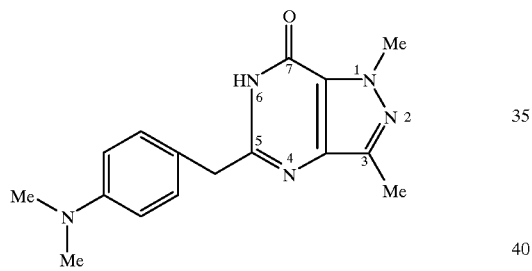

For ease of reference this compound will be referred to as the '188 Compound. Like the '188 compound, all of the compounds of EP-A-0201188 have a methyl group attached at the 3 position of the pyrazolo[4,3-d]pyrimidine ring system.

We have found that the '188 compound is at least a weak PDE1 inhibitor.

Furthermore, as there is now a body of evidence associating PDE1 with a number of diseases, e.g. stroke, dementia, memory enhancement, atherosclerosis, urge incontinence, hypertension, angina pectoris, congestive heart failure, myocardial infarction and restenosis, so there is a need to have more potent PDE1 inhibitors.

There is also a need to have more selective PDE inhibitors, in particular PDE1 inhibitors.

The present invention seeks to provide compounds that are useful as PDE1 inhibitors, including pharmaceutical compositions comprising the same and methods for making the same.

According to a first aspect of the present invention there is provided a compound of the formula (I)

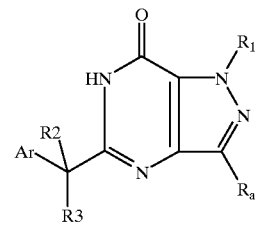

(I)

wherein
$R_a$ is $C_2$–$C_6$ alkyl;
$R_1$ is H or $C_1$–$C_4$ alkyl;
  each of $R_2$ and $R_3$ is independently selected from H and $C_1$–$C_4$ alkyl, or
  $R_2$ is H or $C_1$–$C_4$ alkyl and $R_3$ is OH, $C_2$–$C_4$ alkanoyloxy or fluoro, or
  $R_2$ and $R_3$ when taken together represent $C_2$–$C_6$ alkylene, or
  $R_2$ and $R_3$ when taken together with the carbon atom to which they are attached represent a carbonyl group;
Ar is either (a)

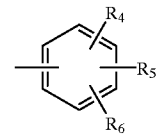

wherein each of $R_4$, $R_5$ and $R_6$ is independently selected from
H,
$C_1$–$C_4$ alkyl,
$C_1$–$C_4$ alkoxy,
$C_1$–$C_4$ alkoxy-Z—,
halo,
halo($C_1$–$C_4$)alkyl,
phenoxy, optionally substituted by up to three substituents each of which substituent is independently selected from halo, $C_{1-4}$ alkyl, and $C_1$–$C_4$ alkoxy,
nitro,
hydroxy,
hydroxy-Z—,
$C_2$–$C_4$ alkanoyl,
amino,
amino-Z—,
($C_1$–$C_4$ alkyl)NH,
($C_1$–$C_4$ alkyl)$_2$N—,
($C_1$–$C_4$ alkyl)NH—Z—
($C_1$–$C_4$ alkyl)$_2$N—Z—,
—COOH,
—Z—COOH,
—COO($C_1$–$C_4$ alkyl),
—Z—COO($C_1$–$C_4$ alkyl)
$C_1$–$C_4$ alkanesulphonamido,
$C_1$–$C_4$ alkanesulphonamido-Z—,
halo($C_1$–$C_4$)alkanesulphonamido,
halo($C_1$–$C_4$)alkanesulphonamido-Z—,
$C_1$–$C_4$ alkanamido,
$C_1$–$C_4$ alkanamido-Z—,
HOOC—Z—NH—,
HOOC—Z—NH—Z—,
($C_1$–$C_4$ alkyl)OOC—Z—NH—,
($C_1$–$C_4$ alkyl)OOC—Z—NH—Z—, $C_1$–$C_4$ alkl-NH—$SO_2$—NH—,
$C_1$–$C_4$ alkyl-NH—$SO_2$—NH—Z—,
($C_1$–$C_4$ alkyl)$_2$-N—$SO_2$—NH—,
($C_1$–$C_4$ alkyl)$_2$-N—$SO_2$—NH—Z—,
$C_1$–$C_4$ alkoxy CH=CH—Z—CONH—,
$C_1$–$C_4$ alkoxy CH=CHCONH
$C_1$–$C_4$ alkyl-$SO_2$—N($C_1$–$C_4$ alkyl)-,
$C_1$–$C_4$ alkyl-$SO_2$—N($C_1$–$C_4$ alkyl)-Z—,
($C_1$–$C_4$ alkyl)NH—Z—$SO_2$—NH—,
($C_1$–$C_4$ alkyl)$_2$N—Z—$SO_2$—NH—,
($C_1$–$C_4$ alkyl)NH—Z—$SO_2$—NH—Z—,
($C_1$–$C_4$ alkyl)$_2$N—Z—$SO_2$—NH—Z—,
benzenesulphonamido, optionally ring substituted by up to three substitutents each of which is independently selected from halo, $C_{1-4}$ alkyl, and $C_1$–$C_4$ alkoxy,
$C_1$–$C_4$ alkanoyl-N($C_1$–$C_4$ alkyl)-,
$C_1$–$C_4$ alkanoyl-N($C_1$–$C_4$ alkyl)-Z—,
$C_1$–$C_4$ alkoxycarbonyl-CH($CH_2OH$)$NHSO_2$—,
—$SO_3H$,
—$SO_2NH_2$,
$H_2NOC$—CH($CH_2OH$)—$NHSO_2$—,
HOOC—Z—O—, and
($C_1$–$C_4$ alkyl)OOC—Z—O—,
or optionally one of $R_4$, $R_5$ and $R_6$ is a G-Het group and wherein the others of $R_4$, $R_5$ and $R_6$ are independently selected from the $R_4$, $R_5$ and $R_6$ subsituents listed above;
Z is $C_1$–$C_4$ alkylene,
G is a direct link, Z, O, —$SO_2NH$—, $SO_2$, or —Z—N ($C_1$–$C_4$ alkyl)$SO_2$—,
Het is a 5- or 6-membered heterocyclic group containing 1, 2, 3 or 4 nitrogen heteroatoms; or 1 or 2 nitrogen heteroatoms and 1 sulphur heteroatom or 1 oxygen heteroatom; or the heterocyclic group is furanyl or thiophenyl; wherein the Het group is saturated or partially or fully unsaturated and optionally substituted by up to 3 substituents, wherein each substituent is independently selected from $C_1$–$C_4$ alkyl, oxo, hydroxy, halo, and halo($C_1$–$C_4$) alkyl;
or (b) any one of the following bicyclic groups:
benzodioxolanyl,
benzodioxanyl,
benzimidazolyl,
quinolinyl,
indolyl,
quinazolinyl,
isoquinolinyl,
benzotriazolyl,
benzofuranyl,
benzothiophenyl,
quinoxalinyl, or
phthalizinyl,
wherein said bicyclic Ar groups are linked to the neighbouring —C($R_2R_3$)— group via the benzo ring portion, and wherein the heterocyclic portion of said bicyclic Ar group is optionally partially or fully saturated, said group being optionally substituted by one or more of $C_1$–$C_4$ alkyl, halo, hydroxy, oxo, amino, and $C_1$–$C_4$ alkoxy;
or a pharmaceutically acceptable salt of the compound, or a pharmaceutically acceptable solvate of the compound or the salt.

This and some of the other aspects of the present invention, as well as some preferred embodiments of the present invention, are presented in the accompanying claims.

It will also be appreciated that what is to be claimed includes the following:

(i) a compound of the formula (I) or a pharmaceutically acceptable salt thereof;

(ii) one or more processes for the preparation of a compound of the formula (I) or a pharmaceutically acceptable salt thereof;

(iii) novel intermediates for use in any one of those processes;

(iv) a pharmaceutical composition comprising a compound of the formula (I), or a pharmaceutically acceptable salt thereof, admixed with a pharmaceutically acceptable diluent, carrier or excipient;

(v) a compound of the formula (I), or a pharmaceutically acceptable salt or composition thereof, for use as a medicament;

(vi) the use of a compound of the formula (I), or of a pharmaceutically acceptable salt or composition thereof, for the manufacture of a medicament for the treatment of conditions capable of being treated by the inhibition of PDE enzymes;

(vii) use as in (vi) wherein the medicament is for use as an inhibitor for PDE1;

(viii) a method of treatment of a subject (e.g. a mammal) in need of same, which method comprises administering to the subject an effective amount of a compound of the formula (I) or a pharmaceutically acceptable salt or composition thereof, and wherein the compound, salt or composition produces an inhibitory effect against a PDE; and (ix) a method as in (viii) wherein the compound, salt or composition produces an inhibitory effect against PDE1.

By way of example, a preferred process according to one embodiment of the present invention for preparing compounds according to the present invention is presented by the following scheme:

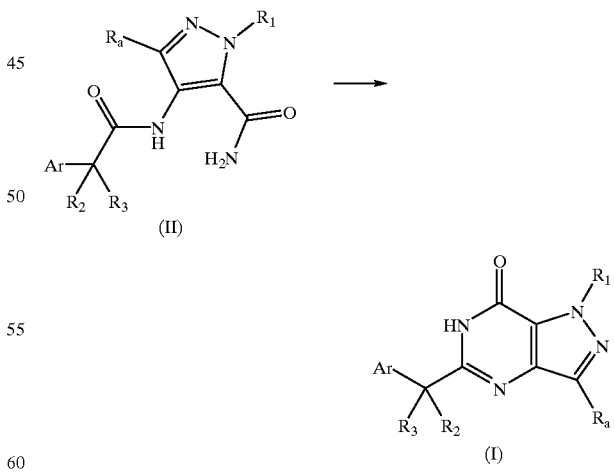

wherein each of the groups are as defined above.

By way of further example, a preferred process according to another embodiment of the present invention for preparing compounds according to the present invention is presented by the following scheme:

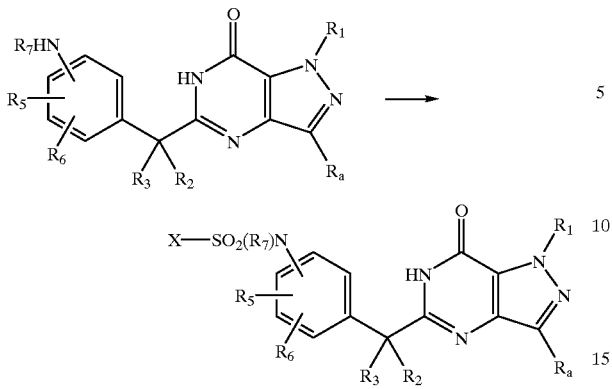

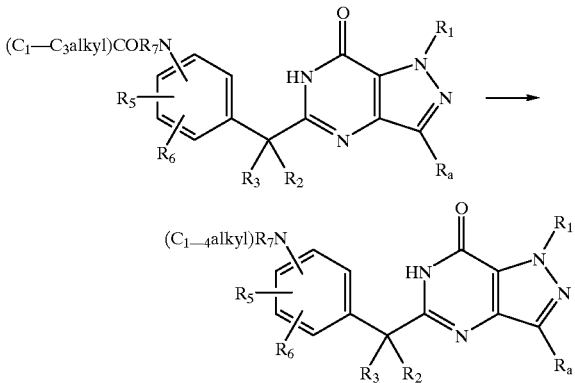

wherein each of the groups are as defined above, and wherein $R_7$ is H or $C_{1-4}$ alkyl, and wherein X is $C_{1-4}$ alkyl, halo($C_{1-4}$)alkyl, or optionally substituted phenyl.

By way of further example, a preferred process according to another embodiment of the present invention for preparing compounds according to the present invention is presented by the following scheme:

wherein each of the groups are as defined above.

By way of example, a preferred intermediate for one embodiment of the present invention is

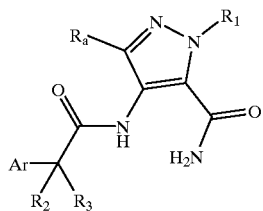

wherein each of the groups are as defined above.

By way of further example, a preferred intermediate for another embodiment of the present invention is

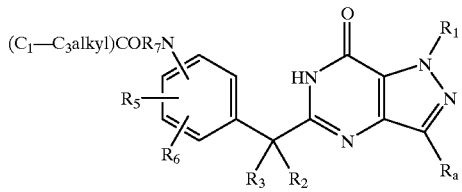

wherein each of the groups are as defined above.

By way of further example, a preferred intermediate for another embodiment of the present invention is wherein each of the groups are as defined above.

A key advantage of the present invention is that it provides compounds, and compositions comprising the same, that are useful as PDE1 inhibitors.

Another key advantage of the compounds of the present invention is that some are selective PDE inhibitors, in particular selective PDE1 inhibitors.

As indicated above, the compounds of the present invention are of the general formula (I). We have surprisingly found that these compounds are effective as PDE1 inhibitors and at low concentrations. This result is surprising because the compounds of EP-A-0201188, such as the '188 compound, are not as effective at such low concentrations. This highly surprising result is borne out by the experimental data presented in the experimental section (infra).

The compounds of the present invention may exist in hydrated or solvated forms.

Alkyl and alkylene groups, when present in any one of the above-defined groups for the compounds of the formula (I), may be linear or branched.

The term "halo" as used herein means means F, Cl, Br or I.

The pharmaceutically acceptable salts of the compounds of the formula (I) include suitable acid addition or base salts thereof. For a review on suitable pharmaceutical salts see Berge et al, J Pharm Sci, 66, 1–19 (1977).

By way of example, suitable acid addition salts are formed from acids which form non-toxic salts. Suitable examples of such salts are the hydrochloride, hydrobromide, hydroiodide, sulphate, bisulphate, phosphate, hydrogen phosphate, acetate, maleate, fumarate, lactate, tartrate, citrate, gluconate, benzoate, methanesulphonate, benzenesulphonate and p-toluenesulphonate salts.

Also by way of example, suitable base salts are formed from bases which form non-toxic salts. Suitable examples thereof are the aluminium, calcium, lithium, magnesium, potassium, sodium, zinc, N-benzyl-N-(2-phenylethyl) amine, 1-adamantylamine and diethanolamine salts.

Compounds of the present invention may contain one or more asymmetric carbon atoms and/or one or more non-aromatic carbon-carbon double bonds and may therefore exist in two or more stereoisomeric forms. Thus, the present invention also provides both the individual stereoisomers of the compounds of the formula (I), as well as mixtures thereof, including compositions comprising the same. Separation of diastereoisomers or cis and trans isomers may be achieved by conventional techniques, e.g. by fractional crystallisation, chromatography or HPLC of a stereoisomeric mixture of a compound of the formula (I) or a suitable salt or derivative thereof. An individual enantiomer of a compound of the formula (I) may also be prepared from a corresponding optically pure intermediate or by resolution, such as by HPLC of a racemate using a suitable chiral support or by fractional crystallisation of the diastereoisomeric salts formed by reaction of a racemate with a suitable optically active acid or base.

As mentioned above, the present invention also covers pharmaceutical compositions comprising the compounds of the general formula (I). In this regard, and in particular for human therapy, even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical practice.

By way of example, in the pharmaceutical compositions of the present invention, the compounds of the present invention may be admixed with any suitable binder(s), lubricant(s), suspending agent(s), coating agent(s), or solubilising agent(s).

In general, a therapeutically effective daily oral or intravenous dose of the compounds of formula (I) and their salts is likely to range from 0.01 to 50 mg/kg body weight of the subject to be treated, preferably 0.1 to 20 mg/kg. The compounds of the formula (I) and their salts may also be administered by intravenous infusion, at a dose which is likely to range from 0.001–10 mg/kg/hr.

Tablets or capsules of the compounds may be administered singly or two or more at a time, as appropriate. It is also possible to administer the compounds in sustained release formulations.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the compounds of the general formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the compounds of the present invention and their pharmaceutically acceptable salts and solvates may typically be from 10 to 500 mg (in single or divided doses). Thus, and by way of example, tablets or capsules may contain from 5 to 100 mg of active compound for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

Generally, in humans, oral administration of the compounds of the invention is the preferred route, being the most convenient and, for example in male erectile dysfunction (MED), avoiding the well-known disadvantages associated with intracavernosal (i.c.) administration. A preferred oral dosing regimen in MED for a typical man is from 25 to 100 mg of compound when required. In circumstances where the recipient suffers from a swallowing disorder or from impairment of drug absorption after oral administration, the drug may be administered parenterally, e.g. sublingually or buccally.

For veterinary use, a compound of the present invention or a veterinarily acceptable salt thereof, or a veterinarily acceptable solvate of either entity, is typically administered as a suitably acceptable formulation in accordance with normal veterinary practice and the veterinary surgeon will determine the dosing regimen and route of administration which will be most appropriate for a particular animal. However, as with human treatment, it may be possible to administer the compound alone for veterinary treatments.

Thus the invention provides a pharmaceutical composition comprising a compound of the present invention, or a pharmaceutically acceptable salt thereof, or a pharmaceutically acceptable solvate of either entity, together with a pharmaceutically acceptable diluent, excipient or carrier.

The present invention also provides a veterinary formulation comprising a compound of the present invention, or a veterinarily acceptable salt thereof, or a veterinarily acceptable solvate of either entity, together with a veterinarily acceptable diluent, excipient or carrier.

The invention further provides a compound of the present invention, or a pharmaceutically acceptable salt thereof, or a pharmaceutically acceptable solvate of either entity, or a pharmaceutical composition containing any of the foregoing, for use as a human medicament.

In addition, the present invention provides a compound of the present invention, or a veterinarily acceptable salt thereof, or a veterinarily acceptable solvate of either entity, or a veterinary formulation containing any of the foregoing, for use as an animal medicament.

In yet another aspect, the invention provides the use of a compound of the present invention, or a pharmaceutically acceptable salt thereof, or a pharmaceutically acceptable solvate of either entity, in the manufacture of a medicament for administration to a human for the treatment of a medical condition capable of being treated by the inhibition of PDE1 activity.

The present invention also provides the use of a compound of the present invention, or a veterinarily acceptable salt thereof, or a veterinarily acceptable solvate of either entity, in the manufacture of an animal medicament for the treatment of a medical condition capable of being treated by the inhibition of PDE1 activity.

In yet another aspect, the invention provides the use of a compound of the present invention, or a pharmaceutically acceptable salt thereof, or a pharmaceutically acceptable solvate of either entity, in the manufacture of a medicament for administration to either a human or an animal wherein the medicament is for use as an inhibitor of PDE1.

Moreover, the present invention provides the use of a compound of the present invention, or a pharmaceutically acceptable salt thereof, or a pharmaceutically acceptable solvate containing either entity, in the manufacture of a human medicament for the treatment of any one or more of male erectile dysfunction, female sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility.

The present invention also provides the use of a compound of the present invention, or a veterinarily acceptable salt thereof, or a veterinarily acceptable solvate containing either entity, in the manufacture of an animal medicament for the treatment of any one or more of male erectile dysfunction, female sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility.

Additionally, the present invention provides a method of treating a medical condition for which a PDE1 inhibitor is required, in a mammal (including a human being), which comprises administering to said mammal a therapeutically effective amount of a compound of the present invention, or a pharmaceutically or veterinarily acceptable salt thereof, or a pharmaceutically or veterinarily acceptable solvate of either entity, or a pharmaceutical composition or veterinary formulation containing any of the foregoing.

Still further, the present invention provides a method of treating any one or more of male erectile dysfunction, female sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility in a mammal (including a human being), which comprises administering to said mammal a therapeutically effective amount of a compound of formula (I) or a pharmaceutically or veterinarily acceptable salt thereof, or a pharmaceutically or veterinarily acceptable solvate of either entity, or a pharmaceutical composition or veterinary formulation containing any of the foregoing.

References to treatment (as well as treating) include any one or more of curative, palliative or prophylactic treatment of a disease or condition.

The compounds of the formula (I) can be prepared by novel routes or, alternatively, by conventional routes.

The compounds of the present invention may be prepared by any one of the synthesis processes presented in the Route Section (infra), or by any one of the more specific synthesis protocols presented in the Examples Section (infra)—which are presented as either Preparations or Examples. The present invention also encompasses any one or more of these processes, including any of the steps thereof, in addition to any novel intermediate(s) obtained therefrom or used therein.

The general syntheses of the compounds of the present invention are now presented in the following Route Section.

It is to be noted that in the following Route Section that a propyl group has been used as an example of a suitable $R_a$ group. Naturally, compounds with other $R_a$ groups may be used to prepare compounds of the present invention. Likewise, suitable substituents other than those presented for $R_1$ etc. may be used.

Route Section

Route A

A compound of formula (I) may be obtained from a compound of formula (II) wherein

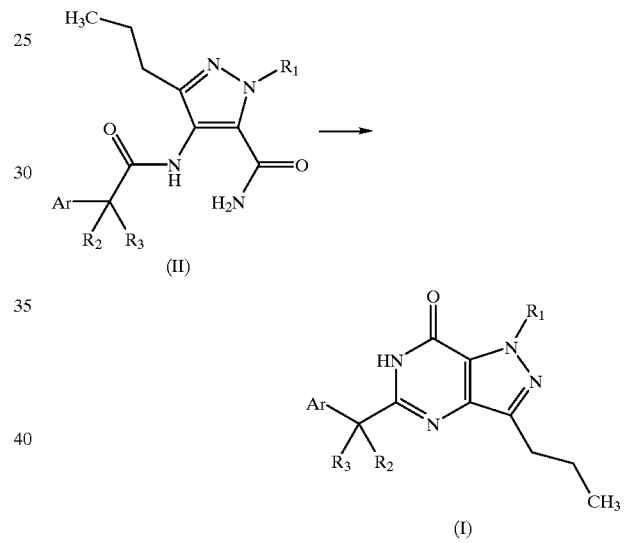

$R_{1-3}$ and Ar are as previously defined for formula (I), by the application of known cyclisation methods for pyrimidinone ring formation. Thus, for example, the cyclisation may be effected by the treatment of (II) with a base such as sodium or potassium hydroxide, or sodium or potassium carbonate, optionally in the presence of hydrogen peroxide, in a $C_1$ to $C_4$ alcohol-water medium, at from about 50° C. to the reflux temperature of the reaction mixture.

The cyclisation may also be mediated by a sodium or potassium $C_1$ to $C_5$ alkoxide, in a $C_1$ to $C_4$ alcohol solvent, at from about 50° C. to the reflux temperature of the reaction mixture.

Alternative cyclisation procedures involve the treatment of (II) with either polyphosphoric acid at from about 130° C. to about 150° C. or with anhydrous zinc chloride at from about 200° C. to about 220° C.

In certain examples, the Ar group contains substituents which are chemically reactive under the cyclisation conditions and further reaction takes place under the standard conditions e.g. an alkyl bromide may hydrolyse to an alcohol and a trifluoromethyl group or an ester group may be converted to a carboxylic acid.

By way of example, a preferred embodiment of the above-mentioned route is as follows:

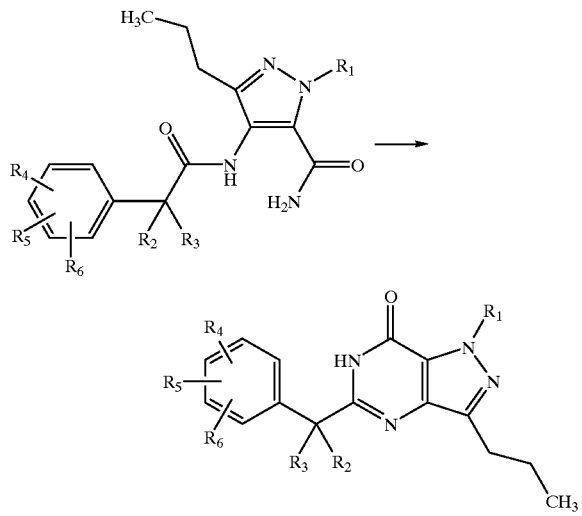

wherein the each of the groups are as defined above.

Route B

Compounds of the formula (I) in which $R_4$ is $NH_2$ can be prepared from the corresponding nitrobenzene by a reductive method.

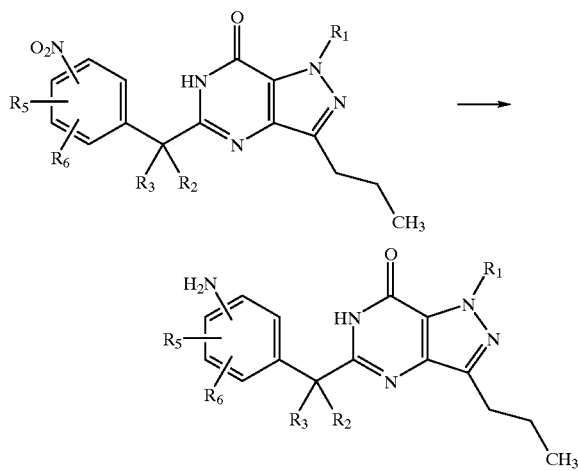

wherein each of the other groups are as defined above.

In a typical procedure the reduction is carried out by catalytic hydrogenation e.g. using either a heterogeneous catalyst such as palladium, palladium- or rhodium-on-carbon, Raney nickel, or a homogeneous catalyst e.g. tris(triphenylphosphine)chlororhodium, in a suitable organic solvent e.g. industrial methylated spirit or ethyl acetate. The reaction is preferably carried out at from room temperature to the reflux temperature of the solvent and a pressure of from 1 to 5 atmospheres (100–500 kPa).

The reaction can also be carried out using an excess of an electron transfer reducing agent such as tin (II) chloride in a suitable solvent such as a $C_1$ to $C_4$ alcohol e.g. ethanol, at the reflux temperature of the reaction mixture.

Route C

Compounds of the formula (I) in which $R_4$ is a group of the formula —$NR_7SO_2X$, wherein $R_7$ and X are as defined above, can be prepared by reaction of a compound of formula (I), where $R_4$ is $NHR_7$ with an appropriate alkyl sulphonyl halide.

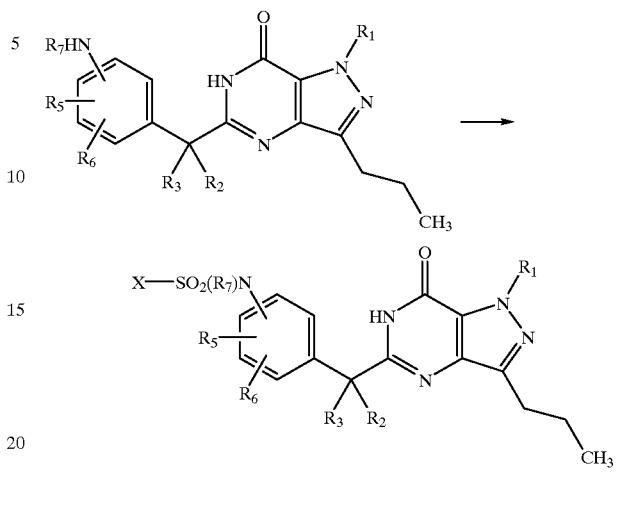

Here, each of the groups are as defined above.

Similarly, compounds of the formula (I) in which $R_4$ is $NR_7COX$ can be prepared by acylation of the same starting material with an appropriate acid chloride or anhydride. Compounds in which $R_4$ is $NR_7CHO$ may also be prepared from a mixed anhydride such as ($C_1$–$C_4$ alkylCO)OCHO.

The reaction may be carried out in a suitable inert solvent such as dichloromethane in the presence of an acid acceptor such as triethylamine or pyridine (which can also be used as the solvent), at a temperature of from 0° C. to the reflux temperature of the solvent, preferably at room temperature.

Compounds of the formula (I) in which $R_4$ is a group of the formula —$NR_7CHO$ can also be prepared using a formyl transfer agent such as formyl- or 1,2-diformylhydrazine. In this case the reaction is preferentially carried out in the absence of solvent at the reflux temperature of the formylating agent.

Route D

Compounds of the formula (I) in which $R_4$ is a group of the formula ($C_{1-4}$ alkyl)$R_7N$— may be prepared by reduction of compounds of the formula (I) in which $R_4$ is $NR_7CO(C_{1-3}$ alkyl), wherein $R_7$ is H or ($C_{1-4}$ alkyl).

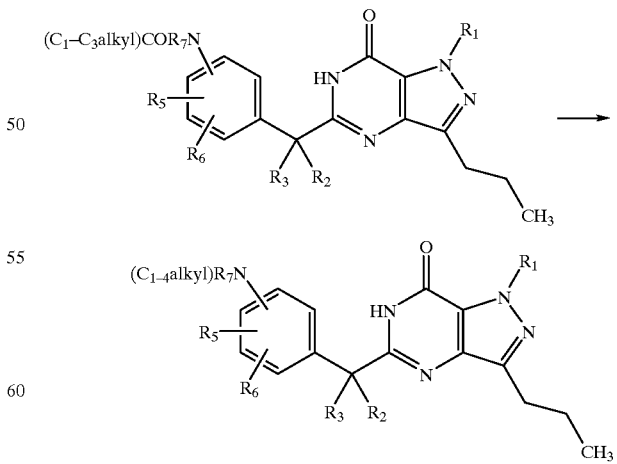

Here, each of the groups are as defined above.

The reducing agent is selected from reagents such as lithium aluminium hydride and diborane and is preferentially carried out in an inert solvent such as tetrahydrofuran at a temperature from room temperature to the reflux temperature of the solvent.

Alternatively, the products may be prepared by reduction of an imine ($R_4$ is N=CH—($C_{1-3}$ alkyl)) or iminium ion ($R_4$ is [$NR_7$=CH—($C_{1-3}$ alkyl)]$^+$) which may optionally be isolated. The reducing agent may be sodium acetoxyborohydride or sodium cyanohydride. The reaction may also be carried out using catalytic hydrogenation using a catalyst such as palladium-on-charcoal.

Route E

Compounds of the formula (I) in which $R_4$ is nitro can be prepared by nitration of the corresponding benzene derivative. The reaction is preferentially carried out using mixtures of concentrated nitric and sulphuric acids at a temperature from 0° C. to 100° C.

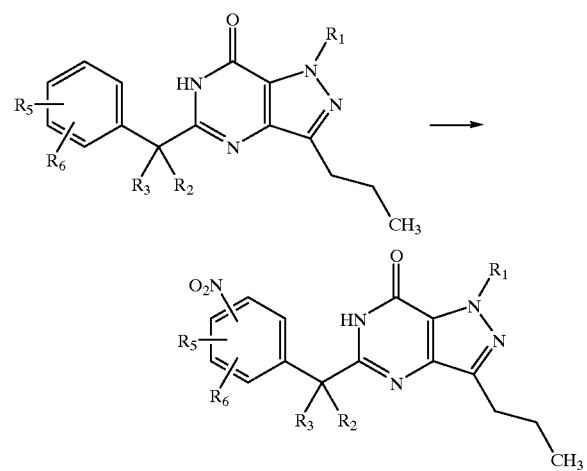

Here, each of the groups are as defined above

Similarly, compounds in which $R_4$ is chlorosulphonyl can be prepared by chlorosulphonylation of the corresponding benzene derivative. The reaction is preferentially carried out using chlorosulphonic acid as the solvent at a temperature from 0° C. to 100° C.

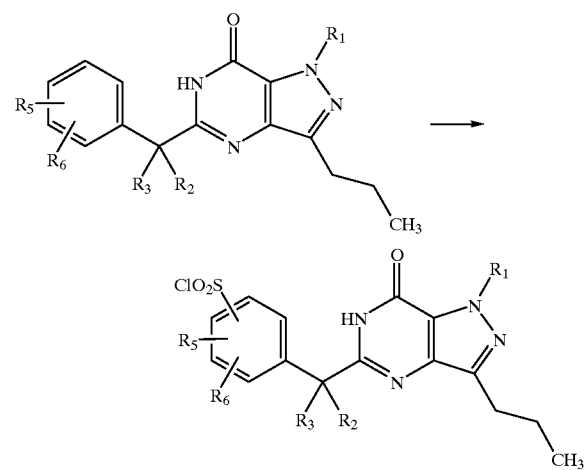

With this route you may get a mixture of regio-isomers.

Route F

When Ar is a bicyclic group, a hetero-ring fused to the benzo portion can be formed using conventional ring forming reactions. For example, when the fused ring is a pyridone, the ring is formed by treatment of the corresponding b-ethoxypropenamide with a strong acid such as sulphuric or hydrochloric acid.

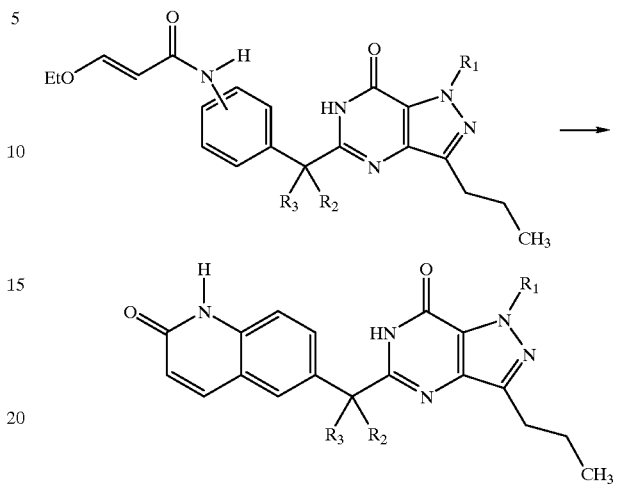

Here, each of the groups are as defined above

Route G

Compounds of the formula (I) in which $R_4$ is a sulphamido or aminoalkanesulphonamido group can be prepared by treatment of the corresponding sulphamoyl halide or haloalkanesulphonamide with an excess of the amine in an aqueous or alcoholic solvent at a temperature of from room temperature to the reflux temperature of the solvent. By way of example:

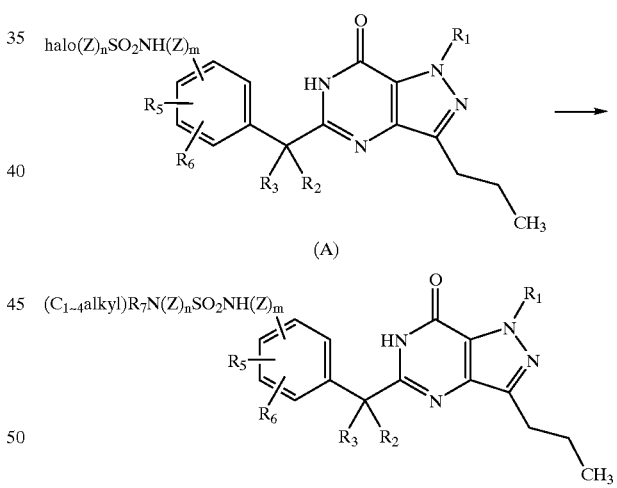

Here, each of the groups are as defined above, and m and n are independently selected from 0 and 1.

A compound of formula (A) where n is 1 and m is 0 or 1 can be cyclised to give the corresponding cyclic sultam. The reaction is carried out using a strong base such as sodium hydride in an inert solvent such as dimethylformamide at a temperature from 0° C. to room temperature.

Route H

Compounds of the formula (I) in which $R_4$ is an aminosulphonyl group can be prepared from the corresponding chlorosulphonyl derivative —$SO_2Cl$ by treatment with an appropriate amine, optionally in excess, in an aqueous or alcoholic solvent, at a temperature of from room temperature to the reflux temperature of the solvent. For example:

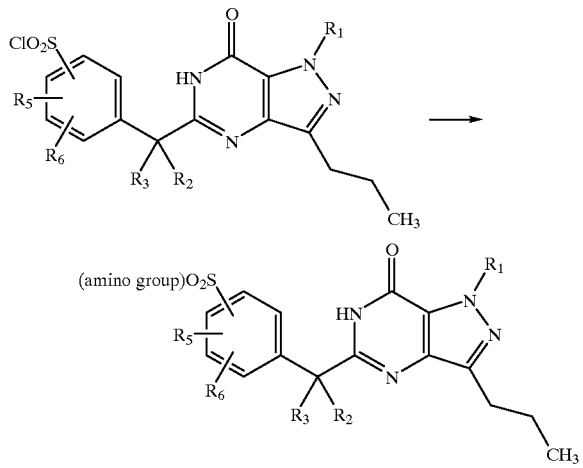

Similarly, when the chlorosulphonyl derivative is treated with aqueous alkali such as sodium hydroxide, a compound of the formula (I) in which $R_4$ is a group of the formula —$SO_3H$ can be obtained.

Route I

Compounds of the formula (I) in which $R_4$ is a -G-Het group wherein G is a direct link and Het is attached to the adjacent phenyl ring by a nitrogen atom e.g. imidazol-1-yl can be prepared from the corresponding halophenyl derivative, where halo is preferably bromo or iodo, and the heterocycle. The reaction is preferably carried out in the presence of a base such as potassium carbonate, and a copper catalyst, preferably copper bronze. The reaction can be carried out in a high boiling solvent such as dimethylformamide, dimethylacetamide or N-methyl-2-pyrrolidinone at the reflux temperature of the solvent, or alternatively may be carried out without solvent, at the melt temperature of the mixture.

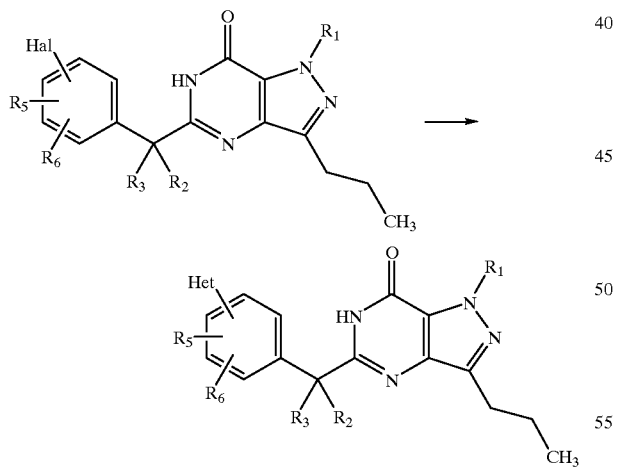

Route J

Compounds of the formula (I) in which the groups $R_3$ to $R_6$ contain a hydroxy or carboxyl function can be prepared from the corresponding ether or ester under conventional hydrolytic conditions. Ethers are preferably hydrolysed under strongly acidic conditions such as using concentrated hydrobromic acid at a temperature of between 100° C. and 150° C. Ester hydrolysis is preferably carried out under basic conditions, for example using sodium or potassium hydroxide as base, optionally in the presence of hydrogen peroxide, in water or an alcoholic solvent such as ethanol. The reaction is carried out at from room temperature to the reflux temperature of the solvent.

Route K

Compounds of the formula (I) in which the groups $R_2$ and $R_3$ together form a carbonyl function are preferably prepared from the corresponding secondary alcohol by an oxidative method. The preferred oxidant is pyridinium chlorochromate and the reaction is preferably carried out in an inert solvent such as dichloromethane at room temperature.

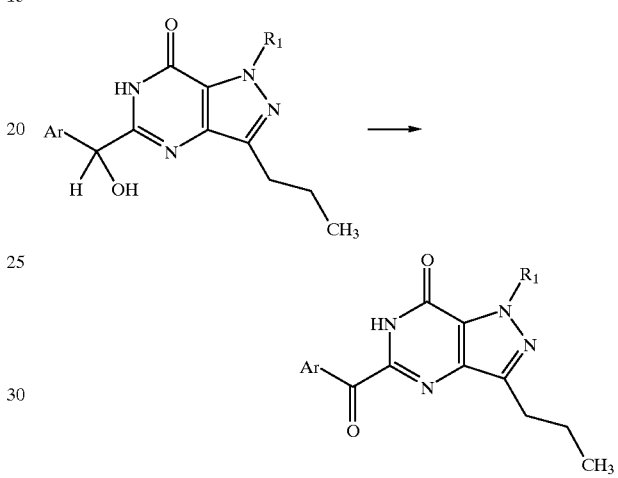

An intermediate of the formula (II) is prepared by reaction of a carboxylic acid chloride, which may be derived by treatment of the corresponding carboxylic acid with oxalyl chloride in dichloromethane in the presence of a catalytic quantity of dimethylformamide, with an aminopyrazole derivative of the formula (III). The preparation of (III) is conventional—for example see the teachings of U.S. Pat. No. 5,272,147.

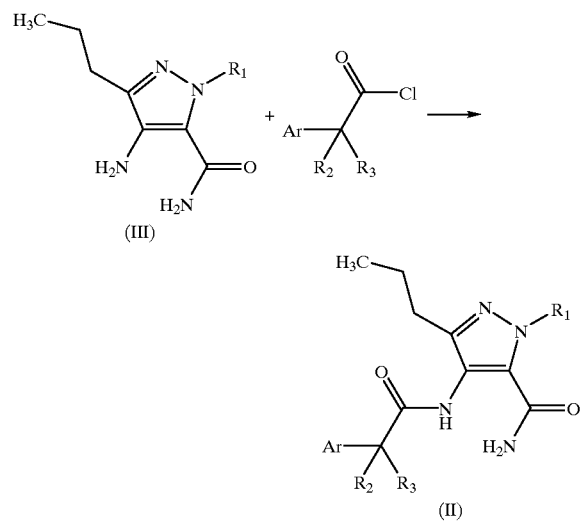

17

The reaction is carried out in a suitable inert solvent such as dichloromethane in the presence of an acid acceptor such as triethylamine or in a basic solvent such as pyridine, at a temperature of from 0° C. to the reflux temperature of the solvent, preferably at room temperature.

Interconversion of functional groups may also be carried out using a compound of the formula (II). Thus, for example, when $R_4$ is bromomethyl, the halide can be displaced by an appropriate amine preferably used in excess. Similarly the bromomethyl derivative can be reacted with an alcohol to provide an ether derivative, preferably using a metal salt such as silver nitrate. The alcohol is generally used as solvent and the reaction is preferably carried out at room temperature. For example:

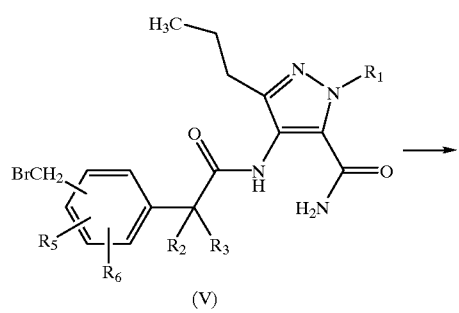

(V)

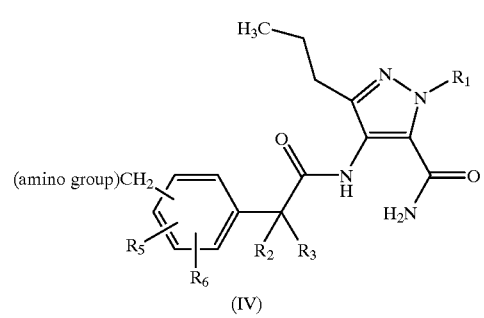

(IV)

The present invention will now be discussed only by way of further examples. The following Examples Section provides illustrations of the preparation of the compounds (I). The following Preparations Section provides illustrations of the preparation of inter alia novel starting materials.

In these sections, the $^1$H nuclear magnetic resonance (NMR) spectra were recorded using either a Varian Unity 300 or a Varian Inova 400 spectrometer and were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; b, broad.

The mass spectra (m/z) were recorded using a Fisons Instruments Trio mass spectrometer in the thermospray ionisation mode. In the following sections, room temperature means 20 to 25° C.

In the following examples, propyl means n-propyl unless otherwise stated.

18

SYNTHESIS EXAMPLES

Example 1

5-(4-bromobenzyl)-1-methyl-3-propyl-6,7-dihydro-1H-pyrazolo[4,3-d]pyrimidin-7-one

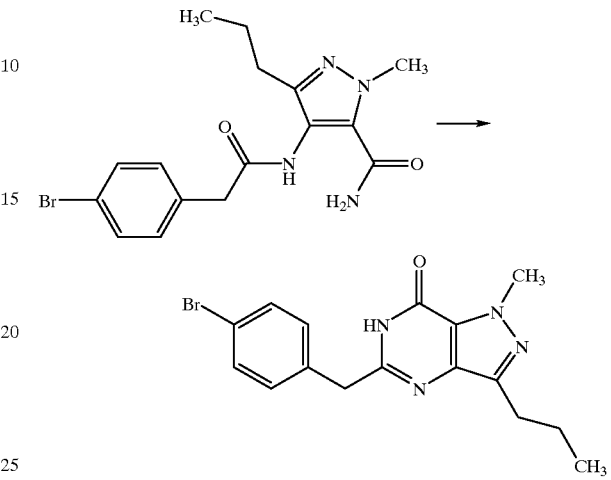

A 30% w/w solution of hydrogen peroxide (27 ml, 0.238 mol) was added to a solution of sodium hydroxide (7.24 g, 0.181 mol) in water (400 ml). A solution of N-(5-carbamoyl-1-methyl-3-propyl-1H-4-pyrazolyl)-2-(4-bromophenyl)acetamide (29.0 g, 0.076 mol) in ethanol (350 ml) was then added, and the reaction stirred at reflux for 3 hours.

On cooling, the solution was diluted with water (200 ml) and acidified to pH5 with 2N aqueous hydrochloric acid solution. The resulting white precipitate was extracted into dichloromethane (2×250 ml). The organic extracts were dried ($MgSO_4$), filtered and concentrated under reduced pressure to give the title compound as a colourless solid. Crystallisation from acetonitrile gave colourless needles (19.33 g), m.p. 193–194° C.

Found: C, 53.09; H, 4.72; N, 15.41; $C_{16}H_{17}BrN_4O$ requires C, 53.19; H, 4.74; N, 15.51%.

$^1$H-NMR (DMSO-$d_6$): δ=0.90 (t, 3H), 1.65 (m, 2H), 2.70 (t, 2H), 3.85 (s, 2H), 4.10 (s, 3H), 7.25 (d, 2H), 7.45 (d, 2H), 12.30 (s, 1H) ppm.

Examples 2 to 24

The compounds of the following tabulated Examples of the general formula:

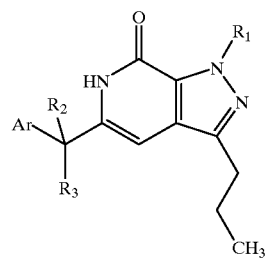

were prepared from the corresponding carboxamide using similar methods to that used in Example 1.

| Ex. No. | R₁ | Ar(R₂)(R₃)C— | Analysis/¹H-NMR/Melting Point/Crystallisation solvent |
|---|---|---|---|
| 2 | —CH₃ | 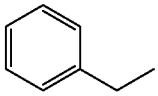 | Found: C, 68.24; H, 6.47; N, 20.04%. C₁₆H₁₈N₄O, requires C, 68.06; H, 6.43; N, 19.85%. ¹H-NMR (DMSO-d₆): δ=0.90(t, 3H), 1.70(m, 2H), 2.70(t, 2H), 3.90(s, 2H), 4.10(s, 3H), 7.20–7.40(m, 5H), 12.30(s, 1H) ppm. Melting point: 200–202° C. Crystallisation solvent: ethanol. |
| 3 | —CH₂CH₃ | 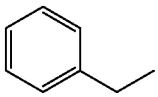 | Found: C, 68.58; H, 6.80; N, 18.82%. C₁₇H₂₀N₄O, requires C, 68.89; H, 6.80; N, 18.91%. ¹H-NMR (CDCl₃): δ=1.05(t, 3H), 1.55(t, 3H), 1.90(m, 2H), 2.95(t, 2H), 4.10(s, 2H), 4.65(q, 2H), 7.30–7.50(m, 5H), 10.00(s, 1H) ppm. Melting point: 171–173° C. Crystallisation solvent: methanol. |
| 4 | —CH₃ | 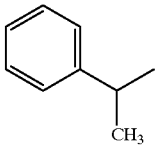 | Found: C, 68.85; H, 6.79; N, 18.87%. C₁₇H₂₀N₄O, requires C, 68.89; H, 6.80; N, 18.91%. ¹H-NMR (CDCl₃): δ=1.05(t, 3H), 1.75(d, 3H), 1.90(m, 2H), 2.95(t, 2H), 4.15(q, 1H), 4.25(s, 3H), 7.30–7.40(m, 5H), 9.15(s, 1H) ppm. Melting point: 154–157° C. Crystallisation solvent: hexane. |
| 5 | —CH₃ | 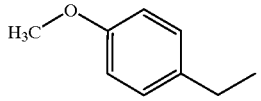 | Found: C, 65.00; H, 6.26; N, 17.58%. C₁₇H₂₀N₄O₂, requires C, 65.36; H, 6.45; N, 17.94%. ¹H-NMR (CDCl₃): δ=1.05(t, 3H), 1.85(m, 2H), 2.95(t, 2H), 3.83(s, 3H), 4.03(s, 2H), 4.23(s, 3H), 6.90 (d, 2H), 7.30(d, 2H), 9.55(s, 1H) ppm. Melting point: 195–198° C. Crystallisation solvent: ethyl acetate. |
| 6 | —CH₃ | 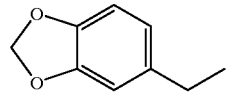 | Found: C, 62.30; H, 5.46; N, 17.02%. C₁₇H₁₈N₄O₃, requires C, 62.56; H, 5.56; N, 17.17%. ¹H-NMR (DMSO-d₆): δ=0.90(t, 3H), 1.70(m, 2H), 2.70(t, 2H), 3.75(s, 2H), 4.10(s, 3H), 5.95(s, 2H), 6.70–6.95(m, 3H), 12.15(s, 1H) ppm. Melting point: 204–206° C. Crystallisation solvent: ethanol. |
| 7 | —CH₃ | 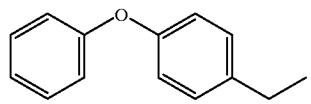 | Found: C, 70.38; H, 5.85; N, 14.96%. C₂₂H₂₂N₄O₂, requires C, 70.57; H, 5.92; N, 14.96%. ¹H-NMR (CDCl₃): δ=1.05(t, 3H), 1.85(m, 2H), 2.95(t, 2H), 4.05(s, 2H), 4.25(s, 3H), 7.00(m, 4H), 7.15 (m, 1H), 7.35(m, 4H), 9.75(s, 1H) ppm. Melting point: 167–168° C. Crystallisation solvent: acetonitrile. |
| 8 | —CH₃ | 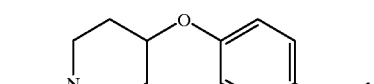 | Found: C, 66.58; H, 7.26; N, 17.73%. C₂₂H₂₉N₅O₂, requires C, 66.81; H, 7.39; N, 17.71%. ¹H-NMR (CDCl₃): δ=1.05(t, 3H), 1.85(m, 4H), 2.00(br. m, 2H), 2.35 (br. m, 5H), 2.70(br. m, 2H), 2.90(t, 2H), 4.00(s, 2H), 4.25(s, 3H) 4.35(br. m, 1H), 6.90(d, 2H), 7.25(d, 2H), 9.30(s, 1H) ppm. Melting point: 194–195° C. Crystallisation solvent: acetonitrile. |

-continued

| Ex. No. | $R_1$ | $Ar(R_2)(R_3)C-$ | Analysis/$^1$H-NMR/Melting Point/Crystallisation solvent |
|---|---|---|---|
| 9 | —CH$_3$ | 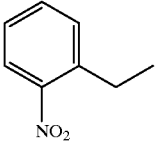 | Found: C, 58.54; H, 5.28; N, 21.93 %. $C_{16}H_{17}N_5O_3$, requires C, 58.70; H, 5.23; N, 21.40%. $^1$H-NMR (DMSO-d$_6$): δ=0.75(t, 3H), 1.55(m, 2H), 2.55(t, 2H), 4.05(s, 3H), 4.35(s, 2H), 7.55(m, 2H), 7.70 (m, 1H), 8.05(d, 1H) 12.35(s, 1H) ppm. Melting point: 217–222° C. Crystallisation solvent: ethyl acetate. |
| 10 | —CH$_3$ | 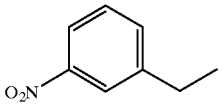 | Found: C, 58.44; H, 5.24; N, 21.30%. $C_{16}H_{17}N_5O_3$, requires C, 58.70; H, 5.23; N, 21.40%. $^1$H-NMR (DMSO-d$_6$): δ=0.85(t, 3H), 1.65(m, 2H), 2.70(t, 2H), 4.05(s, 5H), 7.60(t, 1H), 7.80(d, 1H), 8.10 (d, 1H), 8.25(s, 1H), 12.35(s, 1H) ppm. Melting point: 230–233° C. Crystallisation solvent: ethyl acetate/ methanol. |
| 11 | —CH$_3$ | 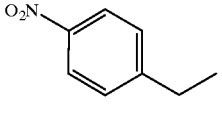 | Found: C, 58.46; H, 5.03; N, 21.08%. $C_{16}H_{17}N_5O_3$, requires C, 58.70; H, 5.23; N, 21.40%. $^1$H-NMR (CDCl$_3$): δ=1.05(t, 3H), 1.85(m, 2H), 2.95(t, 2H), 4.20(s, 2H), 4.30(s, 3H), 7.60(d, 2H), 8.20 (d, 2H), 11.35(s, 1H) ppm. Melting point: 225–226° C. Crystallisation solvent: ethyl acetate. |
| 12 | —CH$_3$ |  | Found: C, 53.07; H, 4.76; N, 15.15%. $C_{16}H_{17}BrN_4O$, requires C, 53.19; H, 4.74; N, 15.51%. $^1$H-NMR (DMSO-d$_6$): δ=0.90(t, 3H), 1.60(m, 2H), 2.60(t, 2H), 4.05(s, 2H), 4.10(s, 3H), 7.20(m, 2H), 7.35 (d, 1H), 7.60(d, 1H), 12.35(s, 1H) ppm. Melting point: 200–202° C. Crystallisation solvent: acetonitrile. |
| 13 | —CH$_3$ | 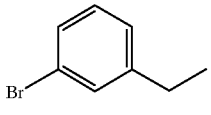 | Found: C, 53.40; H, 4.82; N, 15.37%. $C_{16}H_{17}BrN_4O$, requires C, 53.19; H, 4.74; N, 15.51%. $^1$H-NMR (DMSO-d$_6$): δ=0.90(t, 3H), 1.70(m, 2H), 2.70(t, 2H), 3.90(s, 2H), 4.10(s, 3H), 7.30(m, 2H), 7.40 (d, 1H), 7.55(s, 1H), 12.30(s, 1H) ppm. Melting point: 233–235° C. Crystallisation solvent: ethanol. |
| 14 | —CH$_3$ | 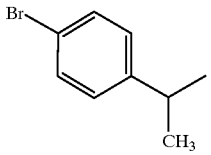 | Found: C, 54.02; H, 5.15; N, 14.91%. $C_{17}H_{19}BrN_4O$, requires C, 54.41; H, 5.10; N, 14.93%. $^1$H-NMR (CDCl$_3$): δ=1.05(t, 3H), 1.75(d, 3H), 1.90(m, 2H), 2.95(t, 2H), 4.10(q, 1H), 4.25(s, 3H), 7.23 (d, 2H), 7.50(d, 2H), 9.50(s, 1H) ppm. Melting point: 167–169° C. Crystallisation solvent: ethyl acetate/ hexane. |
| 15 | —CH$_3$ | 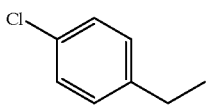 | Found: C, 60.57; H, 5.39; N, 17.48%. $C_{16}H_{17}ClN_4O$, requires C, 60.66; H, 5.41; N, 17.69%. $^1$H-NMR (DMSO-d$_6$): δ=0.90(t, 3H), 1.70(m, 2H), 2.70(t, 2H), 3.90(s, 2H), 4.07(s, 3H), 7.35(m, 4H), 12.30 (s, 1H) ppm. Melting point: 189–191° C. Crystallisation solvent: acetonitrile. |

-continued

| Ex. No. | R₁ | Ar(R₂)(R₃)C— | Analysis/¹H-NMR/Melting Point/Crystallisation solvent |
|---|---|---|---|
| 16 | —CH₃ | 2-(trifluoromethyl)phenyl-CH₂CH₂— | Found: C, 58.62; H, 4.98; N, 16.06%. $C_{17}H_{17}F_3N_4O$, requires C, 58.28; H, 4.89; N, 15.99%. ¹H-NMR (CDCl₃): δ=1.05(t, 3H), 1.85(m, 2H), 2.90(t, 2H), 4.20(s, 3H), 4.30(s, 2H), 7.45(m, 2H), 7.55(m, 1H), 7.75(d, 1H), 9.10(s, 1H) ppm. Melting point: 195–196° C. Crystallisation solvent: ethyl acetate. |
| 17 | —CH₃ | 4-(trifluoromethyl)phenyl-CH₂CH₂— | Found: C, 58.54; H, 4.91; N, 16.27%. $C_{17}H_{17}F_3N_4O$, requires C, 58.28; H, 4.89; N, 15.99%. ¹H-NMR (DMSO-d₆): δ=0.91(t, 3H), 1.08(m, 2H), 2.68(t, 2H), 4.00(s, 2H), 4.09(s, 3H), 7.52(d, 2H), 7.68(d, 2H), 12.32(s, 1H) ppm. Melting point: 209.5–211° C. Crystallisation solvent: ethyl acetate/hexane. |
| 18 | —CH₃ | 4-isopropylphenyl-CH₂CH₂— | Found: C, 70.06; H, 7.38; N, 17.28%. $C_{19}H_{24}N_4O$, requires C, 70.34; H, 7.46; N, 17.27%. ¹H-NMR (DMSO-d₆): δ=0.90(t, 3H), 1.15(d, 6H), 1.70(m, 2H), 2.70(m, 2H), 2.80(m, 1H), 3.85(s, 2H), 4.05(s, 3H), 7.20(m, 4H), 12.25(s, 1H) ppm. Melting point: 209–210° C. Crystallisation solvent: ethyl acetate. |
| 19 | —CH₃ | 4-(ethoxymethyl)phenyl-CH₂CH₂— | Found: C, 67.27; H, 7.10; N, 16.38%. $C_{19}H_{24}N_4O_2$, requires C, 67.03; H, 7.11; N, 16.38%. ¹H-NMR (CDCl₃): δ=1.05(t, 3H), 1.25(t, 3H), 1.85(m, 2H), 2.95(t, 2H), 2.55(q, 2H), 4.05(s, 2H), 4.25(s, 3H), 4.50(s, 2H), 7.35(s, 4H), 9.80(s, 1H) ppm. Melting point: 176–177° C. |
| 20 | —CH₃ | 4-acetylphenyl-CH₂CH₂— | Found: C, 66.42; H, 6.17; N, 17.11%. $C_{18}H_{20}N_4O_2$, requires C, 66.65; H, 6.22; N, 17.27%. ¹H-NMR (CDCl₃): δ=1.05(t, 3H), 1.85(m, 2H), 2.63(s, 3H), 2.95(t, 2H), 4.15(s, 2H), 4.25(s, 3H), 7.50(d, 2H), 7.95(d, 2H), 9.75(s, 1H) ppm. Melting point: 209–210° C. Crystallisation solvent: ethyl acetate. |
| 21 | —CH₃ | 4-(dimethylaminomethyl)phenyl-CH₂CH₂— | Found: C, 67.31; H, 7.52; N, 20.31%. $C_{19}H_{25}N_5O$, requires C, 67.23; H, 7.42; N, 20.63%. ¹H-NMR (CDCl₃): δ=1.05(t, 3H), 1.85(m, 2H), 2.25(s, 6H), 2.95(t, 2H), 3.65(s, 2H), 4.05(s, 2H), 4.25(s, 3H), 7.30(m, 4H), 9.30(br. s, 1H) ppm. Melting point: 196–198° C. Crystallisation solvent: ethyl acetate. |
| 22 | —CH₃ | 4-(morpholinomethyl)phenyl-CH₂CH₂— | Found: C, 66.17; H, 7.17; N, 18.26%. $C_{21}H_{27}N_5O_2$, requires C, 66.12; H, 7.13; N, 18.36%. ¹H-NMR (CDCl₃): δ=1.05(t, 3H), 1.85(m, 2H), 2.45(br, m, 4H), 2.95(t, 2H), 3.50(s, 2H), 3.75(m, 4H), 4.10(s, 2H), 4.25(s, 3H), 7.35(m, 4H), 9.35(s, 1H) ppm. Melting point: 191–193° C. Crystallisation solvent: ethyl acetate/hexane. |

| Ex. No. | $R_1$ | $Ar(R_2)(R_3)C-$ | Analysis/$^1$H-NMR/Melting Point/Crystallisation solvent |
|---|---|---|---|
| 23 | —CH$_3$ | (4-(imidazol-1-ylmethyl)phenyl)ethyl | Found: C, 66.56; H, 6.24; N, 23.09%. $C_{20}H_{22}N_6O$, requires C, 66.28; H, 6.12; N, 23.19%. $^1$H-NMR (DMSO-d$_6$): δ=0.90(t, 3H), 1.70(m, 2H), 2.70(t, 2H), 3.85(s, 2H), 4.05(s, 3H), 5.15(s, 2H), 6.85 (s, 1H), 7.05–7.30(m, 5H), 7.70(s, 1H), 12.25(s, 1H) ppm. Melting point: 191–193° C. Crystallisation solvent: acetonitrile. |
| 24 | —CH$_3$ | (4-bromo-2-nitrophenyl)ethyl | Found: C, 47.27; H, 3.92; N, 17.16%. $C_{16}H_{16}BrN_5O_3$, requires C, 47.30; H, 3.97; N, 17.24%. $^1$H-NMR (DMSO-d$_6$): δ=0.80(t, 3H), 2.55(m, 2H), 2.55(t, 2H), 4.05(s, 3H), 4.30(s, 2H), 7.50(d, 1H), 7.95 (d, 1H), 8.25(s, 1H), 12.35(s, 1H) ppm. Melting point: 229–231° C. Crystallisation solvent: ethyl acetate. |

Example 25

5-(4-hydroxymethylbenzyl)-1-methyl-3-propyl-6,7-dihydro-1H-pyrazolo[4,3-d]pyrimidin-7-one

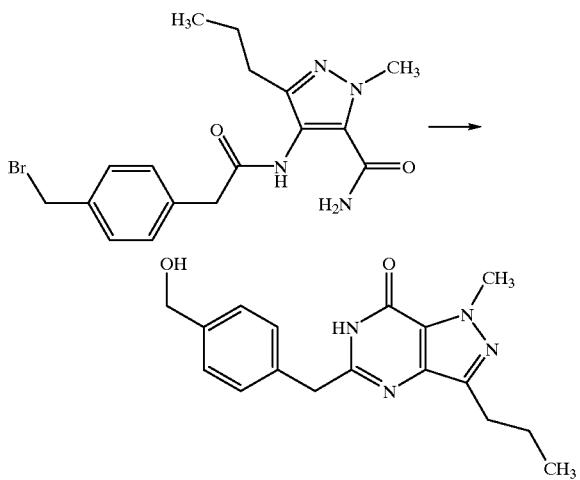

Aqueous hydrogen peroxide (0.24 ml, 30% w/w, 0.0021 mol) was added to a solution of sodium hydroxide (180 mg, 0.0045 mol) in water (10 ml). A solution of N-(5-carbamoyl-1-methyl-3-propyl-1H-pyrazolyl)-2-(4-bromomethylphenyl)acetamide (400 mg, 0.001 mol) in dioxan (5 ml) was then added and the mixture stirred at 90° C. for 4 hours. On cooling, the reaction mixture was concentrated under reduced pressure, the residue dissolved in water (10 ml) and acidified to pH 5 with 1N aqueous hydrochloric acid. This solution was then extracted with dichloromethane (2×20 ml), the combined organic extracts dried (MgSO$_4$), filtered and evaporated under reduced pressure.

Purification by flash column chromatography, eluting with dichloromethane:methanol (96:4 by volume), followed by trituration with diethyl ether/pentane gave the title compound as a solid (60 mg), m.p.215–218° C.

Found: C, 65.14; H, 6.42; N, 17.88; $C_{17}H_{20}N_4O_2$, requires C, 65.36; H, 6.45; N, 17.94%.

$^1$H-NMR (CDCl$_3$): δ=1.07 (t, 3H), 1.86 (m, 3H), 2.92 (t, 2H), 4.08 (s, 2H), 4.24 (s, 3H), 4.70 (s, 2H), 7.34 (s, 4H), 9.74 (s, 1H) ppm.

Example 26

5-(2-methoxybenzyl)-1-methyl-3-propyl-6,7-dihydro-1H-pyrazolo[4,3-d]pyrimidin-7-one

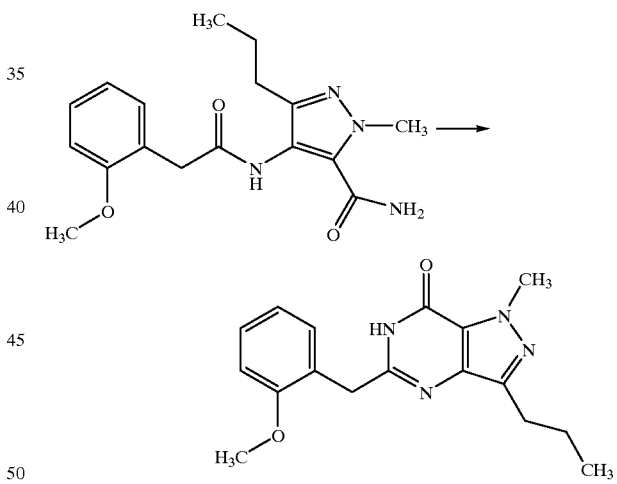

N-(5-carbamoyl-1-methyl-3-propyl-1H-4-pyrazolyl)-2-(2-methoxyphenyl)acetamide (750 mg, 0.00228 mol) was suspended in polyphosphoric acid (10 ml) and heated under nitrogen at 150° C. for 4 hours. On cooling, the solution was added to ice and the pH adjusted to 5 with aqueous 10N sodium hydroxide solution. The aqueous phase was extracted with dichloromethane (3×10 ml), the organic extracts combined, dried (MgSO$_4$), filtered and concentrated under reduced pressure.

Purification by flash column chromatography, eluting with dichloromethane:methanol (98:2, by volume), followed by trituration with hexane gave the title compound as a white solid, m.p.162–163° C.

Found: C, 65.11; H, 6.41; N, 17.83; $C_{17}H_{20}N_4O_2$ requires C, 65.39; H, 6.45; N, 17.94%.

¹H-NMR (CDCl₃): δ=1.05 (t, 3H), 1.85 (m, 2H), 2.90 (t, 2H), 400 (s, 3H), 4.05 (s, 2H), 4.20 (s, 3H), 7.00 (m, 2H), 7.35 (m, 2H), 9.50 (s, 1H) ppm.

Examples 27 to 29

The compounds of the following tabulated examples of the general formula:

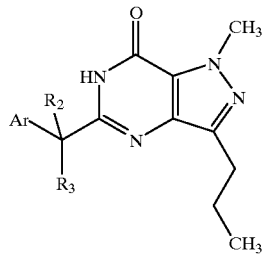

were prepared by reaction of the corresponding pyrazole-carboxamides by similar methods to that used in Example 26.

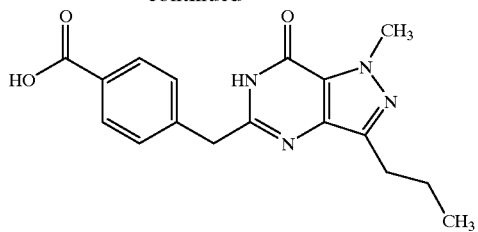

N-(5-carbamoyl-1-methyl-3-propyl-1H-4-pyrazolyl)-2-(4-trifluoromethylphenyl)acetamide (250 mg, 0.00068 mol) was suspended in polyphosphoric acid (4 ml) and heated at 150° C. for 4 hours under a nitrogen atmosphere. On cooling, the reaction mixture was neutralised with 1N aqueous sodium hydroxide solution (10 ml) and extracted with dichloromethane/methanol (40 ml). The combined organic

| Ex. No. | Ar(R₂)(R₃)C— | Analysis/¹H-NMR/Melting Point/Crystallisation solvent |
|---|---|---|
| 27 | (1-phenylpropyl group with H₃C ethyl) | Found: C, 69.37; H, 7.17; N, 17.77%. C₁₈H₂₂N₄O, requires C, 69.65; H, 7.14; N, 18.05%. ¹H-NMR(CDCl₃): δ = 0.95(t, 3H), 1.05(t, 3H), 1.90(m, 2H), 2.05(m, 1H), 2.40(s, 1H), 2.95(t, 2H), 3.80(t, 1H), 4.30(s, 3H), 7.20–7.45(m, 5H), 10.15(s, 1H)ppm. Melting point: 174–175° C. Crystallisation solvent:ethyl acetate/hexane. |
| 28 | (1-phenylcyclopropyl group) | Found: C, 70.10; H, 6.57; N, 18.30%. C₁₈H₂₀N₄O, requires C, 70.11; H, 6.54; N, 18.17%. ¹H-NMR(CDCl₃): δ = 1.00(t, 3H), 1.35(m, 2H), 2.85(m, 4H), 3.85(t, 2H), 4.20(s, 3H), 7.45(m, 5H), 8.40(s, 1H)ppm. Melting point: 122–124° C. Crystallisation solvent:ethanol. |
| 29 | (2-phenylpropan-2-yl group with H₃C CH₃) | Found: C, 69.41; H, 7.16; N, 17.65%. C₁₈H₂₂NO, requires C, 69.65; H, 7.14; N, 18.05%. ¹H-NMR(CDCl₃): δ = 1.05(t, 3H), 1.80(s, 6H), 1.90(m, 2H), 2.95 (t, 2H), 4.25(s, 3H), 7.20–7.40(m, 5H), 8.45(s, 1H)ppm. Melting point: 175–178° C. |

Example 30

4-[(1-methyl-7-oxo-3-propyl-6,7-dihydro-1H-pyrazolo[4,3-d]pyrimidin-5-yl)methyl]-benzoic acid

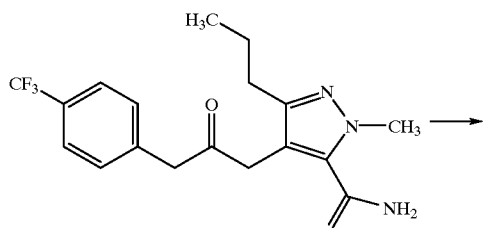

extracts were dried (MgSO₄), filtered and evaporated under reduced pressure. Crystallisation from methanol/ethyl acetate gave the title compound (166 mg), m.p.292–293° C.

Found: C, 60.87; H, 5.50; N, 16.51; C₁₇H₁₈N₄O₃ 0.5H₂O requires C, 60.89; H, 5.71; N, 16.71%.

¹H-NMR (DMSO-d₆): d=0.90 (t, 3H), 1.90 (m, 2H), 2.70 (t, 2H), 4.00 (s, 2H), 410 (s, 3H), 7.40 (d, 2H), 7.85 (d, 2H), 12.35 (s, 1H), 12.90 (br.s, 1H) ppm.

Example 31

5-(3-aminobenzyl)-1-methyl-3-propyl-6,7-dihydro-1H-pyrazolo[4,3-d]pyrimidin-7-one

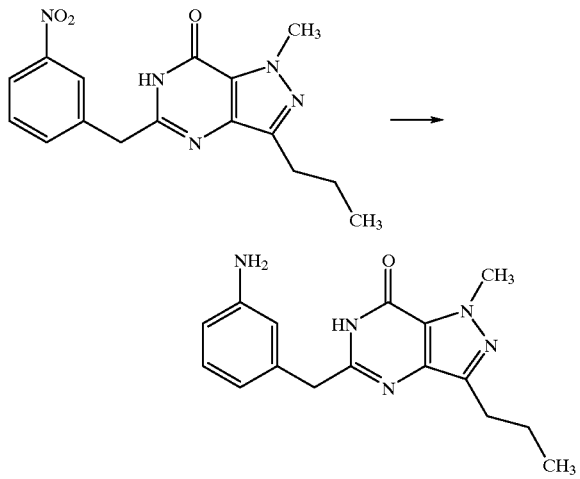

1-Methyl-5-(3-nitrobenzyl)-3-propyl-6,7-dihydro-1H-pyrazolo[4,3-d]pyrimidin-7-one (5.92 g, 0.019 mol) was suspended in industrial methylated spirit (300 ml). Palladium on charcoal (10%, 610 mg) was added and the resulting mixture was hydrogenated at 50 p.s.i and room temperature for 3 hours.

The resulting mixture was then filtered through Arbocel™, washing through with hot ethanol. The filtrate was concentrated under reduced pressure to give, after crystallisation from industrial methylated spirit, the title compound as a solid (5.53 g), m.p.207–210° C.

Found: C, 64.54; H, 6.49; N, 23.09; $C_{16}H_{19}N_5O$, requires C, 64.62; H, 6.44; N, 23.55%.

$^1$H-NMR (DMSO-$d_6$): δ=0.90 (t, 3H), 1.65 (m, 2H), 2.70 (t, 2H), 3.70 (s, 2H), 4.05 (s, 3H), 5.00 (s, 2H), 6.40 (m, 3H), 6.90 (m, 1H), 12.20 (s, 1H) ppm.

Examples 32 and 33

The compounds of the following tabulated Examples of the general formula:

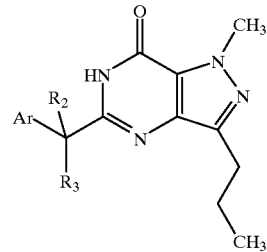

were prepared from the corresponding nitroaromatic compounds by similar methods to that used in Example 31.

| Ex. No. | Ar($R_2$)($R_3$)C— | Analysis/$^1$H-NMR/Melting Point/Crystallisation solvent |
|---|---|---|
| 32 | ![benzyl with 2-NH2] | Found: C, 64.84; H, 6.54; N, 23.71%. $C_{16}H_{19}N_5O$, requires C, 64.62; H, 6.44; N, 23.55%. $^1$H-NMR(DMSO-$d_6$): δ = 0.90(t, 3H), 1.70(m, 2H), 2.70(t, 2H), 3.70(s, 2H), 4.05(s, 3H), 5.30(s, 2H), 6.50(m, 1H), 6.65(d, 1H), 6.95(m, 1H), 7.10(d, 1H), 12.20(s, 1H)ppm. Melting point: 230–231° C. Crystallisation solvent:industrial methylated spirit. |
| 33 | ![benzyl with 4-NH2] | Found: C, 63.40; H, 6.46; N, 22.92%. $C_{16}H_{19}N_5O$, requires C, 64.62; H, 6.44; N, 23.55%. $^1$H-NMR(CDCl$_3$): δ = 1.05(t, 3H), 1.85(m, 2H), 2.90(t, 2H), 3.75(s, 2H), 3.95(s, 2H), 4.25(s, 3H), 6.70(d, 2H), 7.10(d, 2H), 8.95(s, 1H)ppm. Crystallisation solvent:acetone/hexane. |

Example 34

N-{4-[(1-methyl-7-oxo-3-propyl-6,7-dihydro-1H-pyrazolo[4,3-d]pyrimidin-5-yl)methyl]-phenyl}methanesulfonamide

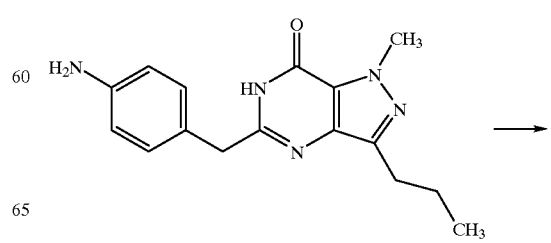

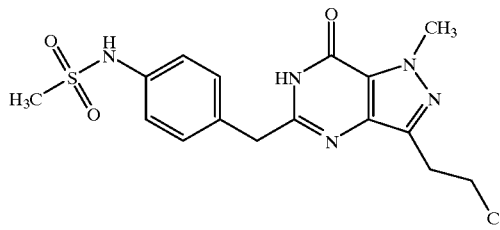

Methanesulfonyl chloride (43 μl, 0.00055 mol) was added to a solution of 5-(4-aminobenzyl)-1-methyl-3-propyl-6,7-dihydro-1H-pyrazolo[4,3-d]pyrimidin-7-one (150 mg, 0.0005 mol) in pyridine (5 ml), and the reaction stirred at room temperature, under a nitrogen atmosphere for 2 hours.

The reaction mixture was partitioned between saturated aqueous sodium carbonate solution (15 ml) and dichloromethane (15 ml), and the aqueous phase extracted with dichloromethane/methanol (50 ml). The organic phases were combined, washed with 1N aqueous hydrochloric acid solution, dried ($MgSO_4$), filtered and concentrated under reduced pressure to give, after recrystallisation from ethyl acetate the title compound as a solid (81 mg), m.p.241–242° C.

Found: C, 54.34; H, 5.79; N, 18.84; $C_{17}H_{21}N_5O_3S$ requires C, 54.38; H, 5.64; N, 18.65%.

$^1$H-NMR (DMSO-$d_6$): δ=0.95 (t, 3H), 1.75 (m, 2H), 2.80 (t, 2H), 2.85 (s, 3H), 3.90 (s, 2H), 4.15 (s, 3H), 7.20 (d, 2H), 7.30 (d, 2H), 9.00 (s, 1H), 11.15 (s, 1H) ppm.

Examples 35 to 45

The compounds of the following tabulated Examples of the general formula:

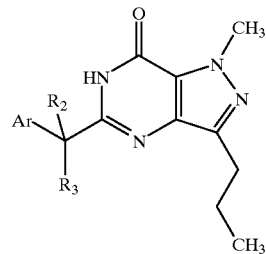

were prepared by reaction of the appropriate anilines and sulfonyl or sulphamoyl chlorides using similar methods to that described in Example 34.

| Ex. No. | Ar(R₂)(R₃)C— | Analysis/$^1$H-NMR/Melting Point/Crystallisation solvent |
|---|---|---|
| 35 | *(3-ethylphenyl methanesulfonamide structure)* | Found: C, 54.18; H, 5.61; N, 18.41%. $C_{17}H_{21}N_5O_3S$, requires C, 54.38; H, 5.64; N, 18.65%. $^1$H-NMR(DMSO-$d_6$): δ = 0.90(t, 3H), 1.70 (m, 2H), 2.70(t, 2H), 2.95(s, 3H), 3.85(s, 2H), 4.10(s, 3H), 7.05(m, 2H), 7.20(s, 1H), 7.25(m, 1H), 9.75(s, 1H), 12.30(s, 1H)ppm. Melting point: 179–181° C. Crystallisation solvent: acetone/hexane. |
| 36 | *(2-ethylphenyl methanesulfonamide structure)* | Found: C, 54.90; H, 5.73; N, 18.79%. $C_{17}H_{21}N_5O_3S$, requires C, 54.38; H, 5.64; N, 18.65%. $^1$H-NMR(DMSO-$d_6$): δ = 0.90(t, 3H), 1.65 (m, 2H), 2.70(t, 2H), 3.05(s, 3H), 4.05(s, 2H), 4.10(s, 3H), 7.15(m, 1H), 7.25(m, 2H), 7.40 (m, 1H)9.80(s, 1H), 12.40(s, 1H)ppm. Melting point: 256–257° C. Crystallisation solvent:ethyl acetate. |
| 37 | *(4-ethylphenyl benzenesulfonamide structure)* | Found: C, 60.31; H, 5.32; N, 15.96%. $C_{22}H_{23}N_5O_3S$, requires C, 60.40; H, 5.30; N, 16.01%. $^1$H-NMR(DMSO-$d_6$): δ = 0.90(t, 3H), 1.65 (m, 2H), 2.70(t, 2H), 3.75(s, 2H), 4.05(s, 3H), 7.00(d, 2H), 7.15(d, 2H), 7.55(m, 3H), 7.75(d, 2H), 10.20(s, 1H), 12.20(s, 1H)ppm. Melting point: 272–275° C. Crystallisation solvent:methanol/ethyl acetate. |

-continued

| Ex. No. | Ar(R$_2$)(R$_3$)C— | Analysis/$^1$H-NMR/Melting Point/Crystallisation solvent |
|---|---|---|
| 38 | 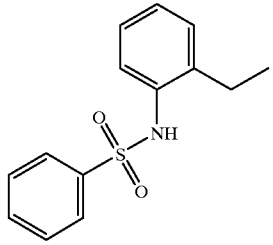 | Found: C, 60.67; H, 5.33; N, 16.04%. C$_{22}$H$_{23}$N$_5$O$_3$S, requires C, 60.40; H, 5.30; N, 16.01%. $^1$H-NMR(DMSO-d$_6$): δ = 0.90(t, 3H), 1.70 (m, 2H), 2.75(t, 2H), 3.70(s, 2H), 4.10(s, 3H), 7.00–7.25(m, 4H), 7.50–7.80(m, 5H), 10.30(s, 1H), 12.35(s, 1H)ppm Melting point: 244–248° C. Crystallisation solvent:methanol/ethyl acetate. |
| 39 | 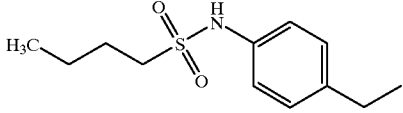 | Found: C, 57.40: H, 6.51; N, 16.59%. C$_{20}$H$_{27}$N$_5$O$_3$S, requires C, 57.53; H, 6.52; N, 16.77%. $^1$H-NMR(DMSO-d$_6$): δ = 0.80(t, 3H), 0.90(t, 3H), 1.30(m, 2H), 1.50–1.80(m, 4H), 2.70(t, 2H), 3.00(t, 2H), 3.85(s, 2H), 4.05(s, 3H), 7.10(d, 2H), 7.30(d, 2H), 9.70(s, 1H), 12.30 (s, 1H)ppm. Melting point: 221–224° C. Crystallisation solvent:ethyl acetate/hexane. |
| 40 | 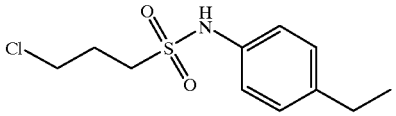 | Found: C, 52.48; H, 5.61; N, 15.91%. C$_{19}$H$_{24}$N$_5$ClO$_3$S, requires C, 52.11; H, 5.52; N, 15.99%. $^1$H-NMR(DMSO-d$_6$): δ = 0.90(t, 3H), 1.70 (m, 2H), 2.10(m, 2H), 2.75(t, 2H), 3.15(t, 2H), 3.70(t, 2H), 3.85(s, 2H), 4.10(s, 3H), 7.10(d, 2H), 7.30(d, 2H), 9.80(s, 1H), 12.25 (s, 1H)ppm. Melting point: 237–238° C. Crystallisation solvent:ethyl acetate. |
| 41 | 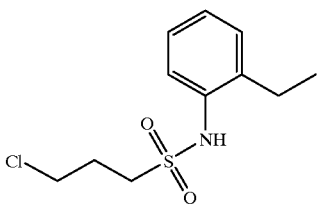 | Found: C, 52.41; H, 5.57; N, 15.76%. C$_{19}$H$_{24}$N$_5$ClO$_3$S, requires C, 52.11; H, 5.52; N, 15.99%. $^1$H-NMR(DMSO-d$_6$): δ = 0.90(t, 3H), 1.65 (m, 2H), 2.15(m, 2H), 2.70(t, 2H), 3.25(m, 2H), 3.70(t, 2H), 4.05(s, 2H), 4.10(s, 3H), 7.15(d, 1H), 7.25(m, 2H), 7.40(d, 1H), 9.90 (s, 1H), 12.40(s, 1H)ppm. Melting point: 220–223° C. Crystallisation solvent:ethyl acetate. |
| 42 | 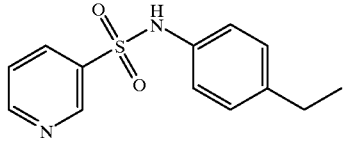 | Found: C, 57.15; H, 5.10; N, 19.12%. C$_{21}$H$_{22}$N$_6$O$_3$S, requires C, 57.52; H, 5.06; N, 19.16%. $^1$H-NMR(DMSO-d$_6$): δ = 0.90(t, 3H), 1.65 (m, 2H), 2.70(t, 2H), 3.80(s, 2H), 4.05(s, 3H), 7.00(d, 2H), 7.20(d, 2H), 7.55(m, 1H), 8.10(d, 1H), 8.75(d, 1H), 8.85(s, 1H), 10.45 (s, 1H), 12.20(s, 1H)ppm. Melting point: 251–252° C. Crystallisation solvent:acetonitrile. |
| 43 | 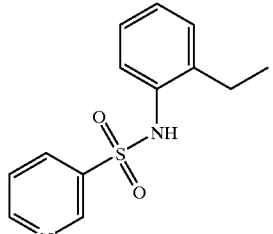 | Found: C, 57.45; H, 5.04; 19.12%. C$_{21}$H$_{22}$N$_6$O$_3$S, requires C, 57.52; H, 5.06; N, 19.16%. $^1$H-NMR(DMSO-d$_6$): δ = 0.90(t, 3H), 1.65 (m, 2H), 2.70(t, 2H), 3.75(s, 2H), 4.10(s, 3H), 7.00(d, 1H), 7.20(m, 3H), 7.60(m, 1H), 8.05(d, 1H), 8.80(m, 2H), 10.40(s, 1H), 12.35(s, 1H)ppm. Melting point: 233–234° C. Crystallisation solvent:ethyl acetate/hexane. |

| Ex. No. | Ar(R₂)(R₃)C— | Analysis/¹H-NMR/Melting Point/Crystallisation solvent |
|---|---|---|
| 44 | 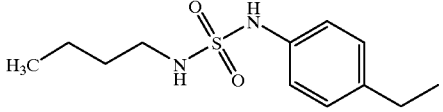 | Found: C, 55.93; H, 6.58; N, 19.01%.<br>$C_{20}H_{28}N_6O_3S$, requires C, 55.54; H, 6.52; N, 19.43%.<br>¹H-NMR(DMSO-d₆): δ = 0.70(t, 3H), 0.90(t, 3H), 1.15(m, 2H), 1.25(m, 2H), 1.70(m, 2H), 2.75(m, 4H), 3.80(s, 2H), 4.05(s, 3H), 7.05 d, 2H), 7.20(d, 2H), 7.35(m, 1H), 9.55(s, 1H), 12.25(s, 1H)ppm.<br>Melting point: 174–183° C. Crystallisation solvent:ethyl acetate/hexane. |
| 45 | 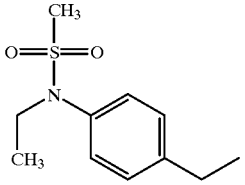 | Found: C, 56.23; H, 6.24; N, 17.17%.<br>$C_{19}H_{25}N_5O_3S$, requires C, 56.56; H, 6.25; N, 17.36%.<br>¹H-NMR(CDCl₃): δ = 1.05(t, 3H), 1.20(t, 3H), 1.85(m, 2H), 2.90(m, 5H), 3.75(q, 2H), 4.05(s, 2H), 4.25(s, 3H), 7.35(d, 2H), 7.45 (d, 2H), 9.50(s, 1H)ppm.<br>Melting point: 245–246° C. Crystallisation solvent:ethyl acetate. |

Example 46

N-{4-[(1-methyl-7-oxo-3-propyl-6,7-dihydro-1H-pyrazolo[4,3-d]pyrimidin-5-yl)methyl]phenyl}methanamide

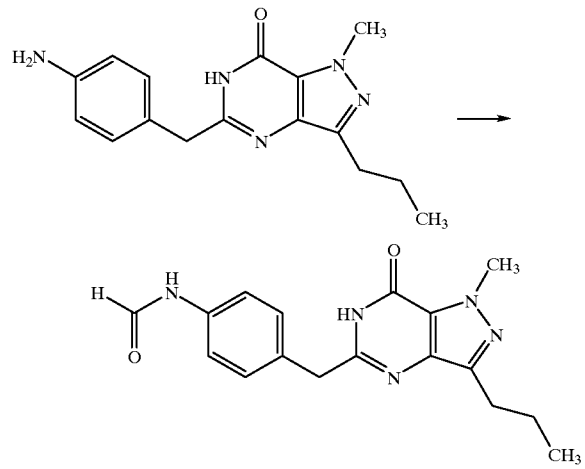

A mixture of 5-(4-aminobenzyl)-1-methyl-3-propyl-6,7-dihydro-1H-pyrazolo[4,3-d]-pyrimidin-7-one (297 mg, 0.0010 mol) and 1,2-diformylhydrazine (101 mg, 0.00115 mol) was heated to 200° C. The resulting melt was then stirred under a nitrogen atmosphere at this temperature for 55 minutes. On cooling, the solid was dissolved in dichloromethane:methanol, pre-absorbed onto silica and purified by flash column chromatography eluting with a solvent gradient of dichloromethane:methanol (99:1 to 96:4 by volume) then dichloromethane:methanol:0.880 aqueous ammonia (90:10:1 by volume). Crystallisation from ethyl acetate/methanol gave the title compound (170 mg), m.p.260–261° C.

Found: C, 62.44; H, 5.93; N, 21.22; $C_{17}H_{19}N_5O_2$, requires C, 62.76; H, 5.89; N, 21.52%.

¹H-NMR (DMSO-d₆): δ=0.91 (t, 3H), 1.70 (m, 2H), 2.82 (t, 2H), 3.84 (s, 2H), 406 (s, 3H), 7.25 (d, 2H), 7.50 (d, 2H), 8.22 (s, 1H), 10.16 (s, 1H), 12.28 (s, 1H) ppm.

Example 47

N-{4-[(1-methyl-7-oxo-3-propyl-6,7-dihydro-1H-pyrazolo[4,3-d]pyrimidin-5-yl)methyl]phenyl}acetamide

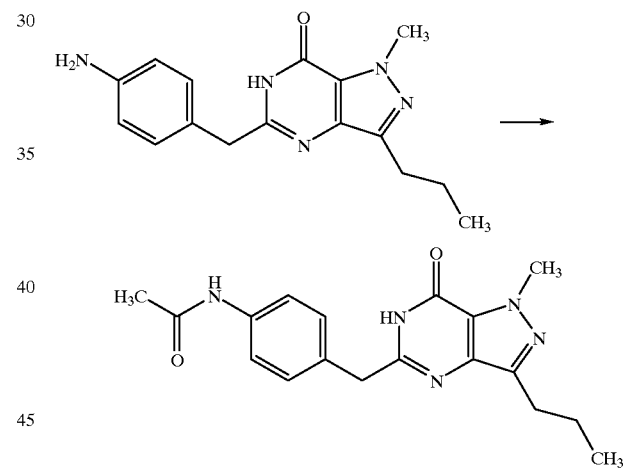

Triethylamine (160 μl, 0.0011 mol), dimethylaminopyridine (10 mg), and acetic anhydride (50 μl, 0.0005 mol) were added to a solution of 5-(4-aminobenzyl)-1-methyl-3-propyl-6,7-dihydro-1H-pyrazolo[4,3-d]pyrimidin-7-one (110 mg, 0.00037 mol) in dichloromethane (9 ml). The resulting mixture was stirred overnight at room temperature under a nitrogen atmosphere. The mixture was then partitioned between 2M aqueous hydrochloric acid solution (15 ml) and dichloromethane (15 ml) and the aqueous phase extracted with dichloromethane/methanol (30 ml). The combined organic extracts were dried (MgSO₄), filtered and concentrated under reduced pressure to give, after crystallisation from ethyl acetate/methanol, the title compound as an off white solid (105 mg), m.p.272–275° C.

Found: C, 63.17; H, 6.25; N, 20.05; $C_{18}H_{21}N_5O_2$, requires C, 63.70; H, 6.24; N, 20.64%.

¹H-NMR (DMSO-d₆): δ=0.92 (t, 3H), 1.70 (t, 2H), 2.00 (s, 3H), 2.72 (t, 2H), 3.82 (s, 2H), 4.06 (s, 3H), 7.21 (d, 2H), 7.50 (d, 2H), 9.88 (s, 1H), 12.24 (s, 1H) ppm.

Example 48

5-[4-(ethylamino)benzyl]-1-methyl-3-propyl-6,7-dihydro-1H-pyrazolo[4,3-d]pyrimidin-7-one

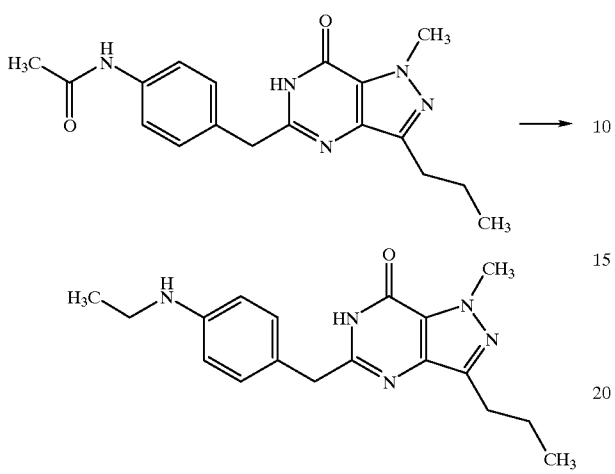

N-{4-[(1-methyl-7-oxo-3-propyl-6,7-dihydro-1H-pyrazolo[4,3-d]pyrimidin-5-yl)methyl]phenyl}acetamide (2.37 g, 0.007 mol) was added to a mixture of lithium aluminium hydride (705 mg, 0.0186 mol) in tetrahydrofuran (250 ml), under a nitrogen atmosphere. After the effervescence had subsided, the reaction was refluxed for 2 hours. On cooling, the mixture was treated dropwise with aqueous sodium hydroxide solution (5M, 1.1 ml), and the resulting solid filtered and washed well with tetrahydrofuran (250 ml). The filtrate was concentrated under reduced pressure and the residue partitioned between ethyl acetate (100 ml) and water (100 ml). The aqueous phase was extracted with ethyl acetate (200 ml) and the organic phases combined, dried ($MgSO_4$), filtered and concentrated under reduced pressure.

Purification by flash column chromatography, eluting with ethyl acetate followed by crystallisation from ethyl acetate gave the title compound (1.03 g), m.p. 186–188° C.

Found: C, 66.57; H, 7.09; N, 21.54; $C_{18}H_{23}N_5O$, requires C, 66.44; H, 7.12; N, 21.52%.

$^1$H-NMR (DMSO-$d_6$): δ=0.90 (t, 3H), 1.10 (t, 3H), 1.65 (m, 2H), 2.70 (t, 2H), 2.95 (m, 2H), 3.70 (s, 2H), 4.05 (s, 3H), 5.40 (t, 1H), 6.45 (d, 2H), 7.00 (d, 2H), 12.15 (s, 1H) ppm.

Example 49

N-ethyl-N-{4-[(1-methyl-7-oxo-3-propyl-6,7-dihydro-1H-pyrazolo[4,3-d]pyrimidin-5-yl)methyl]phenyl}acetamide The title compound was prepared from 5-[4-(ethylamino)benzyl]-1-methyl-3-propyl-6,7-dihydro-1H-pyrazolo[4,3-d]pyrimidin-7-one following the procedure described in Example 47 and was obtained, after trituration with ethyl acetate as a solid (59%), m.p.149–151° C.

Found: C, 65.05; H, 6.88; N, 18.92; $C_{20}H_{25}N_5O_2$, requires C, 65.37; H, 6.86; N, 19.06%.

$^1$H-NMR (CDCl$_3$): δ=1.05 (t, 3H), 1.15 (t, 3H), 1.86 (m, 5H), 2.92 (t, 2H), 3.76 (q, 2H), 7.18 (d, 2H), 7.44 (d, 2H), 9.75 (s, 1H) ppm.

Example 50

5-[4-(diethylamino)benzyl]-1-methyl-3-propyl-6,7-dihydro-1H-pyrazolo[4,3-d]pyrimidin-7-one

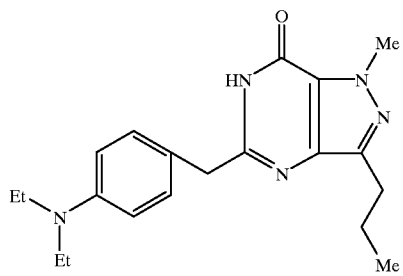

The title compound was prepared from N-ethyl-N-{4-[(1-methyl-7-oxo-3-propyl-6,7-dihydro-1H-pyrazolo[4,3-d]pyrimidin-5-yl)methyl]phenyl}acetamide following the procedure described in Example 48 and was obtained after crystallisation from acetone/hexane as a solid (45%), m.p.201–203° C.

Found: C, 68.11; H, 7.72; N, 19.94; $C_{20}H_{27}N_5O$ requires C, 67.96; H, 7.70; N, 19.82%.

$^1$H-NMR (CDCl$_3$): δ=1.05 (t, 3H), 1.20 (t, 6H), 1.85 (m, 2H), 2.90 (t, 2H), 3.40 (q, 4H), 3.95 (s, 2H), 4.20 (s, 3H), 6.70 (d, 2H), 7.10 (d, 2H), 8.65 (s, 1H) ppm.

Example 51

N-{4-[(1-methyl-7-oxo-3-propyl-6,7-dihydro-1H-pyrazolo[4,3-d]pyrimidin-5-yl)methyl]-2-nitrophenyl}acetamide

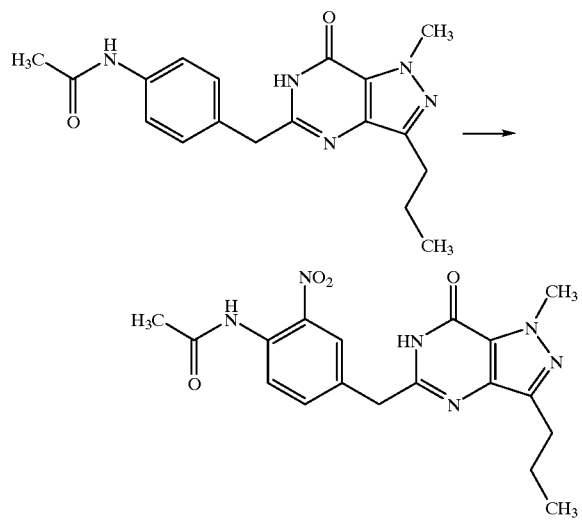

Glacial acetic acid (1.93 ml, 0.0337 mol) was added to N-{4-[(1-methyl-7-oxo-3-propyl-6,7-dihydro-1H-pyrazolo[4,3-d]-pyrimidin-5-yl)methyl]phenyl}acetamide (1.93 g, 0.0057 mol), followed by concentrated sulphuric acid (5.8 ml) and the mixture cooled in an ice-bath. Concentrated nitric acid (3.86 ml) was then added dropwise and once addition was complete, the reaction was stirred at room temperature for an hour.

The mixture was carefully poured onto ice and then extracted with dichloromethane (2×50 ml). The combined organic extracts were dried (MgSO$_4$), filtered and evaporated under reduced pressure.

Purification by flash column chromatography eluting with methanol:dichloromethane (2:98 by volume), followed by recrystallisation from acetic acid/water gave the title compound (619 mg), m.p.261–262° C.

Found: C, 55.84; H, 5.17; N, 21.48; C$_{18}$H$_{20}$N$_6$O$_4$, requires C, 56.24; H, 5.24; N, 21.87%.

1H-NMR (DMSO-d$_6$): d=0.90 (t, 3H), 1.70 (m, 2H), 2.05 (s, 3H), 2.71(t, 2H), 399 (s, 2H), 4.08 (s, 3H), 7.53 (d, 1H), 7.60 (d, 1H), 10.23 (s, 1H) ppm.

Example 52

2-{4-[(1-methyl-7-oxo-3-propyl-6,7-dihydro-1H-pyrazolo[4,3-d]pyrimidin-5-yl)methyl]phenylamino}acetic acid.

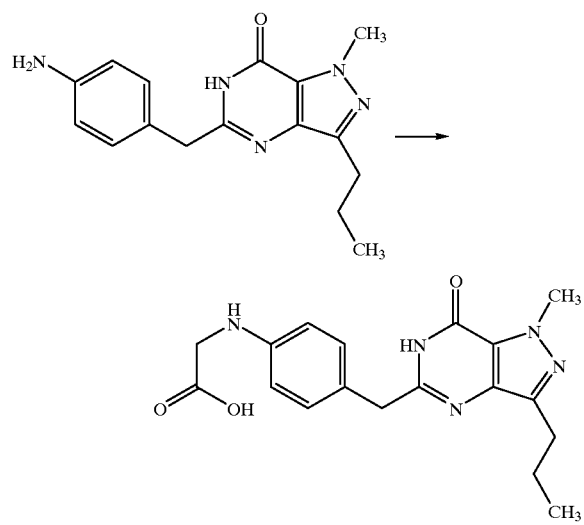

10% w/w Palladium on charcoal (87 mg) was added to a solution of 5-(4-aminobenzyl)-1-methyl-3-propyl-6,7-dihydro-1H-pyrazolo[4,3-d]pyrimidin-7-one (870 mg, 0.00293 mol) and glyoxylic acid hydrate (260 mg, 0.0035 mol) in methanol (20 ml) and the mixture hydrogenated at room temperature at 50 p.s.i. for 3 hours.

The mixture was filtered through Arbocel™ and washed well with 10% aqueous sodium hydroxide (60 ml). The filtrate was evaporated under reduced pressure and the residue partitioned between water (40 ml) and dichloromethane (40 ml). The aqueous layer was acidified to pH1 with 2M aqueous hydrochloric acid and extracted well with dichloromethane (2×50 ml). These combined organic extracts were dried (MgSO$_4$), filtered and evaporated under reduced pressure to give a brown solid.

Purification by flash column chromatography eluting with methanol:dichloromethane (3:97 by volume), followed by recrystallisation from acetone/hexane gave the title compound (180 mg), m.p.175–178° C.

$^1$H-NMR (CDCl$_3$): d=1.05 (t, 3H), 1.87 (m, 2H), 2.92 (t, 2H), 3.82 (s, 2H), 3.96(m, 3H), 4.24 (s, 3H), 6.64 (d, 2H), 7.14 (d, 2H), 8.67 (s, 1H) ppm.

Example 53

N-{4-[(1-methyl-7-oxo-3-propyl-6,7-dihydro-1H-pyrazolo[4,3-d]pyrimidin-5-yl)methyl]phenyl}-(E)-3-ethoxy-2-propenamide

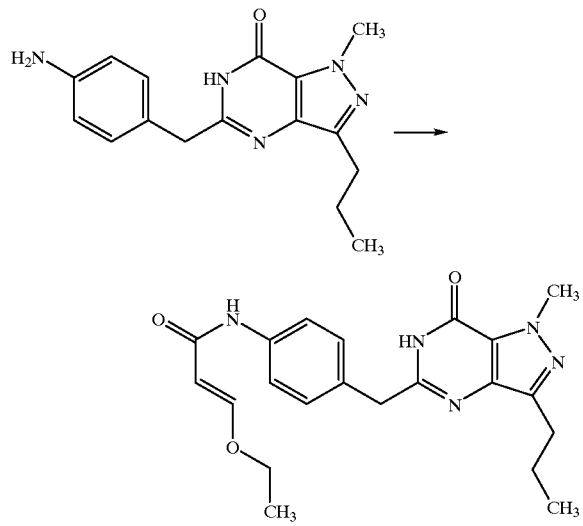

(E)-3-ethoxyacryloyl chloride (*J. Chem. Soc;* 1958,153) (298 mg, 0.0022 mol), was added dropwise to an ice-cooled solution of 5-(4-aminobenzyl)-1-methyl-3-propyl-6,7-dihydro-1H-pyrazolo[4,3-d]pyrimidin-7-one (600 mg, 0.002 mol) in pyridine (15 ml) and the reaction stirred at room temperature for 20 hours. The mixture was partitioned between water (30 ml) and dichloromethane (30 ml), the aqueous layer acidified to pH1 with 2M aqueous hydrochloric acid solution and then extracted with dichloromethane (2×40 ml). The combined organic extracts were dried (MgSO$_4$), filtered and evaporated under reduced pressure, to give, after recrystallisation from ethyl acetate/methanol the title compound (483 mg), m.p.241–243° C.

Found: C, 63.92; H, 6.44; N, 17.61; C$_{21}$H$_{25}$N$_5$O$_3$, requires C, 63.78; H, 6.37; N, 17.71%.

$^1$H-NMR (DMSO-d$_6$): d=0.93 (t, 3H), 1.24 (t, 3H), 1.70 (m, 2H), 2.74 (t, 2H), 3.82 (s, 2H), 3.94 (q, 2H), 4.08 (s, 3H), 5.50 (d, 1H), 7.21 (d, 2H), 7.44 (d, 1H), 7.52 (d, 2H), 9.68 (s, 1H), 12.24 (s, 1H) ppm.

Example 54

1-methyl-5-[(2-oxo-1,2-dihydro-6-quinolinyl)methyl]-3-propyl-6,7-dihydro-1H-pyrazolo[4,3-d]pyrimidin-7-one

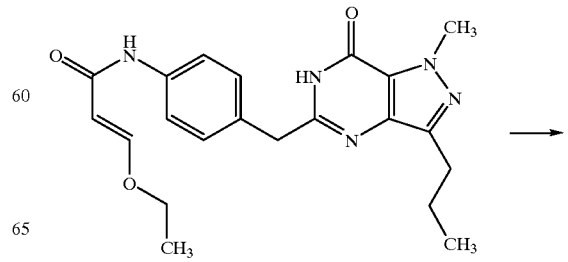

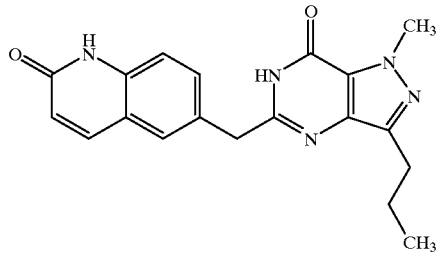

Concentrated sulphuric acid (10 ml) was added to N-{4-[(1-methyl-7-oxo-3-propyl-6,7-dihydro-1H-pyrazolo[4,3-d]pyrimidin-5-yl)methyl]phenyl}-(E)-3-ethoxy-2-propenamide (980 mg, 0.00248 mol) and the reaction stirred at room temperature for 4 hours. The mixture was then poured carefully onto ice and basified with 0.880 aqueous ammonia solution. The resulting precipitate was filtered and then triturated with boiling acetic acid/water to give the title compound (460 mg), m.p.>300° C.

Found: C, 64.57; H, 5.52; N, 19.94; $C_{19}H_{19}N_5O_2$ $0.25H_2O$, requires C, 64.47; H, 5.55; N, 19.79%.

$^1$H-NMR (DMSO-$d_6$): d=0.91 (t, 3H), 1.68 (m, 2H), 2.70 (t, 2H), 3.94 (s, 2H), 4.09 (s, 3H), 6.44 (d, 1H), 7.22 (d, 1H), 7.45 (d, 1H), 7.56 (s, 1H), 7.84 (d, 1H), 11.70 (s, 1H), 12.22 (s, 1H) ppm.

Example 55

N-{2-[(1-methyl-7-oxo-3-propyl-6,7-dihydro-1H-pyrazolo[4,3-d]pyrimidin-5-yl)methyl]phenyl}-3-(dimethylamino)-1-propanesulfonamide

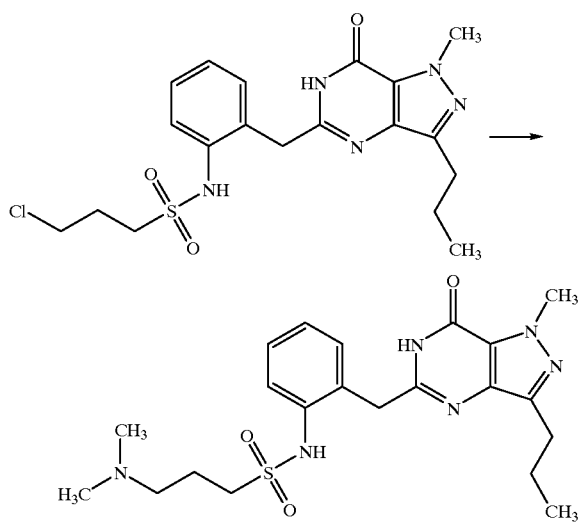

N-{2-[(1-methyl-7-oxo-3-propyl-6,7-dihydro-1H-pyrazolo[4,3-d]pyrimidin-5-yl)methyl]phenyl}-3-chloro-1-propanesulfonyl chloride (200 mg, 0.00046 mol) was dissolved in 33% w/w ethanolic dimethylamine (10 ml) and the reaction stirred at reflux for 3 hours. On cooling, the reaction was concentrated under reduced pressure and the residue partitioned between water (15 ml) and dichloromethane (15 ml). The aqueous layer was extracted with dichloromethane (40 ml) and the combined organic extracts dried (MgSO$_4$), filtered and evaporated under reduced pressure.

Purification by flash column chromatography eluting with a solvent gradient of 0.880 aqueous ammonia:methanol:dichloromethane (0:3:97 to 1:10:89 by volume) gave, after recrystallistion from ethyl acetate/hexane, the title compound (70 mg), m.p.202–204° C.

Found: C, 56.08; H, 6.80; N, 18.74; $C_{21}H_{30}N_6O_3S$, requires C, 56.48; H, 6.77; N, 18.82%.

$^1$H-NMR (CDCl$_3$): d=1.08 (t, 3H), 1.86 (m, 2H), 2.12 (m, 2H), 2.23 (s, 6H), 2.46 (t, 2H), 2.94 (t, 2H), 3.29 (t, 2H), 4.16 (s, 2H), 4.32 (s, 3H), 7.10 (m, 1H), 7.28 (m, 1H), 7.48 (d, 1H), 7.57 (d, 1H) ppm.

Example 56

2-{2-[(1-methyl-7-oxo-3-propyl-6,7-dihydro-1H-pyrazolo[4,3-d]pyrimidin-5-yl)methyl]phenyl}tetrahydro-2H-isothiazole-1,1-dioxide

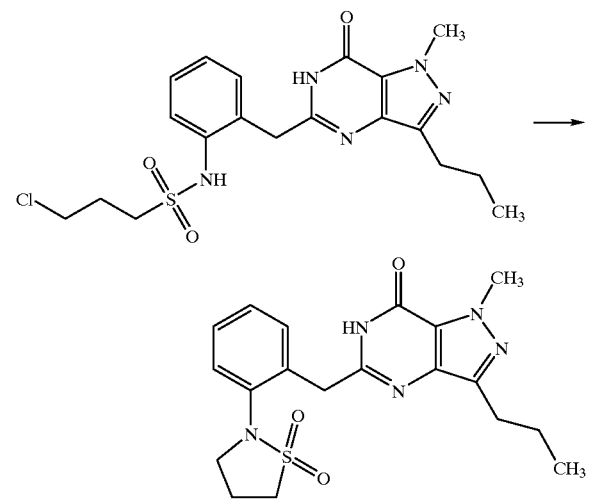

N-{2-[(1-methyl-7-oxo-3-propyl-6,7-dihydro-1H-pyrazolo[4,3-d]pyrimidin-5-yl)methyl]phenyl}-3-chloro-1-propanesulfonyl chloride (200 mg, 0.00046 mol) was added to a mixture of sodium hydride (27 mg, 80% w/w oil dispersion, 0.00091 mol) in dimethylformamide (10 ml) and the reaction stirred for 20 hours at room temperature, under a nitrogen atmosphere. Methanol (5 ml) was added and the mixture concentrated under reduced pressure. The residue was partitioned between ethyl acetate (20 ml) and water (20 ml), the aqueous phase acidified to pH1 with aqueous hydrochloric acid solution (1M) and extracted with ethyl acetate (2×25 ml). These combined organic phases were dried (MgSO$_4$), filtered, and concentrated under reduced pressure to give, after recrystallisation from ethyl acetate/hexane the title compound, as a white solid (139 mg), m.p.181–182° C.

Found: C, 56.40; H, 5.77; N, 17.34; $C_{19}H_{23}N_5O_3S$, requires C, 56.84; H, 5.77; N, 17.44%.

$^1$H-NMR (DMSO-$d_6$): δ=0.85 (t, 3H), 1.65 (m, 2H), 2.35 (m, 2H), 2.65 (t, 2H), 3.40 (t, 2H), 3.60 (t, 2H), 4.05 (s, 2H), 4.10 (s, 3H), 7.35 (m, 3H), 7.45 (m, 1H), 12.20 (s, 1H) ppm.

Example 57

2-{4-[(1-methyl-7-oxo-3-propyl-6,7-dihydro-1H-pyrazolo[4,3-d]pyrimidin-5-yl)methyl]phenyl}tetrahydro-2H-isothiazole-1,1-dioxide The title compound was prepared from N-{4-[(1-methyl-7-oxo-3-propyl-6,7-dihydro-1H-pyrazolo[4,3-d]pyrimidin- 5-yl)methyl]phenyl}-3-chloro-1-propanesulfonyl chloride following the procedure described in Example 56 and was obtained as a solid (70%), m.p.254–255° C.

Found: C, 56.73; H, 5.77; N, 17.30; $C_{19}H_{23}N_5O_3S$, requires C, 56.84; H, 5.77; N, 17.44%.

$^1$H-NMR (DMSO-$d_6$): δ=0.90 (t, 3H), 1.70 (m, 2H), 2.35 (m, 2H), 2.70 (t, 2H), 3.45 (t, 2H), 3.70 (t, 2H), 3.85 (s, 2H), 4.05 (s, 3H), 7.15 (d, 2H), 7.35 (d, 2H), 12.30(s, 1H) ppm.

Examples 58 and 59

Preparation of 3-[(1-methyl-7-oxo-3-propyl-6,7-dihydro-1H-pyrazolo[4,3-d]pyrimidin-5-yl)methyl]-benzenesulfonyl chloride and 4-[(1-methyl-7-oxo-3-propyl-6,7-dihydro-1H-pyrazolo[4,3-d]pyrimidin-5-yl)methyl]-benzenesulfonyl chloride

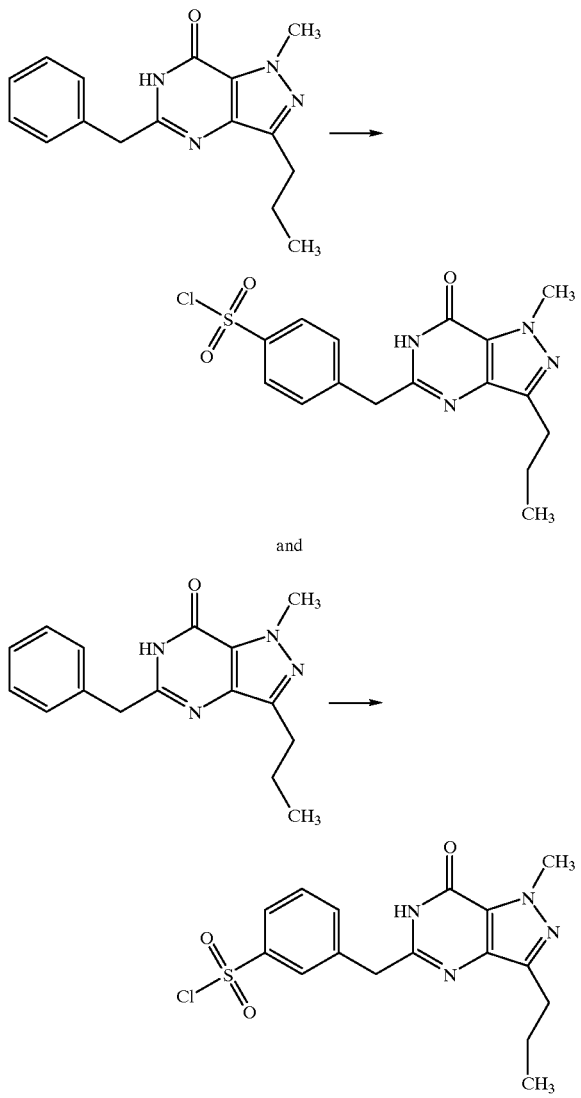

5-benzyl-1-methyl-3-propyl-6,7-dihydro-1H-pyrazolo[4,3-d]-pyrimidin-7-one (500 mg, 0.00178 mol) was dissolved in chlorosulfonic acid (2.5 ml, 0.0376 mol) to give an orange solution which was then warmed to 60° C. for 2 hours. On cooling, the solution was pipetted onto ice and then extracted with dichloromethane (2×20 ml). The combined organic extracts were dried (MgSO$_4$), filtered and concentrated under reduced pressure. Crystallisation from ethyl acetate gave the 4-substituted title compound, m.p.>350° C. (some decomposition at 240° C.).

Found: C, 50.56; H, 4.51; N, 14.48; $C_{16}H_{17}N_4ClO_3S$, requires C, 50.46; H, 4.50; N, 14.71%.

$^1$H-NMR (CDCl$_3$): δ=1.05 (t, 3H), 1.85 (m, 2H), 2.90 (t, 2H), 4.10 (s, 2H), 4.30 (s, 3H), 7.70 (d, 2H), 8.00 (d, 2H), 11.60 (s, 1H) ppm.

The mother liquors were evaporated under reduced pressure to give the 3-substituted title compound (88 mg).

Found: C, 50.56; H, 4.51; N, 14.48; $C_{16}H_{17}N_4ClO_3S$, requires C, 50.46; H, 4.50; N, 14.71%.

$^1$H-NMR (CDCl$_3$): δ=1.03 (t, 3H), 1.86 (m, 2H), 2.92 (t, 2H), 4.22 (s, 2H), 4.33 (s, 3H), 7.60 (m, 1H), 7.86 (d, 1H), 8.00 (d, 1H), 8.23 (s, 1H), 11.98 (s, 1H) ppm.

Examples 60 and 61

3-[(1-ethyl-7-oxo-3-propyl-6,7-dihydro-1H-pyrazolo[4,3-d]pyrimidin-5-yl)methyl]-1-benzenesulfonamide and 4-[(1-ethyl-7-oxo-3-propyl-6,7-dihydro-1H-pyrazolo[4,3-d]pyrimidin-5-yl)methyl]-1-benzenesulfonamide

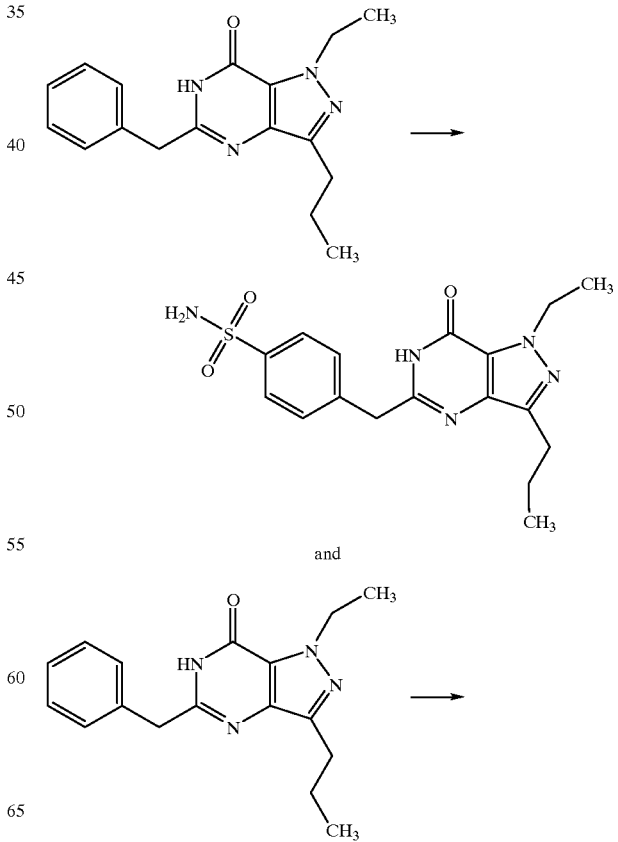

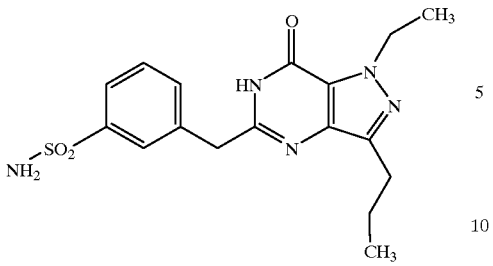

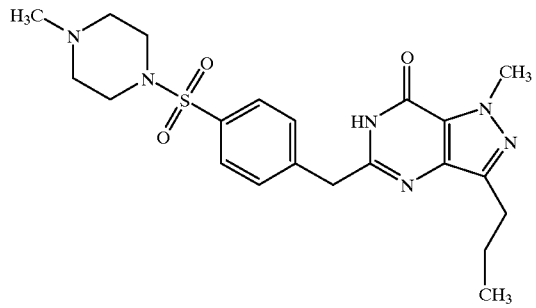

5-benzyl-1-ethyl-3-propyl-6,7-dihydro-1H-pyrazolo[4,3-d]pyrimidin-7-one (480 mg, 0.0016 mol) was dissolved in chlorosulfonic acid (5 ml) and the solution warmed to 60° C. for 2 hours. On cooling, the mixture was pipetted onto ice to give a pale brown suspension.

0.880 Aqueous ammonia solution was then added until the mixture became basic with dissolution of all the solid. The resulting orange solution was then acidified with concentrated hydrochloric acid solution and extracted with dichloromethane/methanol (2×75 ml). The organic extracts were combined, dried (MgSO$_4$), filtered and concentrated under reduced pressure.

Purification by flash column chromatography, eluting with a solvent gradient of dichloromethane/methanol (97:3 to 95:5, by volume), gave a fractional separation of the two product isomers. The first product fractions to elute were combined, evaporated under reduced pressure, the residue was crystallised from ethyl acetate to give the 3-substituted title compound as a solid (40 mg), m.p. 222–224° C.

Found: C, 54.20; H, 5.68; N, 18.57; $C_{17}H_{21}N_5O_3S$, requires C, 54.39; H, 5.64; N, 18.65%.

$^1$H-NMR (DMSO-d$_6$): δ=0.90 (t, 3H), 1.35 (t, 3H), 1.70 (m, 2H), 2.70 (t, 2H), 4.00 (s, 2H), 4.45 (m, 2H), 7.30 (s, 2H), 7.50 (m, 2H), 7.70 (d, 1H), 7.80 (s, 1H), 12.40 (s, 1H) ppm.

The later product fractions to elute were combined, evaporated under reduced pressure, and the residue was crystallised from methanol, to give the 4-substituted title compound as a solid (110 mg), m.p.248–250° C.

Found: C, 54.26; H, 5.63; N, 18.52; $C_{17}H_{21}N_5O_3S$, requires C, 54.39; H, 5.64; N, 18.65%.

$^1$H-NMR (DMSO-d$_6$): δ=0.90 (t, 3H), 1.30 (t, 3H), 1.65 (m, 2H), 2.70 (t, 2H), 4.00 (s, 2H), 4.45 (m, 2H), 7.30 (s, 2H), 7.50 (d, 2H), 7.75 (d, 2H), 12.35 (s, 1H) ppm.

Example 62

5-(4-([4-methylpiperazin-1-yl]sulphonyl)benzyl)-1-methyl-7-oxo-3-propyl-6,7-dihydro-1H-pyrazolo[4,3-d]pyrimidine

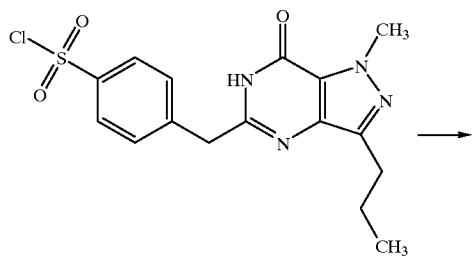

N-methyl piperazine (1.28 ml, 0.0115 mol) was added to a solution of 4-[(1-methyl-7-oxo-3-propyl-6,7-dihydro-1H-pyrazolo[4,3-d]pyrimidin-5-yl)methyl]-1-benzenesulfonyl chloride (1.35 g, 0.0035 mol) in ethanol (20 ml) and the reaction stirred at room temperature for 18 hours. The reaction mixture was concentrated under reduced pressure and the residue partitioned between dichloromethane (50 ml) and water (20 ml). The aqueous phase was extracted with further dichloromethane (50 ml), the combined organic extracts dried (MgSO$_4$), filtered, and evaporated under reduced pressure.

Purification by flash column chromatography eluting with methanol:dichloromethane (3:97 by volume) followed by trituration with ethyl acetate gave the title compound as a solid.

Found: C, 55.91; H, 6.29; N, 18.53; $C_{21}H_{28}N_6O_3S$, requires C, 56.74; H, 6.35; N, 18.90%.

$^1$H-NMR (CDCl$_3$): δ=1.05 (t, 3H), 1.85 (m, 2H), 2.25 (s, 3H), 2.45 (m, 4H), 3.00 (m, 6H), 4.15 (s, 2H), 4.30 (s, 3H), 7.68 (m, 4H), 11.60 (s, 1H) ppm.

Examples 63 to 66

The compounds of the following tabulated Examples of the general formula:

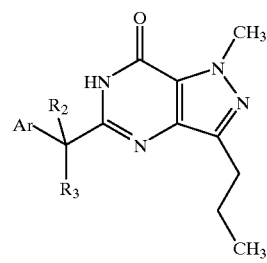

were prepared by reaction of the corresponding sulfonyl chloride and amine by similar methods to that used in Example 62.

| Ex. No. | Ar(R₂)(R₃)C— | Analysis/¹H-NMR/Melting Point/Crystallisation solvent |
|---|---|---|
| 63 | 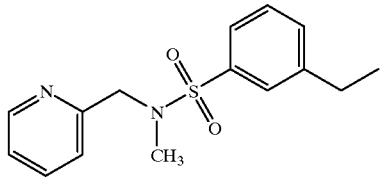 | Found: C, 59.10; H, 5.59; N, 17.91%. C$_{23}$H$_{26}$N$_6$O$_3$S, requires C, 59.21; H, 5.62; N, 18.01%. ¹H-NMR(CDCl$_3$): δ = 1.00(t, 3H), 1.70(m, 2H), 2.65(s, 3H), 2.90(t, 2H), 4.15(s, 2H), 4.25(s, 2H), 4.30(s, 3H), 7.20(m, 1H), 7.50 (m, 2H), 7.75(m, 3H), 8.00(s, 1H), 8.40(s, 1H), 11.60(s, 1H)ppm. Melting point: 180–182° C. Crystallisation solvent:ethyl acetate/methanol. |
| 64 | 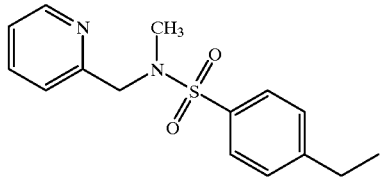 | Found: C, 58.96; H, 5.63; N, 17.90%. C$_{23}$H$_{26}$N$_6$O$_3$S, requires C, 59.21; H, 5.62; N, 18.01%. ¹H-NMR(CDCl$_3$): δ = 1.05(t, 3H), 1.85(m, 2H), 2.70(s, 3H), 2.95(t, 2H), 4.15(s, 2H), 4.30(s, 5H), 7.20(m, 1H), 7.55(d, 1H), 7.65 (d, 2H), 7.73(m, 1H), 7.82(d, 2H), 8.47(s, 1H), 11.40(s, 1H)ppm. Melting point: 206–208° C. Crystallisation solvent:ethyl acetate/methanol. |
| 65 | 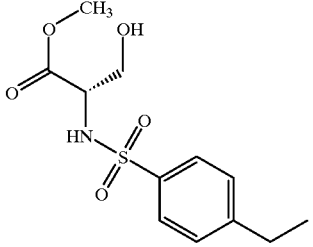 | Found: C, 50.72; H, 5.51; N, 14.67%. C$_{20}$H$_{25}$N$_5$O$_6$S 0.5 H$_2$O, requires C, 50.83; H, 5.55; N, 14.82%. ¹H-NMR(DMSO-d$_6$): δ = 0.90(t, 3H), 1.65 (m, 2H), 2.70(t, 2H), 3.28(s, 3H), 3.45(m, 2H), 3.80(m, 1H), 4.00(s, 2H), 4.10(s, 3H), 5.05 (m, 1H), 7.50(d, 2H), 7.70(d, 2H), 8.20 (br.s, 1H), 12.35(br.s, 1H)ppm. Melting point: 225–227° C. Crystallisation solvent:ethyl acetate/methanol. |
| 66 | 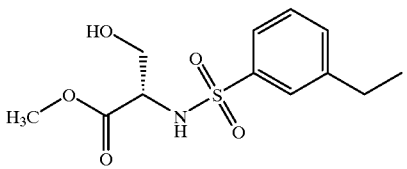 | Found: C, 51.44: H, 5.49; N, 14.74%. C$_{20}$H$_{25}$N$_5$O$_6$S, requires C, 51.83; H, 5.44; N, 15.11%. ¹H-NMR(DMSO-d$_6$): δ = 0.90(t, 3H), 1.65 (m, 2H), 2.70(t, 2H), 3.30(s, 3H), 3.45(m, 2H), 3.80(t, 1H), 4.00(s, 2H), 4.10(s, 3H), 5.00(m, 1H), 7.50(m, 2H), 7.65(m, 1H), 7.75(s, 1H), 8.25(br.s, 1H), 12.40(br.s, 1H) ppm. Melting point: 148–150° C. Crystallisation solvent:ethyl acetate/methanol. |

Example 67

4-[(1-methyl-7-oxo-3-propyl-6,7-dihydro-1H-pyrazolo[4,3-d]pyrimidin-5-yl)methyl]-1-benzenesulfonic acid

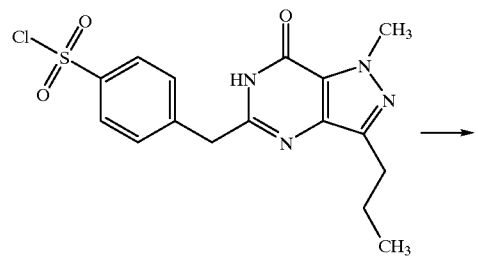

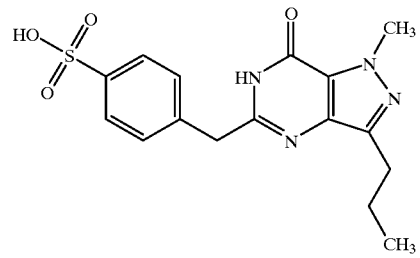

A solution of 4-[(1-methyl-7-oxo-3-propyl-6,7-dihydro-1H-pyrazolo[4,3-d]pyrimidin-5-yl)methyl]-1-benzenesulfonyl chloride (250 mg, 0.00065 mol) in 1N aqueous sodium hydroxide solution (3 ml) was stirred at room temperature for 2 hours. The reaction was acidified to pH1 with 2N aqueous hydrochloric acid and the resulting crystals filtered, washed with water, and dried by air suction, to yield the title compound (178 mg), m.p.>350° C.

Found: C, 52.35; H, 5.04; N, 15.13; C$_{16}$H$_{18}$N$_4$O$_4$S, requires: C, 53.03; H, 5.01; N, 15.46%.

$^1$H-NMR (DMSO-d$_6$): d=0.90 (t, 3H), 1.68 (m, 2H), 2.71 (t, 2H), 3.92 (s, 2H), 4.07 (s, 3H), 5.80 (s, 1H), 7.25 (d, 2H), 7.54 (d, 2H) ppm.

Example 68

(2S)-3-hydroxy-2-({4-[(1-methyl-7-oxo-3-propyl-6,7-dihydro-1H-pyrazolo[4,3-d]pyrimidin-5-yl)methyl]phenyl}sulfonamido)propanamide

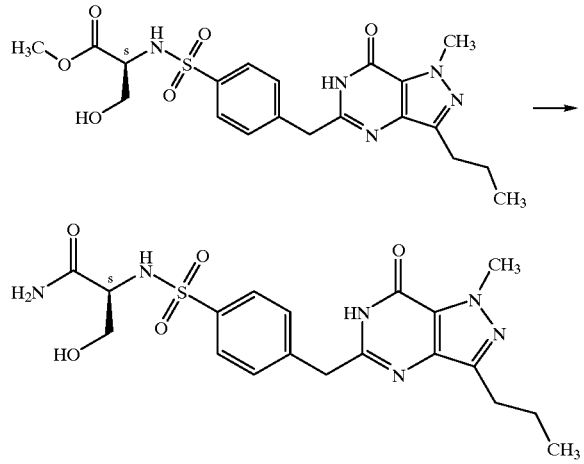

Methyl (2S)-3-hydroxy-2-({4-[(1-methyl-7-oxo-3-propyl-6,7-dihydro-1H-pyrazolo[4,3-d]pyrimidin-5-yl)methyl]phenyl}sulfonamido)propanoate (280 mg, 0.0006 mol) was dissolved in 0.880 aqueous ammonia solution (10 ml), and stirred at room temperature for 60 hours. The reaction mixture was then concentrated under reduced pressure, suspended in water (10 ml), then re-concentrated under reduced pressure. Crystallisation from ethanol gave the title compound (192 mg), m.p.226–229° C.

Found: C, 49.97; H, 5.70; N, 18.04; C$_{19}$H$_{24}$N$_6$O$_5$S 0.5 H$_2$O, requires C, 49.87; H, 5.51; N, 18.37%.

$^1$H-NMR (DMSO-d$_6$): δ=0.90 (t, 3H), 1.70 (m, 2H), 2.70 (t, 2H), 3.40 (m, 2H), 3.60 (m, 1H), 3.95 (s, 2H), 4.10 (s, 3H), 4.85 (m, 1H), 7.00 (s, 1H), 7.20 (s, 1H), 7.45(d, 2H), 7.65 (d,1H), 7.75 (d, 2H), 12.35 (s, 1H) ppm.

Example 69

(2S)-3-hydroxy-2-({3-[(1-methyl-7-oxo-3-propyl-6,7-dihydro-1H-pyrazolo[4,3-d]pyrimidin-5-yl)methyl]phenyl}sulfonamido)propanamide The title compound was prepared from methyl-(2S)-3-hydroxy-2-({3-[(1-methyl-7-oxo-3-propyl-6,7-dihydro-1H-pyrazolo[4,3-d]pyrimidin5yl)methyl]phenyl}sulfonamido)propanoate following the procedure described in Example 68 and was obtained as a solid (40%) m.p.232–238° C.

Found: C, 49.24; H, 5.73; N, 17.82; C$_{19}$H$_{24}$N$_6$O$_5$S H$_2$O, requires C, 48.92; H, 5.62; N, 18.01%.

$^1$H-NMR (DMSO-d$_6$): δ=0.90 (t, 3H), 1.70 (m, 2H), 2.70 (t, 2H), 3.40 (m, 2H), 3.65 (m, 1H), 4.00 (s, 2H), 4.10 (s, 3H), 4.85 (m, 1H), 7.05 (s, 1H), 7.20 (s, 1H), 7.50 (m, 2H), 7.70 (m, 2H), 7.80 (s, 1H), 12.40 (s, 1H) ppm.

Example 70

5-[4-(4H-1,2,4-triazol-4-yl)benzyl]-1-methyl-3-propyl-6,7-dihydro-1H-pyrazolo[4,3-d]pyrimidin-7-one

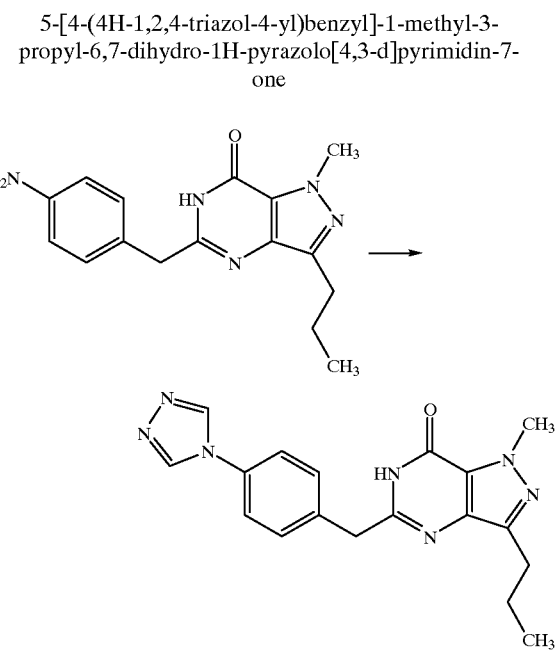

A mixture of 5-(4-aminobenzyl)-1-methyl-3-propyl-6,7-dihydro-1H-pyrazolo[4,3-d]pyrimidin-7-one (297 mg, 0.0010 mol) and 1,2-diformylhydrazine (101 mg, 0.00115 mol) was heated to 200° C. The resulting melt was then stirred under a nitrogen atmosphere at this temperature for 55 minutes. On cooling, the solid was dissolved in dichloromethane:methanol, pre-absorbed onto silica and purified by flash column chromatography eluting with a solvent gradient of dichloromethane:methanol (99:1 to 96:4 by volume) then dichloromethane:methanol:0.880 aqueous ammonia (90:10:1 by volume). Crystallisation from ethyl acetate/methanol gave the title compound (120 mg), m.p.297–300° C.

Found: C, 60.87; H, 5.56; N, 27.21; C$_{18}$H$_{19}$N$_7$O 0.25H$_2$O requires C, 61.09; H, 5.55; N, 27.70%.

$^1$H-NMR (DMSO-d$_6$): d=0.90 (t, 3H), 1.70 (m, 2H), 2.72 (t, 2H), 3.96 (s, 2H), 4.08 (s, 3H), 7.50 (d, 2H), 7.63 (d, 2H), 9.07 (s, 2H), 12.35 (s, 1H).

Example 71

5-[4-(1-Imidazolyl)benzyl]-1-methyl-3-propyl-6,7-dihydro-1H-pyrazolo[4,3-d]pyrimidin-7-one

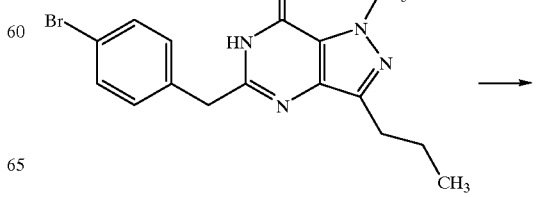

51
-continued

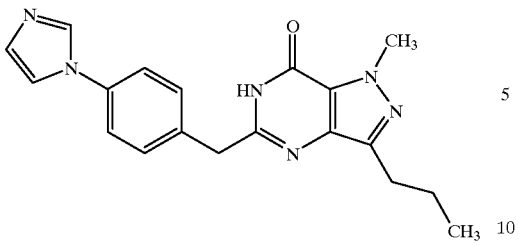

5-(4-Bromobenzyl)-1-methyl-3-propyl-6,7-dihydro-1H-pyrazolo[4,3-d]pyrimidin-7-one (390 mg, 0.00108 mol), imidazole (380 mg, 0.00558 mol), potassium carbonate (160 mg, 0.00116 mol), copper bronze (75 mg) and iodine (46 mg, 0.00018 mol) in N-methyl-2-pyrrolidinone (6 ml) were heated under a nitrogen atmosphere at 200° C. for 3 hours. On cooling, the mixture was concentrated under reduced pressure and the residue partitioned between ethyl acetate (10 ml) and water (10 ml). The aqueous phase was extracted with ethyl acetate (30 ml), and the combined organic extracts washed with brine, dried (MgSO$_4$), filtered and concentrated under reduced pressure.

Purification by flash column chromatography eluting with 0.880 aqueous ammonia:methanol:dichloromethane (0.5:5:95, by volume) followed by crystallisation from ethanol gave the title compound as a solid (85 mg) m.p.252–254° C.

Found: C, 65.28; H, 5.76; N, 24.01; $C_{19}H_{20}N_6O$, requires C, 65.50; H, 5.79; N, 24.12%.

$^1$H-NMR (CDCl$_3$): δ=1.05 (t, 3H), 1.85 (m, 2H), 2.95 (t, 2H), 4.15 (s, 2H), 4.30 (s, 3H), 7.30 (m, 2H), 7.40 (d, 2H), 7.50 (d, 2H), 7.83 (s, 1H), 10.45 (s, 1H) ppm.

52

Examples 72 to 74

The compounds of the following tabulated examples of the general formula:

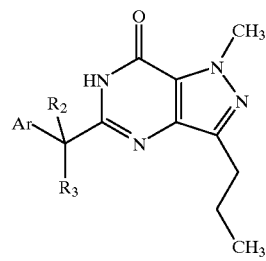

were prepared by reaction of the appropriate bromides and heterocycles following the procedure described in Example 71.

| Ex. No. | Ar(R$_2$)(R$_3$)C— | Analysis/$^1$H-NMR/Melting Point/Crystallisation solvent |
|---|---|---|
| 72 | (1,2,4-triazol-1-yl)phenyl-CH$_2$— | Found: C, 62.14; H, 5.53; N, 28.30%. $C_{18}H_{19}N_7O$, requires C, 61.88; H, 5.48; N, 28.06%. $^1$H-NMR(CDCl$_3$): δ = 0.90(t, 3H), 1.70(m, 2H), 2.70(t, 2H), 4.00(s, 2H), 4.10(s, 3H), 7.50(d, 2H), 7.80(d, 2H), 8.20(s, 1H), 9.20(s, 1H), 12.35(s, 1H) ppm. Melting point: 221–224° C. Crystallisation solvent:ethyl acetate/methanol. |
| 73 | (imidazol-1-yl)phenyl-CH(CH$_3$)— | Found: C, 66.26; H, 6.26; N, 23.14%. $C_{20}H_{22}N_6O$, requires C, 66.28; H, 6.12; N, 23.19%. $^1$H-NMR(CDCl$_3$): δ = 1.05(t, 3H), 1.80(d, 3H), 1.90(m, 2H), 2.95(t, 2H), 4.20(q, 1H), 4.25(s, 3H), 7.30(m, 2H), 7.35(d, 2H), 7.50(d, 2H), 7.80(s, 1H), 10.20(s, 1H) ppm. Melting point: 210–212° C. |
| 74 | (4-methylimidazol-1-yl)phenyl-CH$_2$— | Found: C, 65.98; H, 6.13: N, 22.95% $C_{20}H_{22}N_6O$, requires C, 66.28; H, 6.12; N, 23.19% $^1$H-NMR(DMSO-d$_6$): δ = 0.90(t, 3H), 1.70(m, 2H), 2.15 (s, 3H), 2.70(t, 2H), 3.90(s, 2H), 4.10(s, 3H), 7.40(m, 3H), 7.55(d, 2H), 8.05(s, 1H), 12.30(s, 1H) ppm. Melting point: 244–246° C. Crystallisation solvent:ethyl acetate/methanol. (Only the 4-isomer was isolated) |

Example 75

5-(4-hydroxybenzyl)-1-methyl-3-propyl-6,7-dihydro-1H-pyrazolo[4,3-d]pyrimidin-7-one

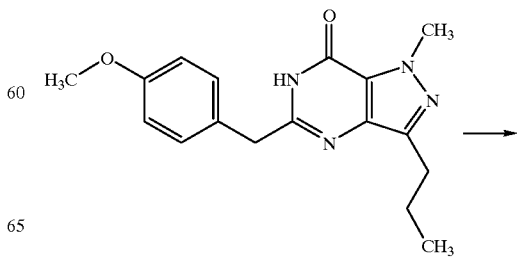

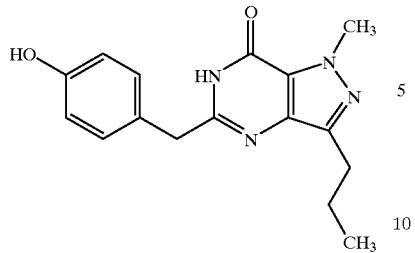

60% w/w Hydrobromic acid (20 ml) was added to 5-(4-methoxybenzyl)-1-methyl-3-propyl-6,7-dihydro-1H-pyrazolo[4,3-d]pyrimidin-7-one (630 mg) and the mixture stirred at 130° C. for 90 minutes. On cooling, the reaction was neutralized with saturated aqueous sodium carbonate solution and partitioned between dichloromethane (40 ml) and water (40 ml). The aqueous layer was further extracted with dichloromethane (100 ml), the combined organic layers dried (MgSO$_4$), filtered and evaporated under reduced pressure. Crystallisation from ethyl acetate gave the title compound (75 mg), m.p.260° C.

Found: C, 63.35; H, 6.02; N, 18.68; C$_{16}$H$_{18}$N$_4$O$_2$ 0.25H$_2$O, requires: C, 63.46; H, 6.16; N, 18.50%.

$^1$H-NMR (CDCl$_3$): d=0.95 (t, 3H), 1.74 (m, 2H), 2.80 (t, 2H), 3.83 (s, 2H), 4,12 (s, 3H), 6.72 (d, 2H), 7.08 (d, 2H), 8.60 (s, 1H), 10.70 (s, 1H) ppm.

Example 76

4-[(1-methyl-7-oxo-3-propyl-6,7-dihydro-1H-pyrazolo[4,3-d]pyrimidin-5-yl)methyl] phenoxyacetic acid

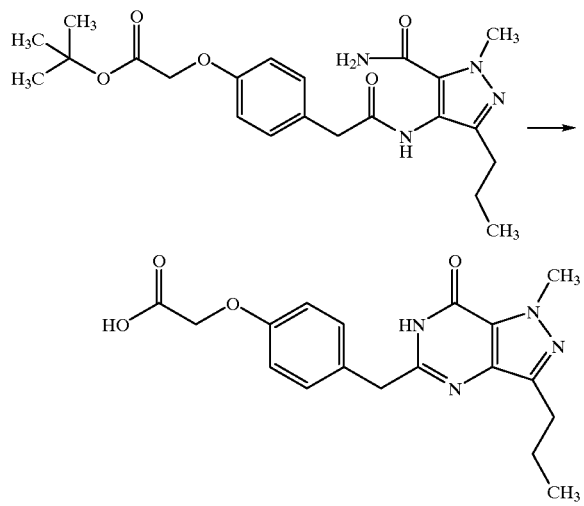

Aqueous hydrogen peroxide solution (0.35 ml, 30% w/w, 0.0031 mol) was added to a solution of sodium hydroxide (350 mg, 0.0088 mol) in water (14 ml). Tert-butyl 2-(4-{N-[5-carbamoyl-1-methyl-3-propyl-1H-4-pyrazolyl)carbamoyl]methyl}phenoxy)acetate (530 mg, 0.0012 mol) in ethanol (7 ml) was then added and the reaction stirred at reflux for 1 hour. On cooling, the mixture was concentrated under reduced pressure, the residue dissolved in water (15 ml) and acidified to pH2 with 1N aqueous hydrochloric acid. The resulting precipitate was filtered, washed with water (40 ml) and dried under air suction. Recrystallisation from ethanol gave the title compound (340 mg), m.p.230–232° C.

Found: C, 57.69; H, 5.52; N, 14.90; C$_{18}$H$_{20}$N$_4$O$_4$H$_2$O, requires C, 57.75; H, 5.92; N, 14.97%.

$^1$H-NMR (DMSO-d$_6$): d=0.92 (t, 3H), 1.68 (m, 2H), 2.72 (t, 2H), 3.81 (s, 2H), 4.07 (s, 3H), 4.62 (s, 2H), 6.82 (d, 2H), 7.23 (d, 2H), 12.25 (s, 1H), 12.98 (s, 1H) ppm.

Example 77

(1-methyl-7-oxo-3-propyl-6,7-dihydro-1H-pyrazolo[4,3-d]pyrimidin-5-yl)(phenyl)methyl acetate

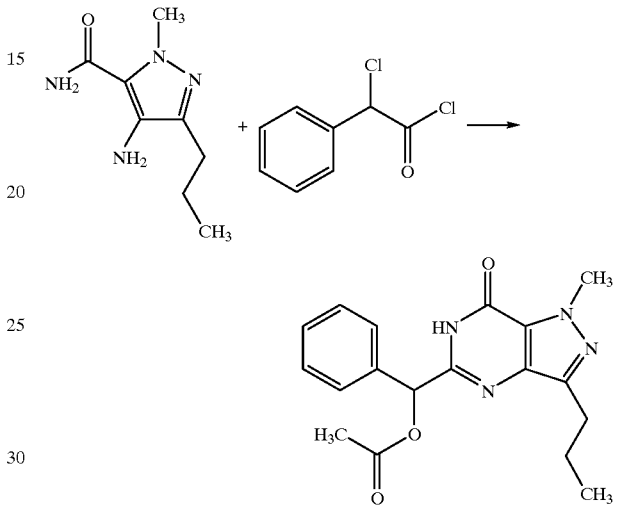

2-chloro-2-phenylacetyl chloride (3.47 ml, 0.022 mol) was added dropwise to a solution of 4-amino-3-propyl-1-methyl-5-pyrazolecarboxamide (4 g, 0.022 mol) in acetic acid (30 ml) and the reaction stirred at reflux under a nitrogen atmosphere for 20 hours.

On cooling, the mixture was concentrated under reduced pressure and purified by flash column chromatography eluting with dichloromethane. Trituration with diethyl ether gave the title compound (633 mg), m.p.161–163° C.

Found: C, 63.37; H, 5.84; N, 16.07; C$_{18}$H$_{20}$N$_4$O$_3$, requires C, 63.51; H, 5.92; N, 16.46%

$^1$H-NMR (CDCl$_3$): d=1.01 (t, 3H), 1.82 (m, 2H), 2.30 (s, 3H), 2.90 (t, 2H), 4.24 (s, 3H), 6.74 (s, 1H), 7.40 (m, 3H), 7.50 (m, 2H), 9.88 (s, 1H) ppm.

Example 78

5-[α-hydroxybenzyl]-1-methyl-3-propyl-6,7-dihydro-1H-pyrazolo[4,3-d]pyrimidin-7-one

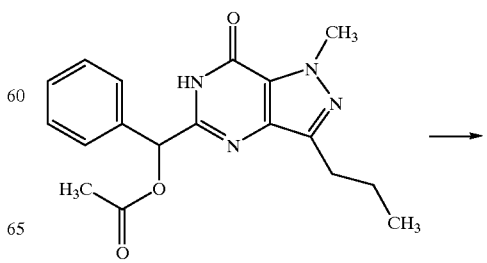

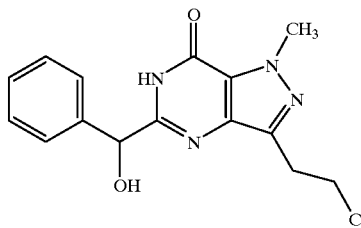

(1-methyl-7-oxo-3-propyl-6,7-dihydro-1H-pyrazolo[4,3-d]pyrimidin-5-yl)(phenyl)methyl acetate (1.311 g, 0.004 mol) was added to a solution of potassium hydroxide (232 mg, 0.0041 mol) in ethanol (60 ml). The resulting mixture was refluxed for 1 hour to give a colourless solution. On cooling, this was concentrated under reduced pressure, and the resulting residue partitioned between water and dichloromethane. The aqueous phase was acidified to pH3 with 1M aqueous hydrochloric acid solution and was extracted with dichloromethane/methanol (100 ml). The organic extracts were combined, dried (MgSO$_4$), filtered and concentrated under reduced pressure.

Purification by flash column chromatography eluting with dichloromethane:methanol (95:5 by volume), followed by crystallisation from acetone/hexane, gave the title compound (50 mg), m.p.164–165° C.

Found: C, 64.29; H, 6.10; N, 19.24; C$_{16}$H$_{18}$N$_4$O$_2$ requires C, 64.41; H, 6.08; N, 18.78%.

$^1$H-NMR (CDCl$_3$): δ=1.05 (t, 3H), 1.85 (m, 2H), 2.90 (t, 2H), 4.05 (s, 1H), 4.25 (s, 3H), 5.65 (d, 1H), 7.40 (m, 3H), 7.50 (m, 2H), 9.45 (s, 1H) ppm.

Example 79

(1-methyl-7-oxo-3-propyl-6,7-dihydro-1H-pyrazolo[4,3-d]pyrimidin-5-yl)(phenyl)methanone

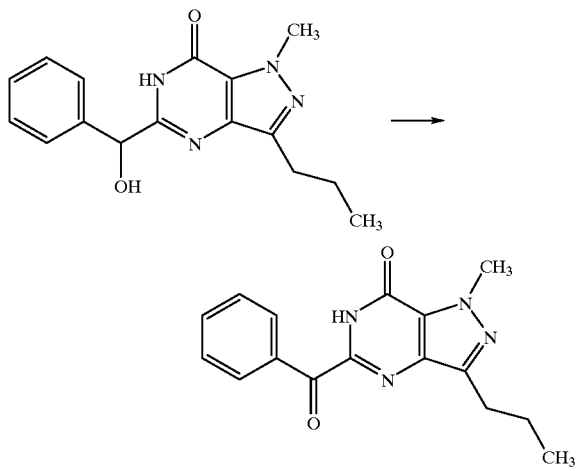

Pyridinium chlorochromate (400 mg, 0.00186 mol) was added to a solution of 5-[α-hydroxybenzyl]-1-methyl-3-propyl-6,7-dihydro-1H-pyrazolo[4,3-d]pyrimidin-7-one (200 mg, 0.00068 mol) in dichloromethane (50 ml) and the reaction stirred at room temperature for 3 hours.

The reaction mixture was filtered through silica gel, eluting with dichloromethane:methanol (95:5 by volume). Evaporation under reduced pressure of the desired fractions followed by crystallisation from ethyl acetate/hexane, gave the title compound as yellow needles (110 mg), m.p.172–173° C.

Found: C, 64.81; H, 5.56; N, 18.95; C$_{16}$H$_{16}$N$_4$O$_2$, requires C, 64.85; H, 5.44; N, 18.91%.

$^1$H-NMR (CDCl$_3$): δ=1.05 (t, 3H), 1.90 (m, 2H), 2.95 (t, 2H), 4.35 (s, 3H), 7.55 (m, 2H), 7.70 (m, 1H), 8.50 (d, 2H) 10.15 (s, 1H) ppm.

Synthesis Preparations

Preparation 1

N-(5-carbamoyl-1-methyl-3-propyl-1H-4-pyrazolyl)-2-(4-bromophenyl)acetamide

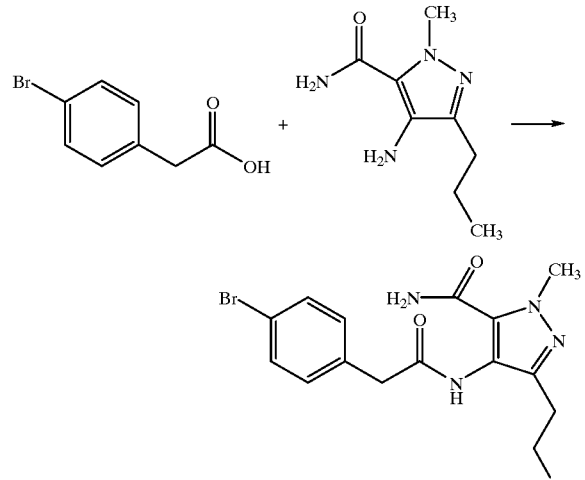

Oxalyl chloride (7.5 ml, 0.86 mol) was added dropwise to a solution of 4-bromophenylacetic acid (8.5 g, 0.040 mol) and dimethylformamide (3 drops) in dichloromethane and the reaction stirred at room temperature for 4 hours. The reaction mixture was then concentrated under reduced pressure and azeotroped with dichloromethane (30 ml).

A solution of this 4-bromophenylacetyl chloride in dry dichloromethane (5 ml) was then added dropwise to a solution of 4-amino-1-methyl-3-propyl-1H-5-pyrazolecarboxamide (6 g, 0.033 mol) and triethylamine (7 ml, 0.050 mol) in dichloromethane (250 ml), and the reaction stirred at room temperature for 18 hours.

The reaction mixture was concentrated under reduced pressure and the residue triturated with 1N aqueous hydrochloric acid solution. The resulting precipitate was filtered and washed with water (50 ml) and ether (50 ml). Recrystallisation from ethanol gave the title compound as a solid (6.48 g), m.p.241–243° C.

Found: C, 50.38; H, 5.00; N, 14.59%; $C_{16}H_{19}N_4BrO_2$, requires C, 50.67; H, 5.05; N, 14.77%.

$^1$H-NMR (DMSO-$d_6$): d=0.78 (t, 3H), 1.40 (m, 2H), 2.27 (t, 2H), 3.62 (s, 2H), 3.86 (s, 3H), 7.19 (s, 1H), 7.28 (d, 2H), 7.52 (d, 2H), 7.70 (s, 1H), 9.44 (s, 1H) ppm.

Preparations 2 to 22

The compounds of the following tabulated preparations of the general formula:

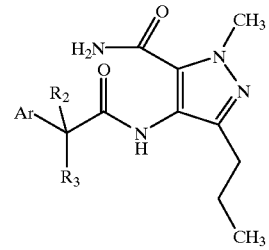

were prepared from 4-amino-1-methyl-3-propyl-1H-5-pyrazolecarboxamide and the appropriate acid chloride using similar methods to that described in Preparation 1.

| Prep. No | $R_1$ | $Ar(R_2)(R_3)C-$ | Analysis/$^1$H-NMR/Melting point/Crystallisation solvent |
|---|---|---|---|
| 2 | —$CH_3$ | benzyl (PhCH$_2$—) | Found: C, 64.01; H, 6.72; N, 18.35%<br>$C_{16}H_{20}N_4O_2$, requires C, 63.98; H, 6.71; N, 18.65%.<br>$^1$H-NMR(DMSO-$d_6$): d = 0.76(t, 3H), 1.40(m, 2H), 2.26(t, 2H), 3.60(s, 2H), 3.87(s, 3H), 7.20–7.34(m, 6H), 7.70(s, 1H), 9.45(s, 1H)ppm<br>Melting point: 238–240° C.<br>Crystallisation solvent:ethanol. |
| 3 | —$CH_2CH_3$ | benzyl | Found: C, 65.00; H, 7.04; N, 17.76%<br>$C_{17}H_{22}N_4O_2$, requires C, 64.94; H, 7.05; N, 17.82%.<br>$^1$H-NMR(CDCl$_3$): d = 0.72(t, 3H), 1.24(t, 3H), 1.34(m, 2H), 2.27(t, 2H), 3.58(s, 2H), 4.24(q, 2H), 6.02(s, 1H), 7.20(m, 5H), 8.58(s, 1H)ppm.<br>Melting point: 191–192° C.<br>Crystallisation solvent:ethanol. |
| 4 | —$CH_3$ | PhCH(CH$_3$)— | Found: C, 64.76; H, 7.05; N, 17.62%<br>$C_{17}H_{22}N_4O_2$, requires C, 64.94; H, 7.05; N, 17.82%.<br>$^1$H-NMR(CDCl$_3$): d = 0.82(t, 3H), 1.40(m, 2H), 1.66(d, 3H), 2.24(t, 2H), 3.82(q, 1H), 4.00(s, 3H), 5.52(s, 1H), 6.60(s, 1H), 7.28(s, 1H), 7.40(m, 5H)ppm.<br>Melting point: 213–215° C.<br>Crystallisation solvent:ethyl acetate/methanol |
| 5 | —$CH_3$ | PhC(CH$_3$)$_2$— | Found: C, 65.79; H, 7.39; N, 16.85%<br>$C_{18}H_{24}N_4O_2$, requires C, 65.83; H, 7.37; N, 17.06%.<br>$^1$H-NMR(CDCl$_3$): d = 0.84(t, 3H), 1.42(m, 2H), 1.72(s, 6H), 2.25(t, 2H), 4.00(s, 2H), 6.05(s, 1H), 6.42(s, 1H), 7.42(m, 6H) ppm<br>Melting point: 192–193° C.<br>Crystallisation solvent:ethanol. |

-continued

| Prep. No | R₁ | Ar(R₂)(R₃)C— | Analysis/¹H-NMR/Melting point/Crystallisation solvent |
|---|---|---|---|
| 6 | —CH₃ | 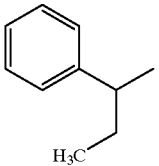 | Found: C, 65.87; H, 7.37; N, 17.05%<br>C₁₈H₂₄N₄O₂, requires C, 65.83; H, 7.37; N, 17.06%.<br>¹H-NMR(CDCl₃): d = 0.70(t, 3H), 0.88(t, 3H), 1.34(m, 2H), 1.76(m, 1H), 2.13(m, 1H), 2.22(t, 2H), 3.50(t, 1H), 3.92(s, 3H), 5.79(s, 1H), 7.20–7.35(m, 6H), 8.57(s, 1H)ppm.<br>Melting point: 226–227° C.<br>Crystallisation solvent:ethyl acetate/methanol |
| 7 | —CH₃ | 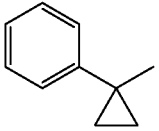 | Found: C, 66.42; H, 6.79; N, 17.39%.<br>C₁₈H₂₂N₄O₂, requires C, 66.24; H, 6.79; N, 17.17%<br>¹H-NMR(CDCl₃): d = 0.85(t, 3H), 1.28(m, 2H), 1.45(m, 2H), 1.72(m, 2H), 2.34(t, 2H), 4.00(s, 3H), 5.60(s, 1H), 6.62(s, 1H), 7.50(m, 5H), 7.89(s, 1H)ppm.<br>Melting point: 176–177° C.<br>Crystallisation solvent:ethanol. |
| 8 | —CH₃ | 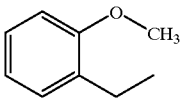 | Found C, 62.14, H, 6.71; N, 16.78%<br>C₁₇H₂₂N₄O₃, requires C, 61.80; H, 6.71; N, 16.96%.<br>¹H-NMR(CDCl₃): d = 0.82(t, 3H), 1.46(m, 2H), 2.30(t, 2H), 3.78(s, 2H), 3.94(s, 3H), 4.00(s, 3H), 5.64(s, 1H), 7.04(m, 2H), 7.35(m, 2H), 7.50(s, 1H)ppm.<br>Melting point: 208–209° C.<br>Crystallisation solvent:ethyl acetate/methanol |
| 9 | —CH₃ | 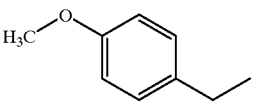 | Found: C, 61.43; H, 6.57; N, 16.94%<br>C₁₇H₂₂N₄O₃, requires C, 61.80; H, 6.71; N, 16.96%.<br>¹H-NMR(DMSO-d₆): d = 0.77(t, 3H), 1.40(m, 2H), 2.26(t, 2H), 3.54(s, 2H), 3.73(s, 3H), 3.86(s, 3H), 6.88(d, 2H), 7.22(m, 3H), 7.70(s, 1H), 9.39(s, 1H)ppm.<br>Melting point: 214–216° C.<br>Crystallisation solvent:ethyl acetate/methanol. |
| 10 | —CH₃ | 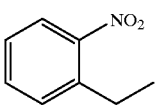 | Found: C, 55.31, H, 5.59; N, 20.49%<br>C₁₆H₁₉N₅O₄, requires C, 55.64; H, 5.55; N, 20.28%.<br>¹H-NMR(DMSO-d₆): d = 0.98(t, 3H), 1.53(m, 2H), 2.35(t, 2H), 3.88(s, 3H), 4.12(s, 2H), 7.11(s, 1H), 7.5(m, 2H), 7.72(m, 2H), 8.06(d, 1H), 9.50(s, 1H)ppm.<br>Melting point: 229–231° C. |
| 11 | —CH₃ | 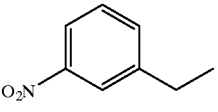 | Found: C, 55.82; H, 5.60; N, 20.53%<br>C₁₆H₁₉N₅O₄, requires C, 55.64; H, 5.55; N, 20.28%.<br>¹H-NMR(DMSO-d₆): d = 0.75(t, 3H), 1.41(m, 2H), 2.28(t, 2H), 3.82(s, 2H), 3.86(s, 3H), 7.20(s, 1H), 7.66(m, 2H), 7.78(d, 1H), 8.14(d, 1H), 8.12(s, 1H), 9.57(s, 1H)ppm.<br>Melting point: .238–240° C. |

-continued

| Prep. No | R₁ | Ar(R₂)(R₃)C— | Analysis/¹H-NMR/Melting point/Crystallisation solvent |
|---|---|---|---|
| 12 | —CH₃ | 4-O₂N-C₆H₄-CH₂CH₂CH₂- | Found: C, 55.97; H, 5.60; N, 20.10%<br>$C_{16}H_{19}N_5O_4$, requires C, 55.64; H, 5.55; N, 20.28%.<br>¹H-NMR(DMSO-d₆): d 0.78(t, 3H), 1.42(m, 2H), 2.28(t, 2H), 3.82(s, 2H), 3.86(s, 3H), 7.18(s, 1H), 7.60(d, 2H), 7.70(s, 1H), 8.20(d, 2H), 9.57(s, 1H)ppm.<br>Melting point: 261–263° C.<br>Crystallisation solvent:ethyl acetate/methanol. |
| 13 | —CH₃ | 2-Br-C₆H₄-CH₂CH₂CH₂- | Found: C, 50.59; H, 4.99; N, 14.85%<br>$C_{16}H_{19}N_4BrO_2$, requires C, 50.67; H, 5.05; N, 14.77%<br>H-NMR(DMSO-d₆): d = 0.85(t, 3H), 1.52(m, 2H), 2.36(t, 2H), 3.82(s, 2H), 3.88(s, 3H), 7.20(m, 2H), 7.34(m, 1H), 7.41(d, 1H), 7.60(d, 1H), 7.76(s, 1H), 9.45(s, 1H)ppm.<br>Melting point: 250–252° C.<br>Crystallisation solvent:acetonitrile. |
| 14 | —CH₃ | 3-Br-C₆H₄-CH₂CH₂CH₂- | Found: C, 50.49; H, 5.04; N, 14.99%<br>$C_{16}H_{19}N_4BrO_2$, requires C, 50.67; H, 5.05; N, 14.77%<br>¹H-NMR(DMSO-d₆): d = 0.87(t, 3H), 1.41(m, 2H), 2.26(t, 2H), 3.62(s, 2H), 3.86(s, 3H), 7.21(s, 1H), 7.30(m, 2H), 7.46(m, 1H), 7.72(s, 1H), 9.47(s, 1H)ppm.<br>Melting point: 240–242° C.<br>Crystallisation solvent:acetonitrile. |
| 15 | —CH₃ | 4-Br-C₆H₄-CH(CH₃)CH₂CH₂- | Found: C, 51.78; H, 5.40; N, 14.15%<br>$C_{17}H_{21}N_4BrO_2$, requires C, 51.92; H, 5.38; N, 14.25%.<br>¹H-NMR(DMSO-d₆): d = 0.70(t, 3H), 1.30(m, 2H), 1.38(d, 3H), 2.16(t, 2H), 3.86(s, 3H), 7.12(s, 1H), 7.73(d, 2H), 7.52(d, 2H), 7.69(s, 1H), 9.35(s, 1H)ppm.<br>Melting point: 234–236° C.<br>Crystallisation solvent:ethyl acetate/methanol. |
| 16 | —CH₃ | 4-Cl-C₆H₄-CH₂CH₂CH₂- | ¹H-NMR(DMSO-d₆): d = 0.76(t, 3H), 1.40(m, 2H), 2.28(t, 2H), 3.62(s, 2H), 3.88(s, 3H), 7.18(s, 1H), 7.35(m, 4H), 7.70(s, 1H), 9.46(s, 1H)ppm.<br>Crystallisation solvent:acetonitrile. |
| 17 | —CH₃ | 2-CF₃-C₆H₄-CH₂CH₂CH₂- | Found: C, 55.65; H, 5.28; N, 14.94%<br>$C_{17}H_{19}N_4F_3O_2$, requires C, 55.43; H, 5.20; N, 15.21%.<br>¹H-NMR(DMSO-d₆): d = 0.87(t, 3H), 1.32(m, 2H), 2.34(t, 2H), 3.86(s, 3H), 3.92(s, 2H), 7.18(s, 1H), 7.50(m, 2H), 7.70(m, 3H), 9.45(s, 1H)ppm.<br>Melting point: 247–249° C.<br>Crystallisation solvent:acetonitrile. |

| Prep. No | $R_1$ | $Ar(R_2)(R_3)C-$ | Analysis/$^1$H-NMR/Melting point/Crystallisation solvent |
|---|---|---|---|
| 18 | —CH$_3$ | 4-CF$_3$-benzyl | Found: C, 55.63; H, 5.24; N, 15.11% <br> C$_{17}$H$_{19}$N$_4$F$_3$O$_2$, requires C, 55.43; H, 5.20; N, 15.21%. <br> $^1$H-NMR(DMSO-d$_6$): d = 0.76(t, 3H), 1.39(m, 2H), 2.26(t, 2H), 3.75(s, 2H), 3.86(s, 3H), 7.22(s, 1H), 7.55(d, 2H), 7.70(m, 3H), 9.52(s, 1H)ppm. <br> Melting point: 225–228° C. <br> Crystallisation solvent:ethyl acetate/methanol. |
| 19 | —CH$_3$ | 4-isopropyl-benzyl | Found: C, 66.99; H, 7.47; N, 16.35% <br> C$_{19}$H$_{26}$N$_4$O$_2$, requires C, 66.64; H, 7.65; N, 16.36%. <br> $^1$H-NMR(DMSO-d$_6$): d = 0.75(t, 3H), 1.18(d, 6H), 1.38(m, 2H), 2.25(t, 2H), 2.86(m, 1H), 3.57(s, 2H), 3.86(s, 3H), 7.22(m, 5H), 7.72(s, 1H), 9.42(s, 1H)ppm. <br> Melting point: 200–201° C. <br> Crystallisation solvent:ethyl acetate |
| 20 | —CH$_3$ | 4-acetyl-benzyl | $^1$H-NMR(DMSO-d$_6$): d = 0.74(t, 3H), 1.40(m, 2H), 2.25(t, 2H), 2.57(s, 3H), 3.72(s, 2H), 3.85(s, 3H), 7.47(d, 2H), 7.92(d, 2H), 9.52(s, 2H)ppm. |
| 21 | —CH$_3$ | 4-bromo-2-nitro-benzyl | Found: C, 45.35; H, 4.32; N, 16.26% <br> C$_{16}$H$_{18}$N$_5$BrO$_4$, requires C, 45.29; H, 4.28; N,16.57%. <br> $^1$H-NMR(DMSO-d$_6$): d = 0.88(t, 3H), 1.52(m, 2H), 2.33(t, 2H), 3.86(s, 3H), 4.08(s, 2H), 7.08(s, 1H), 7.54(d, 1H), 7.73(s, 1H), 7.92(d, 1H), 8.24(s, 1H), 9.49(s, 1H)ppm. <br> Melting point: 249–251° C. <br> Crystallisation solvent:acetonitrile. |
| 22 | —CH$_3$ | 4-bromomethyl-benzyl | Found: C, 52.02; H, 5.45; N, 14.48% <br> C$_{17}$H$_{21}$N$_4$BrO$_2$, requires C, 51.91; H, 5.38; N, 14.25%. <br> $^1$H-NMR(DMSO-d$_6$): d = 0.78(t, 3H), 1.40(m, 2H), 2.26(t, 2H), 3.62(s, 2H), 3.85(s, 3H), 4.70(s, 2H), 7.22(s, 1H), 7.30(d, 2H), 7.40(d, 2H), 7.62(s, 1H), 9.45(s, 1H)ppm. <br> Melting point: 191–193° C. <br> Crystallisation solvent:acetonitrile. |

Preparation 23

4-tert-butyl carbamoylmethoxyphenyl acetic acid methyl ester

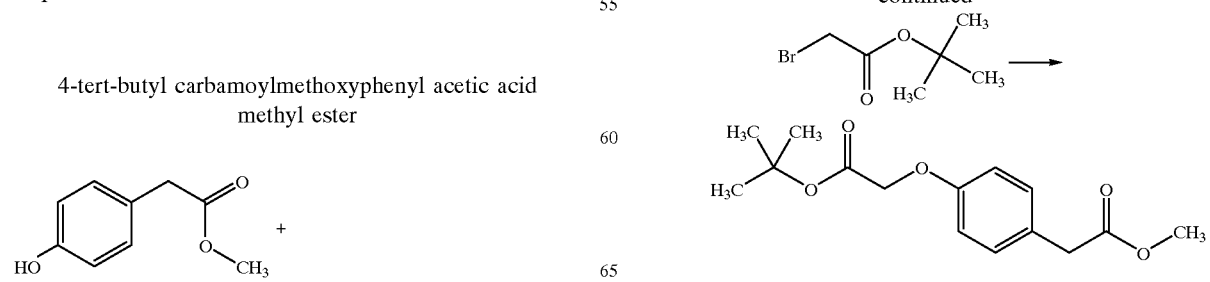

Methyl 4-hydroxyphenylacetate (4.1 g, 0.0247 mol) was added to a suspension of sodium hydride (800 mg, 80%, 0.0266 mol) in dimethylformamide (100 ml) and the mixture stirred at room temperature for 30 minutes. Tert-butyl bromoacetate (4.2 ml, 0.0258 mol) was added dropwise and the resulting solution stirred for a further 2 hours. Water (250 ml) and 1N aqueous hydrochloric acid (100 ml) were then added and the mixture extracted with diethyl ether (2×250 ml). The combined organic extracts were dried (MgSO$_4$), filtered and evaporated under reduced pressure.

Purification by flash column chromatography, eluting with dichloromethane gave the title compound as a colourless liquid (5.67 g).

Found: C, 64.20; H, 7.13; C$_{15}$H$_{20}$O$_5$, requires C, 64.27; H, 7.13%.

$^1$H-NMR (CDCl$_3$): d=1.52 (s, 9H), 3.59 (s, 2H), 3.72 (s, 3H), 4.54 (s, 2H), 6.88 (d, 2H), 7.24 (d, 2H) ppm.

Preparation 24

4-(1-methyl piperidinoxy)-phenylacetic acid methyl ester

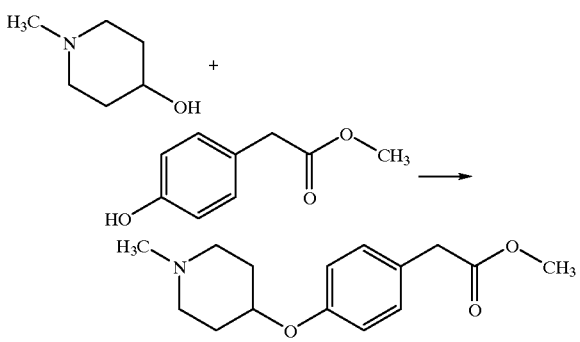

Diethylazodicarboxylate (2.1 ml, 0.013 mol) was added dropwise to a solution of methyl 4-hydroxyphenylacetate (2.2 g, 0.013 mol), 4-hydroxy-1-methylpiperidine (1.5 g, 0.013 mol) and triphenylphosphine (3.5 g, 0.0133 mol) in tetrahydrofuran (50 ml) and the reaction stirred at room temperature for 20 hours. The reaction mixture was then concentrated under reduced pressure.

Purification by flash column chromatography eluting with 0.880 aqueous ammonia:methanol:dichloromethane (0.5:5:95 by volume) gave the title compound as an oil (1.48 g).

$^1$H-NMR (CDCl$_3$): d=1.88 (m, 2H), 2.02 (m, 2H), 2.32 (m, 5H), 2.72 (m, 2H), 3.58 (s, 2H), 3.72 (s, 3H), 4.32 (m, 1H), 6.88 (d, 2H), 7.20 (d, 2H) ppm.

Preparation 25

4-tert-butyl carbamoylmethoxyphenyl acetic acid

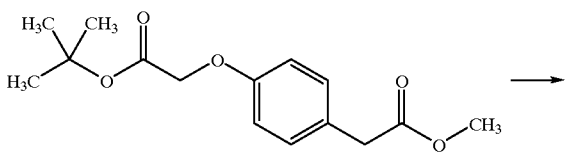

-continued

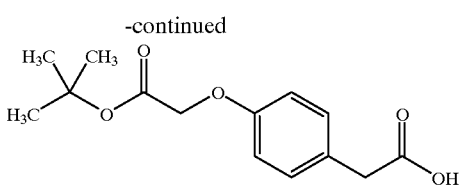

1N aqueous sodium hydroxide solution (16 ml) was added to a solution of 4-tert-butyl carbamoylmethoxyphenylacetic acid methyl ester (2.8 g, 0.010 mol) in methanol (10 ml) and the reaction stirred at room temperature for 5 hours. The reaction mixture was then concentrated under reduced pressure, the residue suspended in 1N aqueous hydrochloric acid (20 ml) and extracted with diethyl ether (2×25 ml). The combined organic extracts were dried (MgSO$_4$), filtered and evaporated under reduced pressure.

Purification by flash column chromatography, eluting with a solvent gradient of diethyl ether:hexane (50:50 to 67:33 by volume) gave the title compound as a solid (680 mg), m.p.97–98° C.

Found: C, 62.74; H, 6.89; C$_{14}$H$_{18}$O$_5$, requires C, 63.14; H, 6.81%.

$^1$H-NMR (CDCl$_3$): d=1.54 (s, 9H), 3.62 (s, 2H), 4.54 (s, 2H), 6.88 (d, 2H), 7.24 (d, 2H) ppm.

Preparation 26

4-(1-methyl piperidinoxy)-phenylacetic acid

The title compound was prepared using a similar method to that described in Preparation 25 from 4-(1-methyl piperidinoxy)-phenylacetic acid methyl ester and was obtained, after trituration with acetonitrile, as a solid (82%), m.p.159–161° C.

Found: C, 67.48; H, 7.65; N, 5.57; C$_{14}$H$_{19}$NO$_3$, requires C, 67.44; H, 7.68; N, 5.62%.

$^1$H-NMR (DMSO-d$_6$): d=1.62 (m, 2H), 1.88 (m, 2H), 2.18 (m, 5H), 2.60 (m, 2H), 3.48 (s, 2H), 4.30 (m, 1H), 6.84 (d, 2H), 7.15 (d, 2H) ppm.

Preparation 27 tert-butyl-2-(4-{[5-carbamoyl-1-methyl-3-propyl-1H4-pyrazolyl)carbamoyl]methyl}phenoxy)acetate

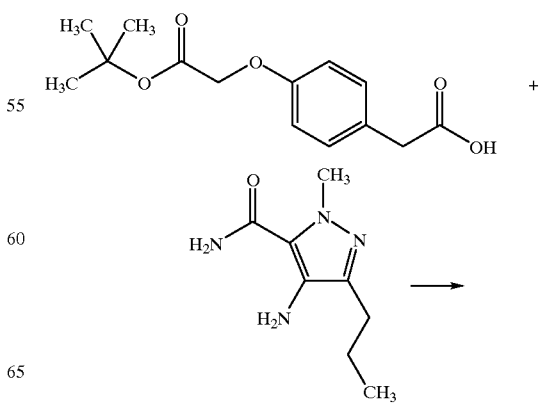

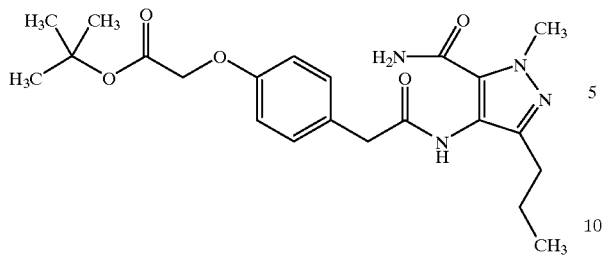

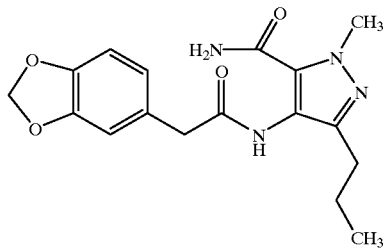

Phosphorous trichloride (141 mg, 0.0010 mol) was added dropwise to an ice-cooled solution of 4-amino-1-methyl-3-propyl-1H-5-pyrazolecarboxamide (370 mg, 0.0020 mol) in pyridine (6 ml), and the reaction stirred for an hour at room temperature. 4-tert-butyl carbamoylmethoxy-phenyl acetic acid (600 mg, 0.0023 mol) was then added and stirring continued at reflux for 3 hours. On cooling, the mixture was concentrated under reduced pressure.

Purification by flash column chromatography eluting with a solvent gradient of methanol:dichloromethane (2:98 to 5:95 by volume), followed by crystallisation from ethyl acetate/hexane gave the title compound as a solid (465 mg), m.p.145–146° C.

Found: C, 61.07; H, 6.97; N, 12.76; $C_{22}H_{30}N_4O_5$ requires C, 61.38; H, 7.02; N, 13.02%.

$^1$H-NMR (CDCl$_3$): d=0.88 (t, 3H), 1.52 (m, 11H), 2.34 (t, 2H), 3.74 (s, 2H), 4.01 (s, 3H), 4.57 (s, 2H), 5.58 (s, 2H), 6.70 (s, 1H), 6.97 (d, 2H), 7.29 (d, 2H) ppm.

Preparation 28

N-(5-carbamoyl-1-methyl-3-propyl-1H-4-pyrazolyl)-2-[4-(1-methylpiperidinoxy]acetamide The title compound was prepared from 4-(1-methyl piperidinoxy)-phenylacetic acid following the procedure described in Preparation 27 and was obtained as a solid (47%), m.p. 170–171° C.

Found: C, 63.59; H, 7.62; N, 16.87; $C_{22}H_{31}N_5O_3$, requires C, 63.90; H, 7.56; N, 16.94%.

$^1$H-NMR (CDCl$_3$): d=0.87 (t, 3H), 1.48 (m, 2H), 1.88 (m, 2H), 2.04 (m, 2H), 2.33 (m, 7H), 2.72 (m, 2H), 3.73 (s, 2H), 4.00 (s, 3H), 4.36 (m, 1H), 5.56 (s, 1H), 6.68 (s, 1H), 6.98 (d, 2H), 7.26 (d, 2H), 7.54 (s, 1H) ppm.

Preparation 29

N-(5-carbamoyl-1-methyl-3-propyl-1H-4-pyrazolyl)-2-(1,3-benzodioxol-5-yl)acetamide

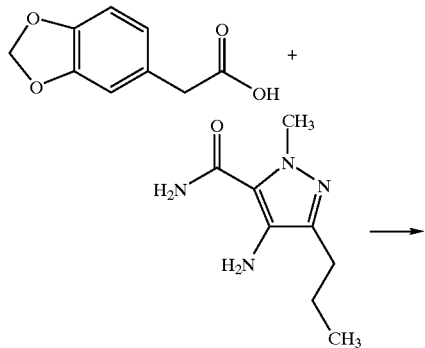

Oxalyl chloride (0.6 ml, 0.0067 mol) was added dropwise to a solution of 3,4-methylenedioxyphenylacetic acid (600 mg, 0.0033 mol) and dimethylformamide (1 drop) in dichloromethane and the reaction stirred at room temperature for 2 hours. The reaction mixture was concentrated under reduced pressure, and azeotroped with dichloromethane (40 ml).

This acid chloride was added to a solution of 4-amino-1-methyl-3-propyl-1H-5-pyrazolecarboxamide (550 mg, 0.0030 mol) in pyridine (6 ml) and the reaction stirred at room temperature for 18 hours. The reaction mixture was then concentrated under reduced pressure.

Purification by flash column chromatography, eluting with a solvent gradient of methanol:dichloromethane (2:98 to 5:95 by volume), followed by crystallisation from acetonitrile gave the title compound (420 mg), m.p.231–233° C.

Found: C, 59.25; H, 5.79; N, 16.62; $C_{17}H_{20}N_4O_4$, requires C, 59.29; H, 5.85; N, 16.27%.

$^1$H-NMR (DMSO-d$_6$): d=0.78 (t, 3H), 1.40 (m, 2H), 2.26 (t, 2H), 3.52 (s, 2H), 3.86 (s, 3H), 5.98 (s, 2H), 6.78 (s, 1H), 6.86 (d, 2H), 7.18 (s, 1H), 7.70 (s, 1H), 9.37 (s, 1H) ppm.

Preparation 30

N-(5-carbamoyl-1-methyl-3-propyl-1H-4-pyrazolyl)-2-(4-phenoxyphenyl-5-yl)acetamide The title compound was prepared from 4-phenoxyphenylacetic acid and 4-amino-1-methyl-3-propyl-1H-5-pyrazolecarboxamide following the procedure described in Preparation 29 and was obtained as a solid (21%), m.p.192–194° C.

Found: C, 67.28; H, 6.20; N, 14.49; $C_{22}H_{24}N_4O_3$, requires C, 67.33; H, 6.16; N, 14.28%.

$^1$H-NMR (CDCl$_3$): d=0.89 (t, 3H), 1.52 (m, 2H), 2.36 (t, 2H), 3.78 (s, 2H), 4.02 (s, 3H), 5.57 (s, 1H), 6.71 (s, 1H), 7.08 (m, 4H), 7.18 (m, 1H), 7.36 (m, 5H) ppm.

Preparation 31

N-(5-carbamoyl-1-methyl-3-propyl-1H-4-pyrazolyl)-2-[4-(morpholinomethyl)phenyl]acetamide

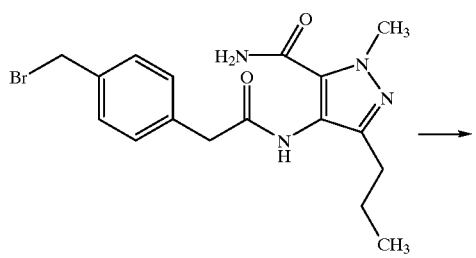

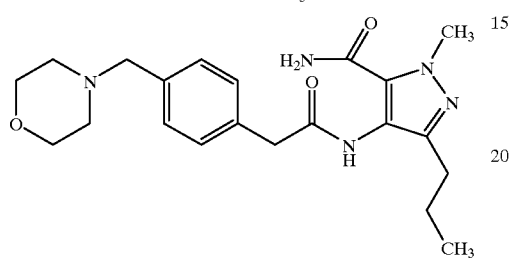

Morpholine (0.3 ml, 0.00344 mol) was added to a solution of N-(5-carbamoyl-1-methyl-3-propyl-1H-4-pyrazolyl)-2-(4-bromobenzyl)acetamide (400 mg, 0.001 mol) in acetonitrile (3 ml) and the reaction stirred at reflux for 2 hours. On cooling, the reaction was concentrated under reduced pressure.

Purification by flash column chromatography, eluting with a solvent gradient of 0.880 aqueous ammonia:methanol:dichloromethane (0:5:95 to 0.5:5:95 by volume), followed by crystallisation from ethyl acetate gave the title compound (350 mg), m.p.148–150° C.

Found: C, 63.48; H, 7.36; N, 17.16; $C_{21}H_{29}N_5O_3$, requires C, 63.12; H, 7.32; N, 17.53%.

$^1$H-NMR (CDCl$_3$): d=0.85 (t, 3H), 1.48 (m, 2H), 2.32 (t, 2H), 2.47 (m, 4H), 3.54 (s, 2H), 3.74 (m, 4H), 3.80 (s, 2H), 4.00 (s, 3H), 5.58 (s, 1H), 6.68 (s, 1H), 7.32 (d, 2), 7.44 (d, 2H), 7.50 (s, 1H) ppm.

Preparation 32 and 33

The compounds of the following tabulated preparations of the general formula:

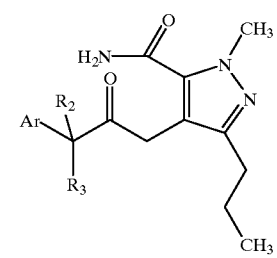

were prepared from N-(5-carbamoyl-1-methyl-3-propyl-1H-4-pyrazolyl)-2-(4-bromobenzyl)acetamide and the appropriate amine, using similar methods to that described in Preparation 31.

| Prep. No | Ar(R$_2$)(R$_3$)C— | Analysis/$^1$H-NMR/Melting point/Crystallisation solvent |
|---|---|---|
| 32 | H$_3$C—N(CH$_3$)—CH$_2$—C$_6$H$_4$—CH$_2$— | Found: C, 63.81; H, 7.64; N, 19.74% $C_{19}H_{27}N_5O_2$, requires C, 63.84; H, 7.61; N, 19.59%. $^1$H-NMR(CDCl$_3$): d = 0.86(t, 3H), 1.48(m, 2H), 2.28(m, 8H), 2.32(t, 2H), 3.47(s, 2H), 4.00(s, 3H), 5.58(s, 1H), 6.71(s, 1H), 7.32(d, 2H), 7.40(d, 2H), 7.50(s, 1H) ppm. Melting point: 184–186° C. Crystallisation solvent:ethyl acetate/hexane. |
| 33 | imidazol-1-yl-CH$_2$—C$_6$H$_4$—CH$_2$— | Found: C, 63.23; H, 6.24; N, 22.27% $C_{20}H_{24}N_6O_2$, requires C, 63.14; H, 6.36; N, 22.09%. $^1$H-NMR(DMSO-d$_6$): d = 0.74(t, 3H), 1.38(m, 2H), 2.24(t, 2H); 3.60(s, 2H), 3.84(s, 3H), 5.16(s, 2H), 6.88(s, 1H), 7.16(s, 1H), 7.20(d, 2H), 7.30(d, 2H), 7.72(s, 1H), 9.42(s, 1H) ppm. Melting point: 222–224° C. Crystallisation solvent:ethanol. |

Preparation 34

N-(5-carbamoyl-1-methyl-3-propyl-1H-4-pyrazolyl)-
2-[4-(ethoxymethyl)phenyl]acetamide

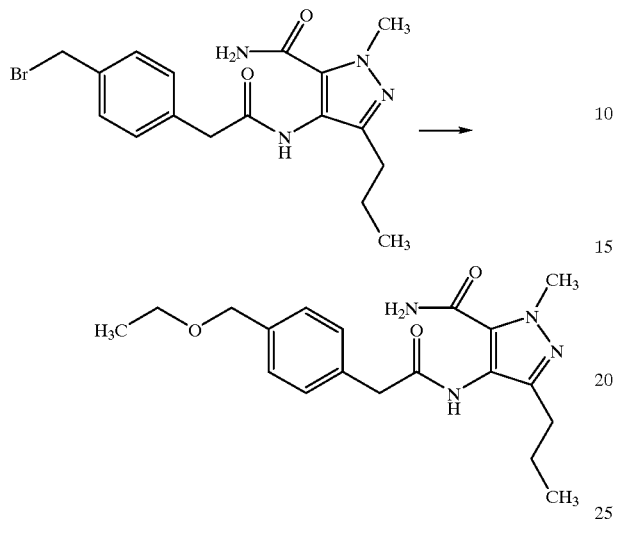

Silver nitrate (290 mg, 0.0017 mol) was added to a solution of N-(5-carbamoyl-1-methyl-3-propyl-1H-4-pyrazolyl)-2-(4-bromobenzyl)acetamide (600 mg, 0.0015 mol) in ethanol (5 ml) and the reaction stirred at reflux for 5 hours and then at room temperature for 18 hours.

Ethanol (10 ml) was added, the mixture filtered, and the solid washed with further ethanol.

The filtrate was evaporated under reduced pressure and the residue crystallised from ethanol to give the title compound, as a solid (500 mg).

Preparation 35

2-(4-bromophenyl)propionic acid

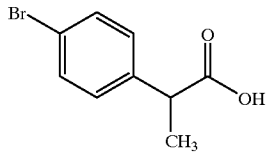

The title compound was prepared following a similar procedure to that described in *Synthesis* 1982; 456.

Preparation 36

4-acetyl phenylacetic acid

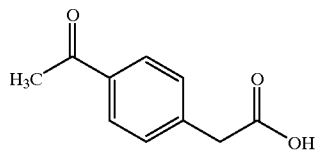

The title compound was prepared following a similar procedure to that described in *J.A.C.S.* 1946; 68; 2133.

Preparation 37

2-nitro-4-bromophenylacetic acid

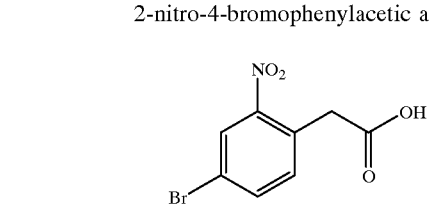

The title compound was prepared following a similar procedure to that described in *Chem. Pharm. Bull;* 1985; 33; 1414.

Preparation 38

3-pyridinesulphonyl chloride hydrochloride

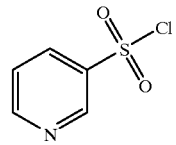

The title compound was prepared following a similar procedure to that described in *Annalen;* 1939; 72; 77.

Preparation 39

2-(methylaminomethyl)pyridine

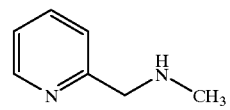

The title compound was prepared following a similar procedure to that described in U.S. Pat. No. 2798075.

Activity Studies

Initially there is presented a Protocol for measuring PDE inhibitory activity.

Protocol

Phosphodiesterase (PDE) Inhibitory Activity

In vitro PDE inhibitory activities against cyclic guanosine 3', 5'-monophosphate (cGMP) and cyclic adenosine 3', 5'-monophosphate (cAMP) phosphodiesterases can be determined by measurement of their $IC_{50}$ inhibition of enzyme activity.

The required PDE enzymes are isolated from a variety of sources, including rat kidney, human corpus cavernosum, human platelets, rabbit platelets, human cardiac ventricle, human skeletal muscle and bovine retina, essentially by the method of W J Thompson and M M Appleman (Biochem, 1971, 10, 311).

For example, for some of the studies the calcium/calmodulin (Ca/CAM)-dependent PDE (PDE1) is obtained from either human cardiac ventricle or rat kidney. The cGMP-stimulated PDE (PDE2), the cGMP-specific PDE (PDE5) and the cGMP-inhibited cAMP PDE (PDE3) are obtained from human corpus cavernosum tissue. PDE5 is also obtained from human platelets or rabbit platelets by techniques usual in the art. The cAMP-specific PDE (PDE4) is obtained from rat kidney. The photoreceptor PDE (PDE6) is obtained from bovine retina.

Assays are performed using a modification of the "batch" method of W J Thompson et al (Biochem, 1979, 18, 5228).

Results

The compounds of the present invention were tested for PDE inhibition. The results showed that the compounds are inhibitors of at least Ca/CAM-dependent PDE1. Some of the compounds are selective and potent inhibitors of Ca/CAM-dependent PDE1.

In particular, we found the following results for a preferred compound of the present invention having the formula:

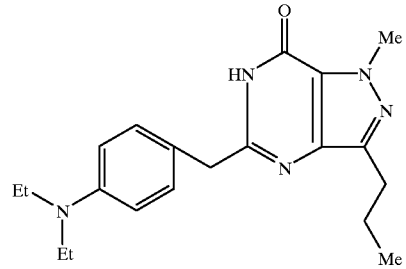

which for ease of reference is referred to as the Example 50 compound.

| | Example 50 | |
|---|---|---|
| PDE TYPE | SOURCE | $IC_{50}$ |
| 1 | Human cardiac ventricle | 38 nM |
| 2 | Human corpus cavernosum | 1.99 μM |
| 3 | Human corpus cavernosum | 3.94 μM |
| 4 | Rat Kidney | 23 μM |
| 5 | Human corpus cavernosum | 2.49 μM |
| 6 | Bovine retina | 2.03 μM |

(IC denotes inhibitory concentration)

Comparative Activity Studies

For these studies we compared the activity of the '188 compound with the Example 50 compound.

The results are as follows:

| SOURCE | EXAMPLE 50 | '188 COMPOUND |
|---|---|---|
| | cGMP / PDE1 INHIBITION - $IC_{50}$ Values | |
| Rat Kidney | 37 nM | 9.9 μM |
| | PDE5 INHIBITION - $IC_{50}$ Values | |
| Rabbit Platelet | 6.7 μM | 2.8 μM |
| Human Platelet | 2.7 μM | 3.2 μM |

Further Studies

In addition, we investigated the following two compounds.

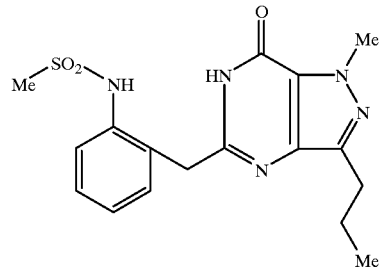

(which for ease of reference is referred to as the Example 36 compound)

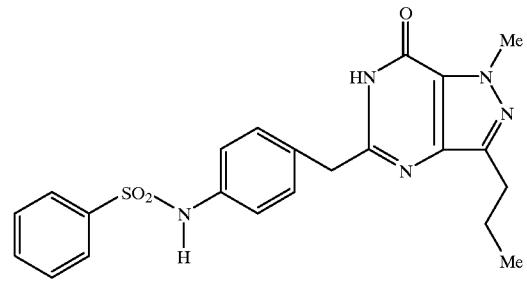

(which for ease of reference is referred to as the Example 37 compound)

The results of these additional studies are presented below.

| EXAMPLE No | RAT KIDNEY PDE1 | RABBIT PLATELET PDE5 |
|---|---|---|
| EXAMPLE 36 | 59 nM | 1.8 μM |
| EXAMPLE 37 | 94 nM | 6.4 μM |

Summary of Results

The results demonstrate that the compounds of the present invention—especially the Example 50, the Example 36 and the Example 37 compounds presented above—are potent and selective PDE1 inhibitors.

Other modifications will be apparent to those skilled in the art.

What is claimed is:

1. A compound of the formula (I)

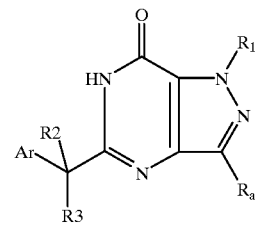

wherein
$R_a$ is $C_3$–$C_6$ alkyl;
$R_1$ is H or $C_1$–$C_4$ alkyl;
each of $R_2$ and $R_3$ is independently selected from H and $C_1$–$C_4$ alkyl, or $R_2$ is H or $C_1$–$C_4$ alkyl and $R_3$ is OH, $C_2$–$C_4$ alkanoyloxy or fluoro, or $R_2$ and $R_3$ when taken together represent $C_2$–$C_6$ alkylene, or $R_2$ and $R_3$ when taken together with the carbon atom to which they are attached represent a carbonyl group;

Ar is either (a)

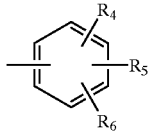

wherein each of $R_4$, $R_5$ and $R_6$ is independently selected from

H,
$C_1$–$C_4$ alkyl,
$C_1$–$C_4$ alkoxy,
$C_1$–$C_4$ alkoxy-Z—,
halo,
halo($C_1$–$C_4$)alkyl,
phenoxy, optionally substituted by up to three substitutents each of which substituent is independently selected from halo, $C_{1-4}$ alkyl, and $C_1$–$C_4$ alkoxy,
nitro,
hydroxy,
hydroxy-Z—,
$C_2$–$C_4$ alkanoyl,
amino,
amino-Z—,
($C_1$–$C_4$ alkyl)NH,
($C_1$–$C_4$ alkyl)$_2$N—,
($C_1$–$C_4$ alkyl)NH—Z—,
($C_1$–$C_4$ alkyl)$_2$N—Z—,
—COOH,
—Z—COOH,
—COO($C_1$–$C_4$ alkyl),
—Z—COO($C_1$–$C_4$ alkyl)
$C_1$–$C_4$ alkanesulphonamido,
$C_1$–$C_4$ alkanesulphonamido-Z—,
halo($C_1$–$C_4$)alkanesulphonamido,
halo($C_1$–$C_4$)alkanesulphonamido-Z—,
$C_1$–$C_4$ alkanamido,
$C_1$–$C_4$ alkanamido-Z—,
HOOC—Z—NH—,
HOOC—Z—NH—Z—,
($C_1$–$C_4$ alkyl)OOC—Z—NH—,
($C_1$–$C_4$ alkyl)OOC—Z—NH—Z—,
$C_1$–$C_4$ alkyl-NH—SO$_2$—NH—,
$C_1$–$C_4$ alkyl-NH—SO$_2$—NH—Z—,
($C_1$–$C_4$ alkyl)$_2$—N—SO$_2$—NH—,
($C_1$–$C_4$ alkyl)$_2$—N—SO$_2$—NH—Z—,
$C_1$–$C_4$ alkoxy CH═CH—Z—CONH—,
$C_1$–$C_4$ alkoxy CH═CHCONH
$C_1$–$C_4$ alkyl-SO$_2$—N($C_1$–$C_4$ alkyl)-,
$C_1$–$C_4$ alkyl-SO$_2$—N($C_1$–$C_4$ alkyl)—Z—,
($C_1$–$C_4$ alkyl)NH—Z—SO$_2$—NH—,
($C_1$–$C_4$ alkyl)$_2$N—Z—SO$_2$—NH—,
($C_1$–$C_4$ alkyl)NH—Z—SO$_2$—NH—Z—,
($C_1$–$C_4$ alkyl)$_2$N—Z—SO$_2$—NH—Z—,
benzenesulphonamido, optionally ring substituted by up to three substitutents each of which is independently selected from halo, $C_{1-4}$ alkyl, and $C_1$–$C_4$ alkoxy,
$C_1$–$C_4$ alkanoyl-N($C_1$–$C_4$ alkyl)-,
$C_1$–$C_4$ alkanoyl-N($C_1$–$C_4$ alkyl)-Z—,
$C_1$–$C_4$ alkoxycarbonyl-CH(CH$_2$OH)NHSO$_2$—,
—SO$_3$H,
—SO$_2$NH$_2$,
H$_2$NOC—CH(CH$_2$OH)—NHSO$_2$—,
HOOC—Z—O—, and
($C_1$–$C_4$ alkyl)OOC—Z—O—, or optionally one of $R_4$, $R_5$ and $R_6$ is a G-Het group and wherein the others of $R_4$, $R_5$ and $R_6$ are independently selected from the $R_4$, $R_5$ and $R_6$ subsituents listed above;

Z is $C_1$–$C_4$ alkylene,

G is a direct link, Z, O, —SO$_2$NH—, SO$_2$, or —Z—N($C_1$–$C_4$ alkyl)SO$_2$—, Het is a 5- or 6-membered heterocyclic group containing heteroatoms selected from the groups consisting of 1, 2, 3 or 4 nitrogen heteroatoms; and 1 or 2 nitrogen heteroatoms and 1 sulphur heteroatom or 1 oxygen heteroatom; or the heterocyclic group is furanyl or thiophenyl; wherein the Het group is saturated or partially or fully unsaturated and optionally substituted by up to 3 substituents, wherein each substituent is independently selected from $C_1$–$C_4$ alkyl, oxo, hydroxy, halo, and halo($C_1$–$C_4$) alkyl;

or (b) any one of the following bicyclic groups:

benzodioxolanyl,
benzodioxanyl,
benzimidazolyl,
quinolinyl,
indolyl,
quinazolinyl,
isoquinolinyl,
benzotriazolyl,
benzofuranyl,
benzothiophenyl,
quinoxalinyl, or
phthalizinyl, wherein said bicyclic Ar groups are linked to the neighbouring —C($R_2R_3$)— group via the benzo ring portion, and wherein the heterocyclic portion of said bicyclic Ar group is optionally partially or fully saturated, said group being optionally substituted by one or more of $C_1$–$C_4$ alkyl, halo, hydroxy, oxo, amino, and $C_1$–$C_4$ alkoxy;

or a pharmaceutically acceptable salt of the compound, or a pharmaceutically acceptable solvate of the compound or the salt.

2. A compound, salt or solvate according to claim 1 wherein $R_a$ is a $C_{2-5}$ alkyl group.

3. A compound, salt or solvate according to claim 2 wherein $R_a$ is a $C_{2-4}$ alkyl group.

4. A compound, salt or solvate according to claim 3 wherein $R_a$ is a $C_3$ alkyl group.

5. A compound, salt or solvate according to claim 1 wherein $R_1$ is a $C_{1-6}$ alkyl group.

6. A compound, salt or solvate according to claim 1 wherein $R_1$ is a $C_{1-3}$ alkyl group.

7. A compound, salt or solvate according to claim 6 wherein $R_1$ is a methyl group.

8. A compound, salt or solvate according to claim 1 wherein $R_2$ is H.

9. A compound, salt or solvate according to claim 1 wherein $R_3$ is H.

10. A compound, salt or solvate according to claim 1 wherein $R_4$, $R_5$ and $R_6$ are independently selected from H, $(C_{1-4}$ alkyl$)_2$N—, $C_{1-4}$ alkanesulphonamido and benzenesulphonamido.

11. A compound, salt or solvate according to claim 10 wherein $R_4$, $R_5$ and $R_6$ are independently selected from H, diethylamino, methanesulphonamido and benzenesulphonamido.

12. A compound, salt or solvate according to claim 1 wherein Ar is 4-diethylaminophenyl.

13. A compound, salt or solvate according to claims 1 wherein Ar is 2-methanesulphonamidophenyl.

14. A compound, salt or solvate according to claims 1 wherein Ar is 4-benzenesulphonamidophenyl.

15. A compound, salt or solvate according to claims 10 wherein one of $R_4$, $R_5$ and $R_6$ is $(C_{1-4}$ alkyl$)_2$N— and wherein the other two of $R_4$, $R_5$ and $R_6$ are H.

16. A compound, salt or solvate according to claim 15 wherein one of $R_4$, $R_5$ and $R_6$ is diethylamino and wherein the other two of $R_4$, $R_5$ and $R_6$ are H.

17. A compound, salt or solvate according to claim 1 wherein the compound is of the formula:

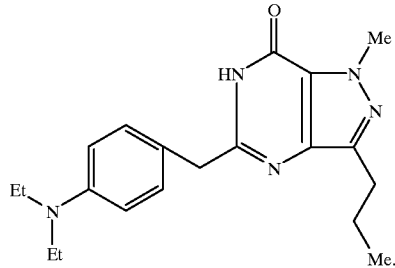

18. A compound, salt or solvate according to claim 1 wherein the compound is of the formula:

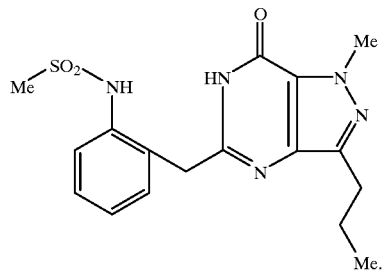

19. A compound, salt or solvate according to claim 1 wherein the compound is of the formula:

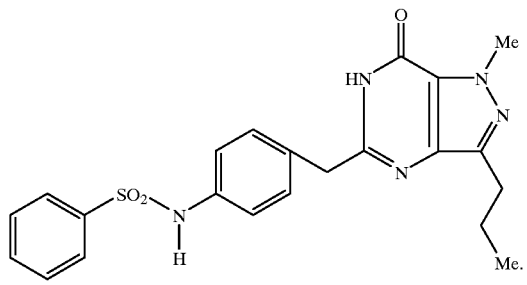

20. A pharmaceutical composition comprising a compound, salt or solvate according to claim 1 admixed with a pharmaceutically acceptable carrier, diluent or excipient.

21. A veterinary composition comprising a compound, salt or solvate according to claim 1 admixed with a veterinarily acceptable carrier, diluent or excipient.

22. A method of treating stroke, dementia, memory enhancement, atherosclerosis, urge incontinence, hypertension, angina pectoris, congestive heart failure, myocardial infarction, restenosis, bladder outlet incontinence, stable, unstable, and variant (Prinzmetal) angina, pulmonary hypertension, and conditions of reduced blood vessel patency, which comprises administering to said mammal a therapeutically effective amount of a compound, salt or solvate according to claim 1, or a pharmaceutical composition or veterinary formulation containing any of the foregoing.

* * * * *